(12) United States Patent
Zung et al.

(10) Patent No.: US 8,663,248 B2
(45) Date of Patent: *Mar. 4, 2014

(54) ARTICULATING SUTURING DEVICE AND METHOD

(75) Inventors: Michael Zung, San Carlos, CA (US); Jasper Jackson, Newark, CA (US)

(73) Assignee: Abbott Laboratories, Abbott Park, IL (US)

( * ) Notice: Subject to any disclaimer, the term of this patent is extended or adjusted under 35 U.S.C. 154(b) by 357 days.

This patent is subject to a terminal disclaimer.

(21) Appl. No.: 12/334,077

(22) Filed: Dec. 12, 2008

(65) Prior Publication Data

US 2009/0088779 A1 Apr. 2, 2009

Related U.S. Application Data

(60) Continuation of application No. 10/660,288, filed on Sep. 11, 2003, now Pat. No. 8,137,364, which is a continuation-in-part of application No. 10/652,182, filed on Aug. 29, 2003, now Pat. No. 7,235,087, which is a continuation-in-part of application No. 10/357,984, filed on Feb. 4, 2003, now abandoned, which is a continuation-in-part of application No. 10/152,272, filed on May 20, 2002, now Pat. No. 6,964,668, which is a continuation-in-part of application No. 09/651,344, filed on Aug. 29, 2000, now Pat. No. 7,001,400, which is a division of application No. 09/262,402, filed on Mar. 4, 1999, now Pat. No. 6,136,010.

(51) Int. Cl.
*A61B 17/04* (2006.01)
*A61B 17/12* (2006.01)

(52) U.S. Cl.
USPC ............ 606/144; 606/138; 606/139; 606/148

(58) Field of Classification Search
USPC ......................................... 606/139, 144–150
See application file for complete search history.

(56) References Cited

U.S. PATENT DOCUMENTS

| | | | |
|---|---|---|---|
| 312,408 | A | 2/1885 | Wackerhagen |
| 597,165 | A | 1/1898 | Hall |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

U.S. Appl. No. 12/334,085, filed Dec. 12, 2008, Zung et al.

(Continued)

*Primary Examiner* — Gary Jackson
*Assistant Examiner* — Michael Mendoza
(74) *Attorney, Agent, or Firm* — Workman Nydegger; Randy Shen

(57) ABSTRACT

A device for closing an opening in tissue includes a shaft having a proximal end, a distal end, and at least one pin associated with a distal end the shaft. A flexible guidebody extends from the distal end of the shaft, while a foot associated with the device is movable with respect to the shaft through the pin connected to at least one slot of the foot. Another device for closing an opening in tissue includes a shaft having a proximal end and a distal end. A plurality of feet are disposed proximate the distal end of the shaft, the plurality of feet being movable with respect to the shaft. The device further includes a flexible guidebody extending from the distal end of the shaft.

14 Claims, 61 Drawing Sheets

(56) References Cited

U.S. PATENT DOCUMENTS

| | | |
|---|---|---|
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,108,206 A | 2/1938 | Meeker |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,610,631 A | 9/1952 | Calicchio |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,814,104 A | 6/1974 | Irnich et al. |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,011,872 A | 3/1977 | Komiya |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,501,276 A | 2/1985 | Lombardi |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,830,002 A | 5/1989 | Semm |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A * | 9/1992 | Ferzli ............................ 606/144 |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,287 A | 3/1993 | Fournier et al. |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,471 A | 6/1993 | Burkhart |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,237,996 A | 8/1993 | Waldman et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |

(56) References Cited

U.S. PATENT DOCUMENTS

| | | |
|---|---|---|
| 5,281,236 A | 1/1994 | Bagnato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | Van Tassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,279 A | 10/1994 | Hofling |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Della Badia et al. |
| 5,397,326 A | 3/1995 | Mangum |
| 5,403,329 A | 4/1995 | Hinchcliffe |
| 5,403,330 A | 4/1995 | Tuason |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A * | 6/1995 | Burbank et al. ............... 606/144 |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,478,354 A | 12/1995 | Tovey et al. |
| 5,480,407 A | 1/1996 | Wan et al. |
| 5,486,190 A | 1/1996 | Green |
| 5,489,295 A | 2/1996 | Piplani et al. |
| 5,492,119 A | 2/1996 | Abrams |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,267 A | 7/1996 | Edwards |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,647,372 A | 7/1997 | Tovey et al. |
| 5,649,959 A | 7/1997 | Hannam et al. |
| 5,662,664 A | 9/1997 | Gordon et al. |
| 5,669,917 A | 9/1997 | Sauer et al. |
| 5,672,174 A | 9/1997 | Gough et al. |
| 5,674,231 A | 10/1997 | Green et al. |
| 5,676,689 A | 10/1997 | Kensey et al. |
| 5,693,061 A | 12/1997 | Pierce et al. |
| 5,700,273 A | 12/1997 | Buelna et al. |
| 5,707,379 A | 1/1998 | Fleenor et al. |
| 5,713,899 A | 2/1998 | Marnay et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |

(56) References Cited

U.S. PATENT DOCUMENTS

| | | |
|---|---|---|
| 5,728,114 A | 3/1998 | Evans et al. |
| 5,728,133 A | 3/1998 | Kontos |
| 5,728,143 A | 3/1998 | Gough et al. |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,759,189 A | 6/1998 | Ferragamo et al. |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,576 A | 1/1999 | LeVeen et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,547 A | 9/1999 | Gough et al. |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,517 A | 11/1999 | Gough et al. |
| 5,980,539 A | 11/1999 | Kontos |
| 5,993,466 A | 11/1999 | Yoon |
| 5,993,476 A | 11/1999 | Groiso |
| 5,997,555 A | 12/1999 | Kontos |
| 6,001,109 A | 12/1999 | Kontos |
| 6,009,877 A | 1/2000 | Edwards |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,056,744 A | 5/2000 | Edwards |
| 6,068,603 A | 5/2000 | Suzuki |
| 6,077,276 A | 6/2000 | Kontos |
| 6,077,279 A | 6/2000 | Kontos |
| 6,083,242 A | 7/2000 | Cook |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,143,004 A | 11/2000 | Davis |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson et al. |
| 6,221,084 B1 | 4/2001 | Fleenor |
| 6,245,079 B1 | 6/2001 | Nobles et al. |
| 6,248,124 B1 | 6/2001 | Pedros et al. |
| 6,296,657 B1 | 10/2001 | Brucker |
| 6,306,081 B1 | 10/2001 | Ishikawa et al. |
| 6,322,580 B1 | 11/2001 | Kanner |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,397,110 B1 | 5/2002 | Kuzma |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,461,366 B1 | 10/2002 | Seguin |
| 6,511,489 B2 | 1/2003 | Field et al. |
| 6,517,498 B1 | 2/2003 | Burbank et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,159 B1 | 5/2003 | Edwards et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,689,051 B2 | 2/2004 | Nakada et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,776,785 B1 | 8/2004 | Yencho et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,029,480 B2 | 4/2006 | Klein et al. |

(56) References Cited

U.S. PATENT DOCUMENTS

| | | |
|---|---|---|
| 7,029,481 B1 | 4/2006 | Burdulis, Jr. et al. |
| 7,048,747 B2 | 5/2006 | Arcia et al. |
| 7,060,084 B1 | 6/2006 | Loshakove et al. |
| 7,063,661 B2 | 6/2006 | Okada |
| 7,063,710 B2 | 6/2006 | Takamoto et al. |
| 7,063,711 B1 | 6/2006 | Loshakove et al. |
| 7,083,635 B2 | 8/2006 | Ginn |
| 7,108,710 B2 | 9/2006 | Anderson |
| 7,112,225 B2 | 9/2006 | Ginn |
| 7,122,002 B2 | 10/2006 | Okada |
| 7,147,646 B2 | 12/2006 | Dana et al. |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,270,672 B1 | 9/2007 | Singer |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,431,727 B2 | 10/2008 | Cole et al. |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,507,200 B2 | 3/2009 | Okada |
| 7,727,249 B2 | 6/2010 | Rahmani |
| 7,731,655 B2 | 6/2010 | Smith et al. |
| 7,749,249 B2 | 7/2010 | Gelbart et al. |
| 7,753,923 B2 | 7/2010 | St. Goar et al. |
| 7,837,696 B2 | 11/2010 | Modesitt et al. |
| 8,211,122 B2 | 7/2012 | McIntosh |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2002/0188275 A1 | 12/2002 | McGuckin et al. |
| 2003/0093093 A1 | 5/2003 | Modesitt et al. |
| 2003/0195529 A1 | 10/2003 | Takamoto et al. |
| 2003/0233095 A1 | 12/2003 | Urbanski et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0210251 A1 | 10/2004 | Kontos |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0143761 A1 | 6/2005 | Modesitt |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0079914 A1 | 4/2006 | Modesitt et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0142785 A1 | 6/2006 | Modesitt et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2007/0005079 A1 | 1/2007 | Zarbatany et al. |
| 2007/0032798 A1 | 2/2007 | Pantages et al. |
| 2007/0032799 A1 | 2/2007 | Pantages et al. |
| 2007/0032801 A1 | 2/2007 | Pantages et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0112304 A1 | 5/2007 | Voss |
| 2007/0123817 A1 | 5/2007 | Khosravi et al. |
| 2007/0167959 A1 | 7/2007 | Modesitt et al. |
| 2007/0203506 A1 | 8/2007 | Sibbitt, Jr. et al. |
| 2007/0276410 A1 | 11/2007 | McIntosh |
| 2007/0282354 A1 | 12/2007 | McIntosh |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2008/0319458 A1 | 12/2008 | Reynolds |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0254119 A1 | 10/2009 | Sibbitt, Jr. et al. |
| 2010/0130965 A1 | 5/2010 | Sibbitt, Jr. et al. |
| 2012/0053600 A1 | 3/2012 | Fortson |
| 2012/0150201 A1 | 6/2012 | Pantages et al. |
| 2012/0316579 A1 | 12/2012 | Ma |
| 2013/0006277 A1 | 1/2013 | Stafford |
| 2013/0012962 A1 | 1/2013 | Stone |
| 2013/0066340 A1 | 3/2013 | Pantages et al. |
| 2013/0190781 A1 | 7/2013 | Fortson et al. |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 589 409 | 9/1992 |
| EP | 0 543 499 | 10/1992 |
| EP | 0 624 343 | 4/1993 |
| EP | 0 542 126 | 5/1993 |
| EP | 0 568 098 | 11/1993 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 3/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |

(56) References Cited

FOREIGN PATENT DOCUMENTS

| | | |
|---|---|---|
| SU | 1174036 | 8/1985 |
| SU | 1544383 | 2/1990 |
| SU | 1648400 | 5/1991 |
| WO | WO 85/03858 | 9/1985 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 01/35833 | 5/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 60/506,536, filed Sep. 26, 2003, McIntosh.
U.S. Appl. No. 60/540,811, filed Jan. 30, 2004, McIntosh.
U.S. Appl. No. 90/006,469, filed Nov. 29, 2002, Modesitt, et al.
Product Brochure, Laurus Medical Corporation, Irvine, CA "The Laurus In-Line Endoscopic Suturing Device" (Oct. 1994) 1 page.
U.S. Appl. No. 09/262,402, Mar. 29, 2000, Office Action.
U.S. Appl. No. 09/262,402, May 30, 2000, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 10/152,272, Jan. 24, 2005, Office Action.
U.S. Appl. No. 10/152,272, May 13, 2005, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/652,182, Jun. 8, 2007, Issue Notification.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/948,445, Jul. 11, 2007, Office Action.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 90/006,469, Nov. 29, 2002, Office Action.
U.S. Appl. No. 90/006,469, Sep. 10, 2004, Office Action.
U.S. Appl. No. 90/006,469, Sep. 27, 2005, Office Action.
U.S. Appl. No. 90/006,469, Jun. 27, 2006, Office Action.
U.S. Appl. No. 12/950,338, filed Nov. 19, 2010, Modesitt, et al.
U.S. Appl. No. 12/955,848, filed Nov. 29, 2010, Modesitt, et al.
U.S. Appl. No. 12/955,863, filed Nov. 29, 2010, Dawn Ma.
U.S. Appl. No. 12/955,869, filed Nov. 29, 2010, Voss.
U.S. Appl. No. 13/022,050, filed Feb. 7, 2011, Pantages et al.
U.S. Appl. No. 10/660,288, Mar. 29, 2011, Office Action.
U.S. Appl. No. 11/199,496, Apr. 28, 2011, Office Action.
U.S. Appl. No. 11/960,593, Apr. 28, 2011, Office Action.
U.S. Appl. No. 11/273,107, Jun. 2, 2011, Notice of Allowance.
U.S. Appl. No. 12/950,338, Jun. 15, 2011, Office Action.
U.S. Appl. No. 12/182,836, Jun. 23, 2011, Office Action.
U.S. Appl. No. 12/955,848, Jun. 30, 2011, Office Action.
U.S. Appl. No. 12/257,127, Jul. 6, 2011, Office Action.
U.S. Appl. No. 60/711,279, filed Aug. 24, 2005, Sibbitt, Jr et al.
U.S. Appl. No. 60/726,985, filed Oct. 14, 2005, Sibbitt Jr. et al.
U.S. Appl. No. 60/946,063, filed Jun. 25, 2007, Reynolds.
U.S. Appl. No. 61/097,072, filed Sep. 15, 2008, Sibbitt Jr. et al.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.

(56) References Cited

OTHER PUBLICATIONS

U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/877,974, Jul. 9, 2008, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Oct. 28, 2009, Office Action.
U.S. Appl. No. 11/273,107, Jun. 2, 2010, Office Action.
U.S. Appl. No. 11/273,107, Oct. 27, 2010, Office Action.
U.S. Appl. No. 11/316,775, Apr. 16, 2008, Office Action.
U.S. Appl. No. 11/316,775, Aug. 6, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/508,715, Oct. 18, 2010, Office Action.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,358, Oct. 19, 2010, Office Action.
U.S. Appl. No. 11/891,513, Apr. 9, 2010, Office Action.
U.S. Appl. No. 11/891,513, Sep. 28, 2010, Office Action.
U.S. Appl. No. 11/960,593, Sep. 14, 2010, Office Action.
U.S. Appl. No. 12/257,127, Aug. 30, 2010, Office Action.
U.S. Appl. No. 12/365,397, Sep. 13, 2010, Office Action.
U.S. Appl. No. 12/182,836, Oct. 5, 2010, Office Action.
U.S. Appl. No. 10/729,541, Nov. 23, 2010, Issue Notification.
U.S. Appl. No. 11/508,662, Oct. 26, 2010, Office Action.
U.S. Appl. No. 11/960,593, Nov. 3, 2010, Office Action.
U.S. Appl. No. 10/948,445, filed Sep. 22, 2004, McIntosh.
U.S. Appl. No. 12/961,239, filed Dec. 6, 2010, Modesitt, et al.
U.S. Appl. No. 12/966,961, filed Dec. 13, 2010, Modesitt, et al.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Rema-Medizintechnik GmbH, Product Brochure entitled "REMA," Apr. 2001, 7 pages.
Taber's Cyclopedic Medical Dictionary, 18th Ed., p. 747, Feb. 1997.
U.S. Appl. No. 10/909,531, Nov. 23, 2010, Issue Notification.
U.S. Appl. No. 11/363,005, Nov. 10, 2010, Issue Notification.
U.S. Appl. No. 11/465,527, Nov. 10, 2010, Issue Notification.
U.S. Appl. No. 11/552,593, Jul. 22, 2010, Notice of Allowance.
U.S. Appl. No. 11/552,593, Nov. 10, 2010, Issue Notification.
U.S. Appl. No. 11/688,722, Nov. 17, 2010, Issue Notification.
U.S. Appl. No. 12/257,127, Dec. 22, 2010, Office Action.
U.S. Appl. No. 12/334,085, Dec. 23, 2010, Office Action.
U.S. Appl. No. 12/950,338, Nov. 14, 2012, Issue Notification.
U.S. Appl. No. 13/022,050, Oct. 31, 2012, Issue Notification.
U.S. Appl. No. 12/334,085, Jan. 9, 2012, Notice of Allowance.
U.S. Appl. No. 12/955,863, Jan. 6, 2012, Office Action.
U.S. Appl. No. 12/955,869, May 30, 2012, Issue Notification.
U.S. Appl. No. 12/247,012, Aug. 13, 2012, Notice of Allowance.
U.S. Appl. No. 12/950,338, Aug. 8, 2012, Notice of Allowance.
U.S. Appl. No. 12/955,863, Aug. 8, 2012, Issue Notification.
U.S. Appl. No. 11/891,513, Aug. 15, 2012, Issue Notification.
U.S. Appl. No. 10/660,288, Sep. 30, 2011, Notice of Allowance.
U.S. Appl. No. 11/199,496, Aug. 18, 2011, Notice of Allowance.
U.S. Appl. No. 11/891,358, Aug. 31, 2011, Office Action.
U.S. Appl. No. 11/891,513, Aug. 31, 2011, Office Action.
U.S. Appl. No. 12/247,012, Oct. 13, 2011, Office Action.
U.S. Appl. No. 12/334,085, Aug. 4, 2011, Office Action.
U.S. Appl. No. 12/961,239, Jul. 26, 2011, Notice of Allowance.
U.S. Appl. No. 12/961,239, Oct. 12, 2011, Issue Notification.
U.S. Appl. No. 12/966,961, Aug. 18, 2011, Notice of Allowance.

(56) References Cited

OTHER PUBLICATIONS

U.S. Appl. No. 12/966,961, Oct. 26, 2011, Issue Notification.
U.S. Appl. No. 11/891,513, Nov. 1, 2011, Notice of Allowance.
U.S. Appl. No. 12/950,338, Nov. 1, 2011, Notice of Allowance.
U.S. Appl. No. 11/891,358, Apr. 10, 2012, Notice of Allowance.
U.S. Appl. No. 12/334,085, Apr. 18, 2012, Issue Notification.
U.S. Appl. No. 13/022,050, Apr. 26, 2012, Office Action.
U.S. Appl. No. 11/891,513, May 8, 2012, Notice of Allowance.
U.S. Appl. No. 11/997,379, May 11, 2012, Notice of Allowance.
U.S. Appl. No. 12/955,863, May 15, 2012, Notice of Allowance.
U.S. Appl. No. 13/525,875, filed Jun. 18, 2012, Voss.
U.S. Appl. No. 13/022,050, Jul. 6, 2012, Notice of Allowance.
U.S. Appl. No. 12/955,869, Oct. 18, 2011, Office Action.
U.S. Appl. No. 13/443,659, filed Apr. 10, 2012, Fortson et al.
U.S. Appl. No. 13/445,053, filed Apr. 24, 2012, Fortson et al.
U.S. Appl. No. 12/257,127, Sep. 20, 2012, Notice of Allowance.
U.S. Appl. No. 12/873,728, Sep. 11, 2012, Office Action.
U.S. Appl. No. 11/997,379, Aug. 29, 2012, Issue Notification.
U.S. Appl. No. 11/891,358, Nov. 18, 2011, Notice of Allowance.
U.S. Appl. No. 12/955,848, Nov. 15, 2011, Office Action.
U.S. Appl. No. 12/247,012, Mar. 16, 2012, Office Action.
U.S. Appl. No. 12/955,869, Mar. 22, 2012, Notice of Allowance.
U.S. Appl. No. 12/257,127, Jan. 12, 2012, Office Action.
U.S. Appl. No. 10/660,288, Feb. 29, 2012, Issue Notification.
U.S. Appl. No. 11/997,379, Feb. 28, 2012, Office Action.
U.S. Appl. No. 13/752,095, filed Jan. 28, 2013, McIntosh.
U.S. Appl. No. 12/247,012, Mar. 27, 2013, Issue Notification.
U.S. Appl. No. 13/593,154, Apr. 10, 2013, Issue Notification.
U.S. Appl. No. 13/615,530, Jan. 17, 2013, Office Action.
U.S. Appl. No. 13/870,628, filed Apr. 25, 2013, Ma.
U.S. Appl. No. 12/873,728, May 3, 2013, Office Action.
U.S. Appl. No. 13/615,530, Jun. 12, 2013, Notice of Allowance.
U.S. Appl. No. 11/960,593, Jul. 1, 2013, Notice of Allowance.
U.S. Appl. No. 12/873,728, Aug. 23, 2013, Office Action.
U.S. Appl. No. 12/257,127, Jan. 9, 2013, Issue Notification.
U.S. Appl. No. 13/593,154, Jan. 8, 2013, Notice of Allownace.
U.S. Appl. No. 11/997,379, Jul. 13, 2011, Office Action.
U.S. Appl. No. 13/022,050, Jul. 11, 2011, Office Action.
U.S. Appl. No. 12/182,836, May 17, 2013, Office Action.
US 5,820,544, 6/1974, Semm (withdrawn).
Cardiac Catheterization and Angiography, 3rd Ed., Lea N ad Febiger, Philadelphia, 1986. Elgiloy Brochure, Jun. 23, 1959, Elgin National Watch Co., Elgin, IL.
Cardio-Thoracic Systems Prospectus dated Mar. 20, 1996.
Datascope Corporation, Montvale, NJ (1991) 1 PG, American Heart Assoc. Meeting, Anaheim.
Kensey Nash Corporation, Exton, PA, "The Hemostatic Puncture Closure Device", 2 pages.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Serruys, PW et al., A Comparision of Balloon-Expandable-Stent Implantaion With Balloon Angioplasty in Patients With Coronary Artery Disease, New England Journal of Medicine, 331:489-495, 1994.
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.

* cited by examiner

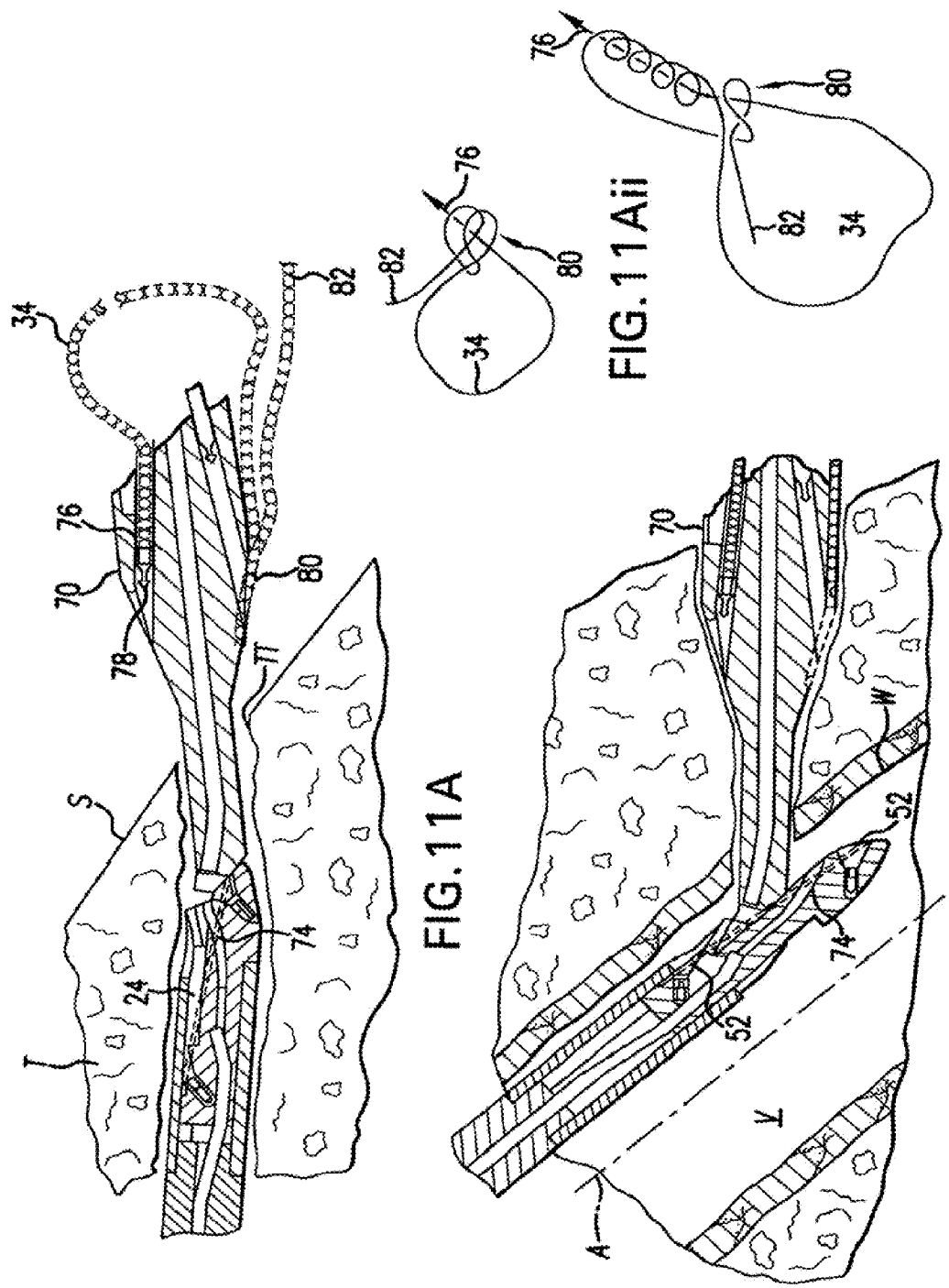

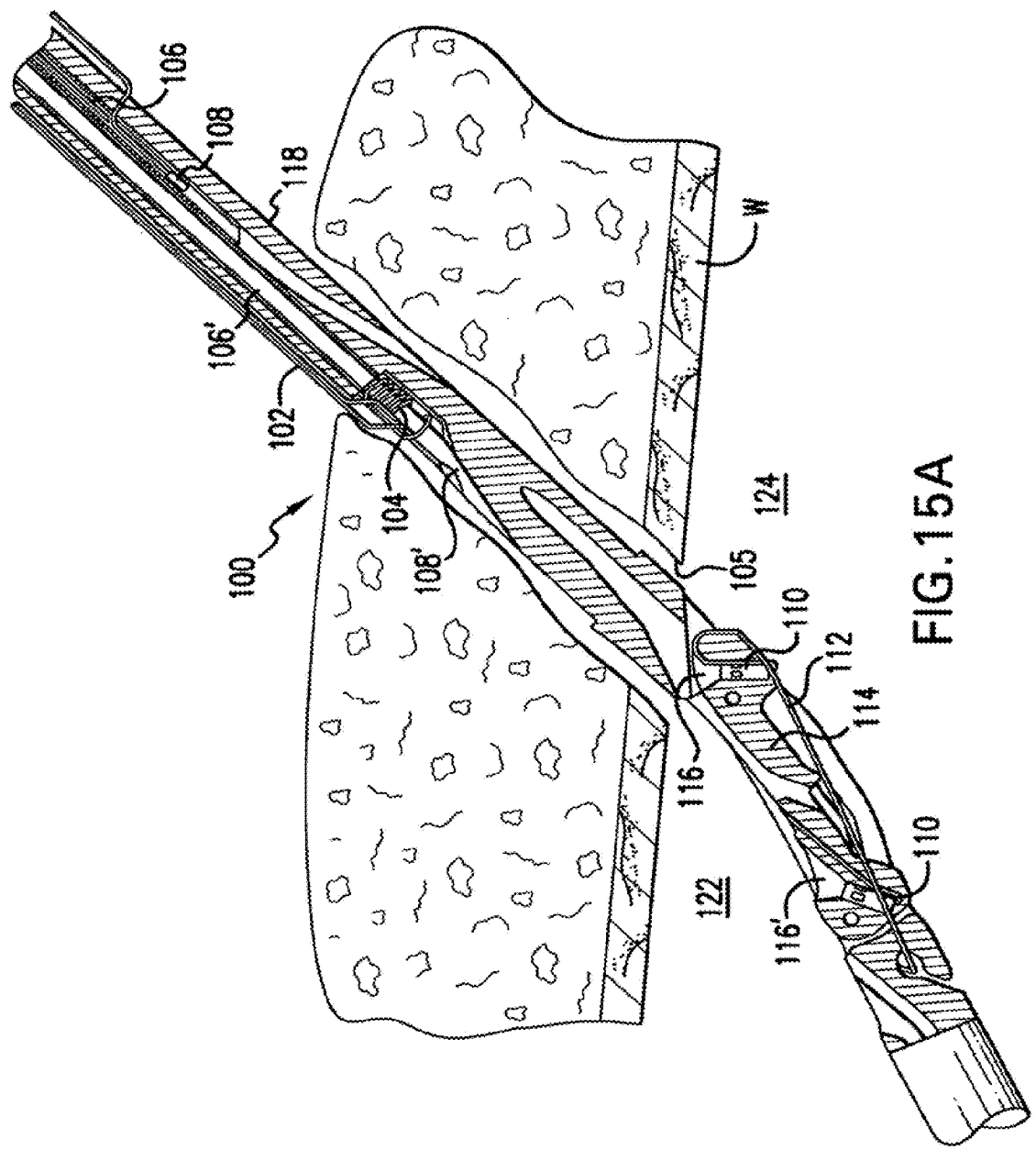

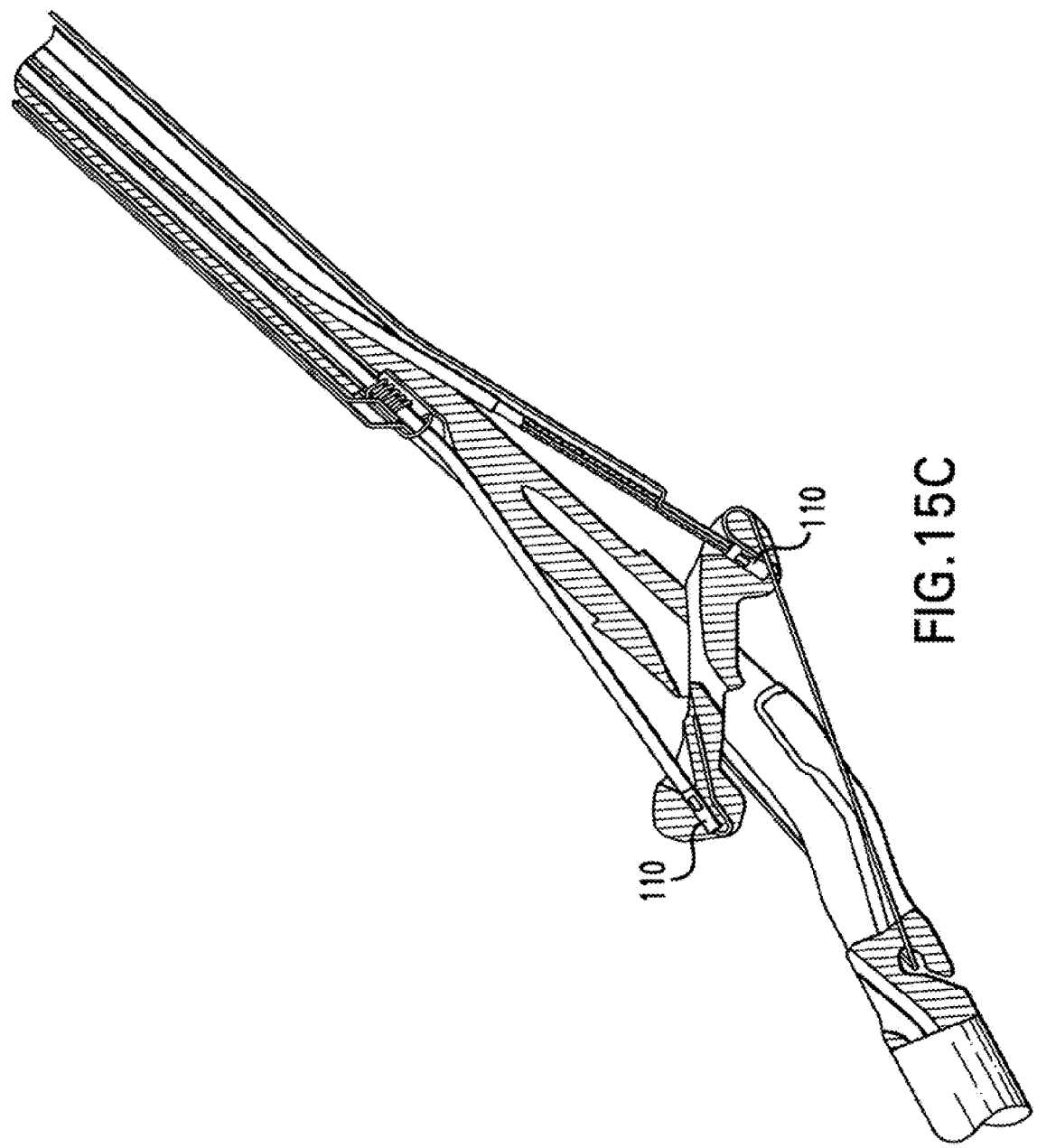

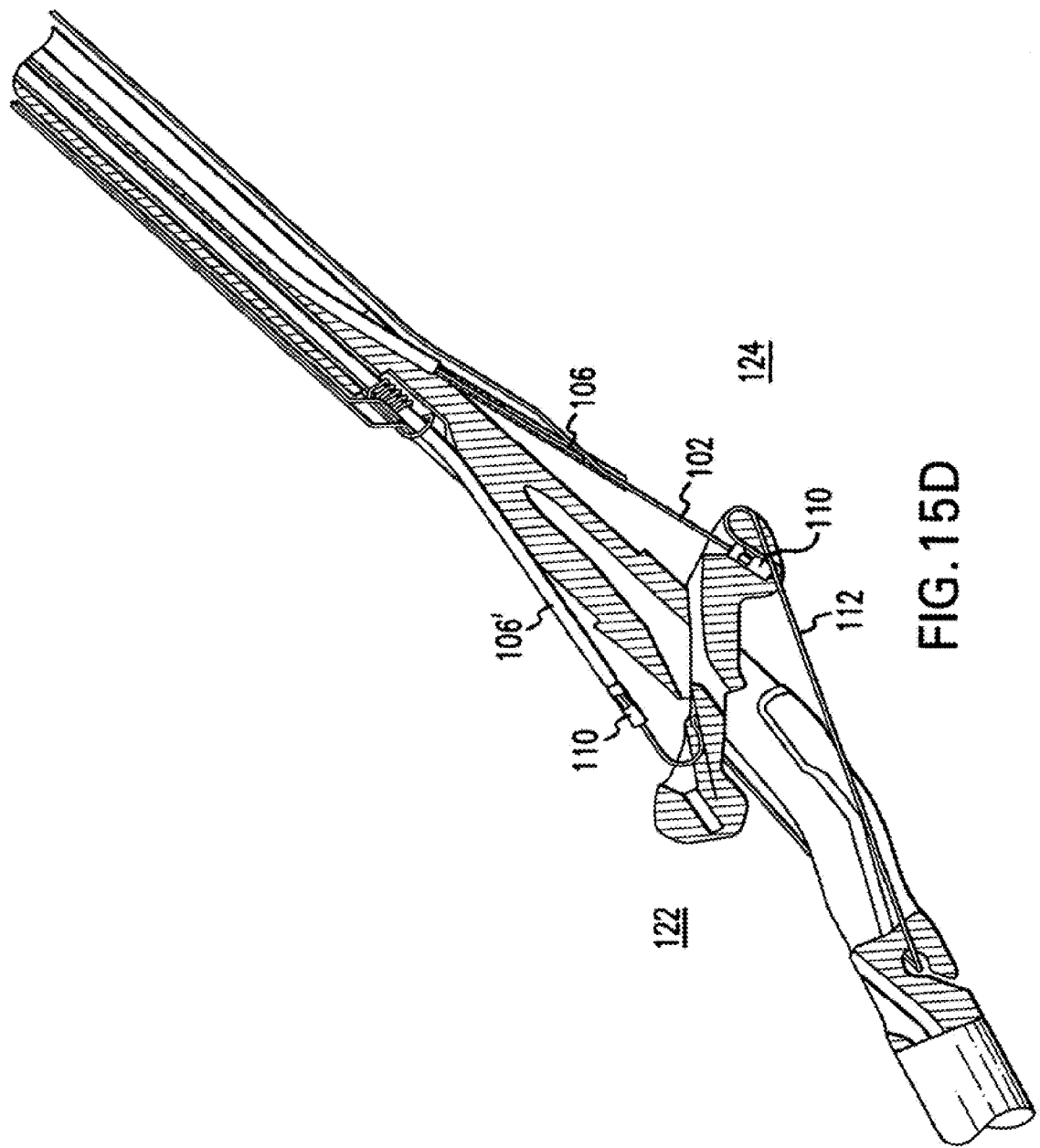

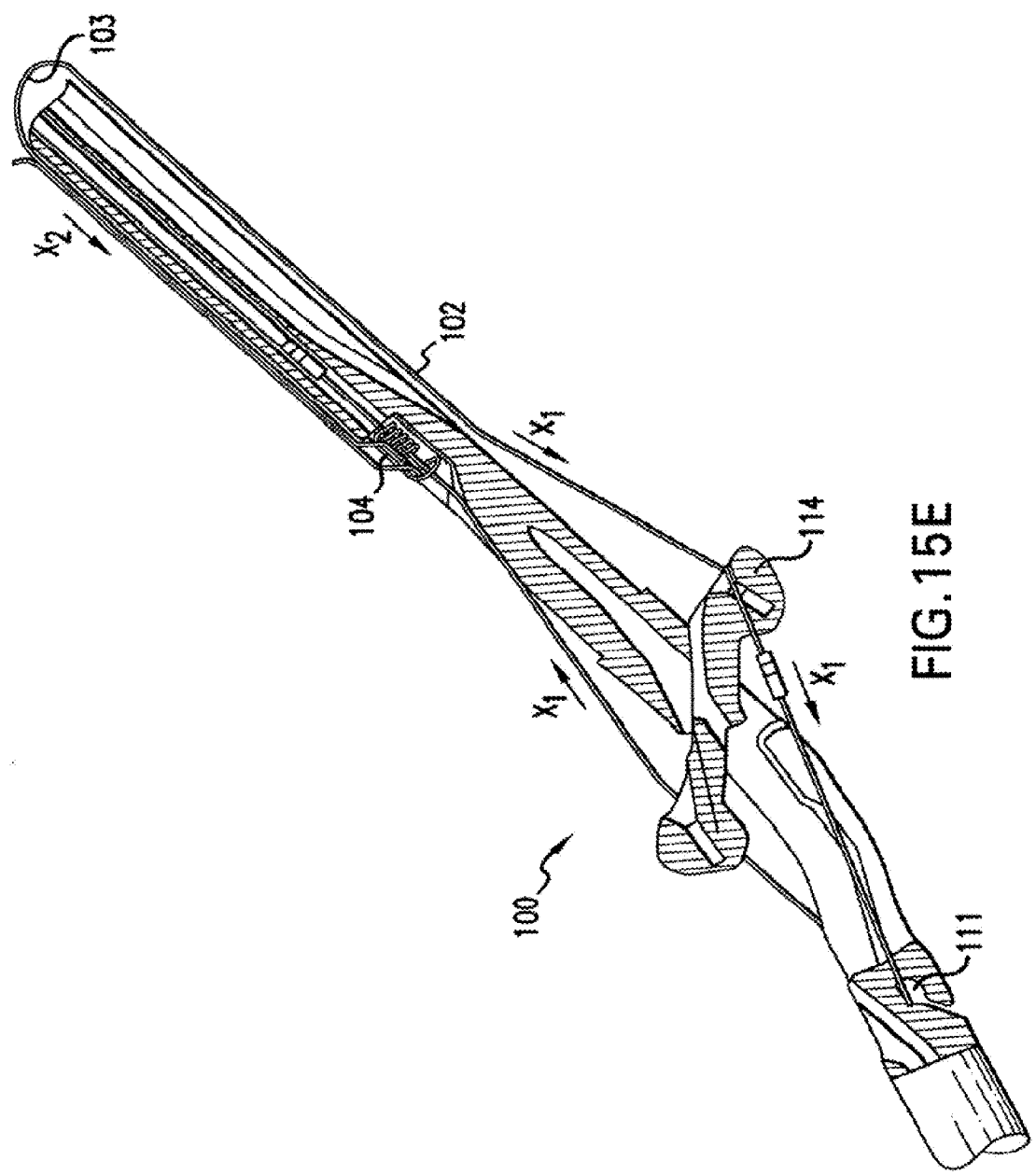

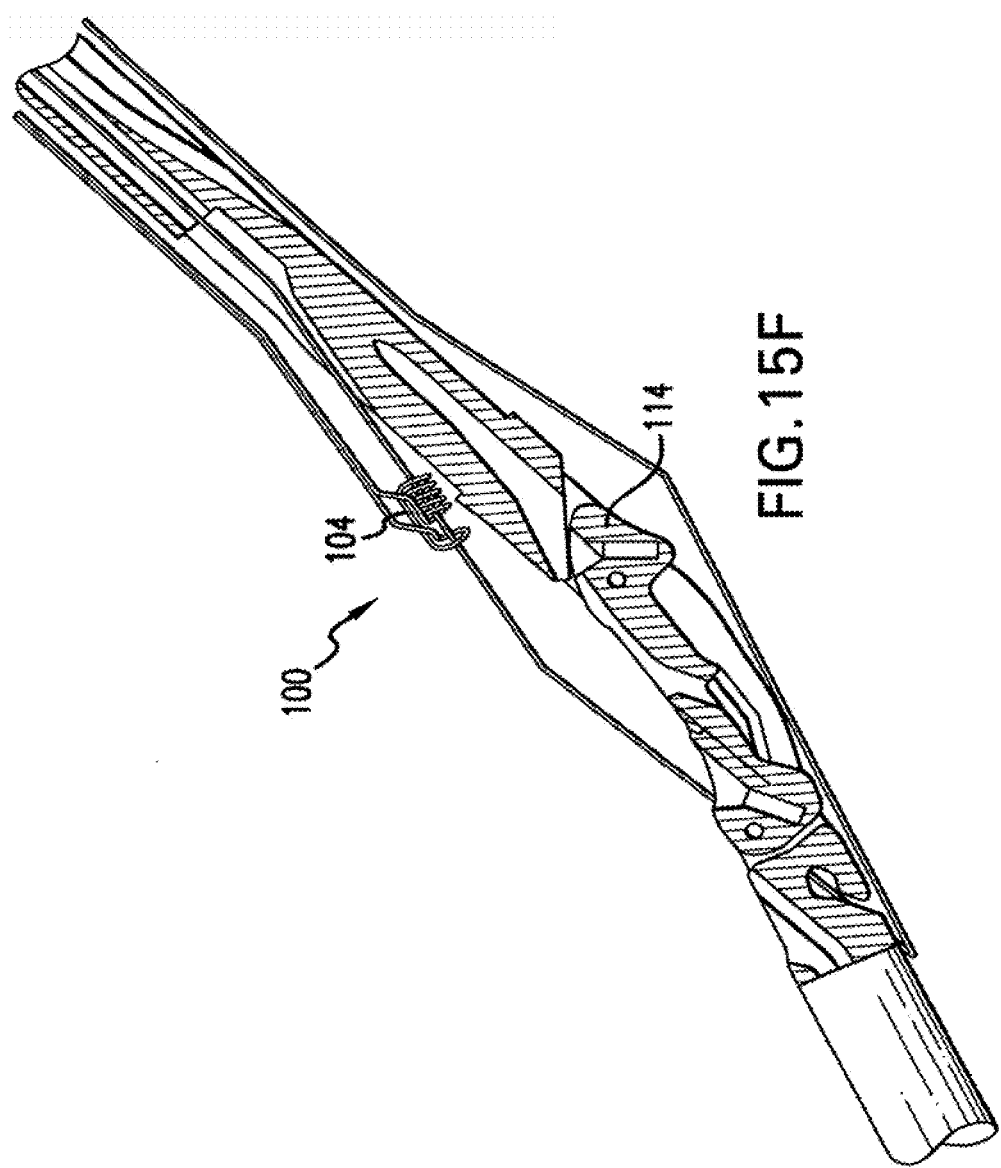

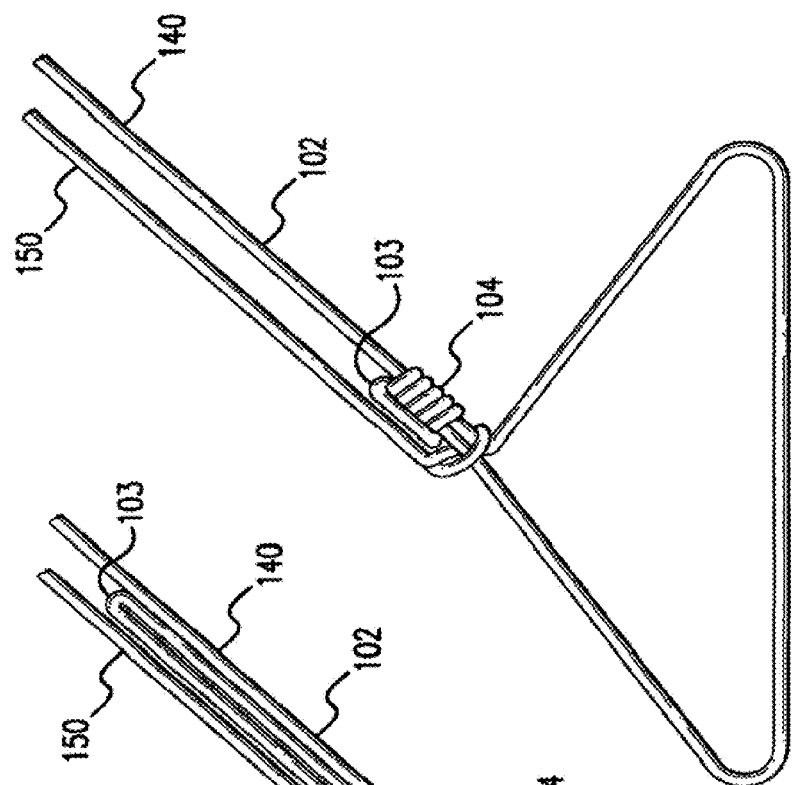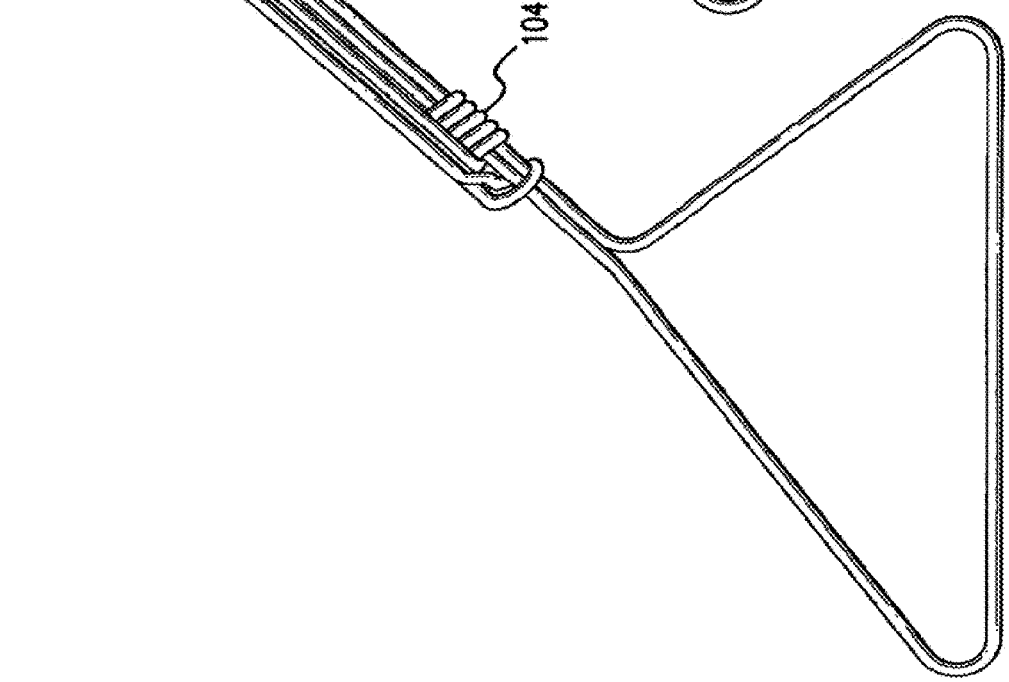

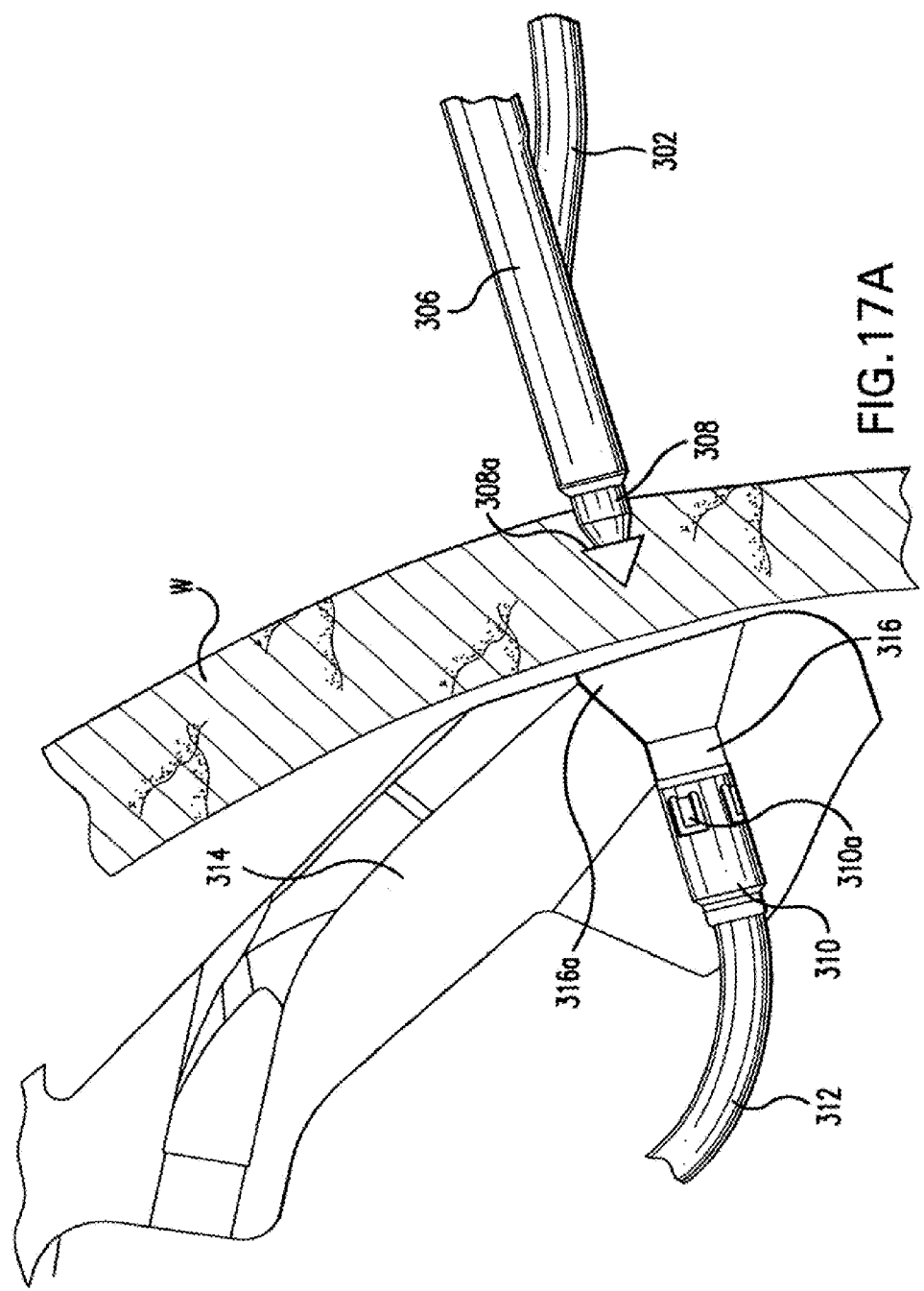

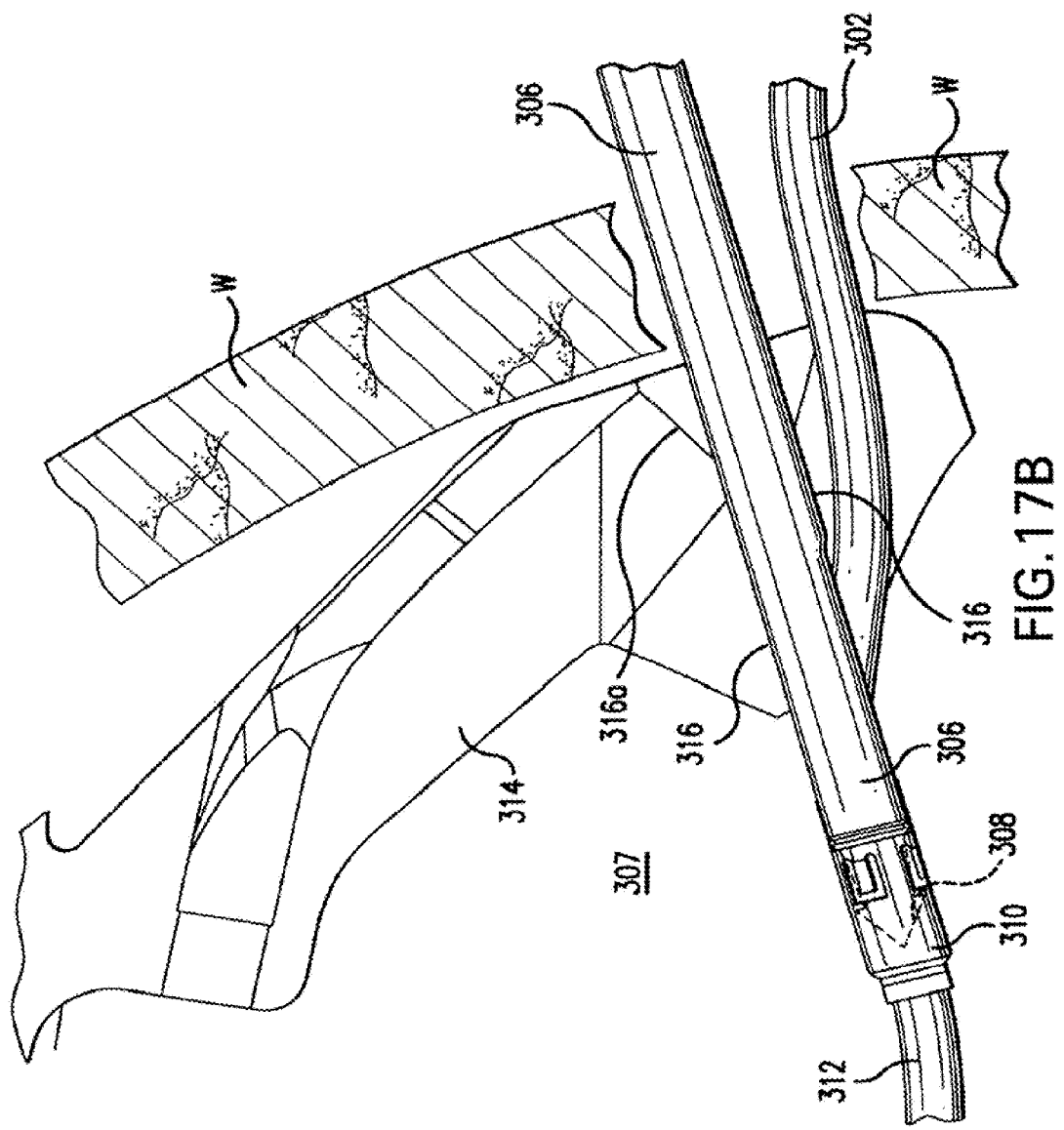

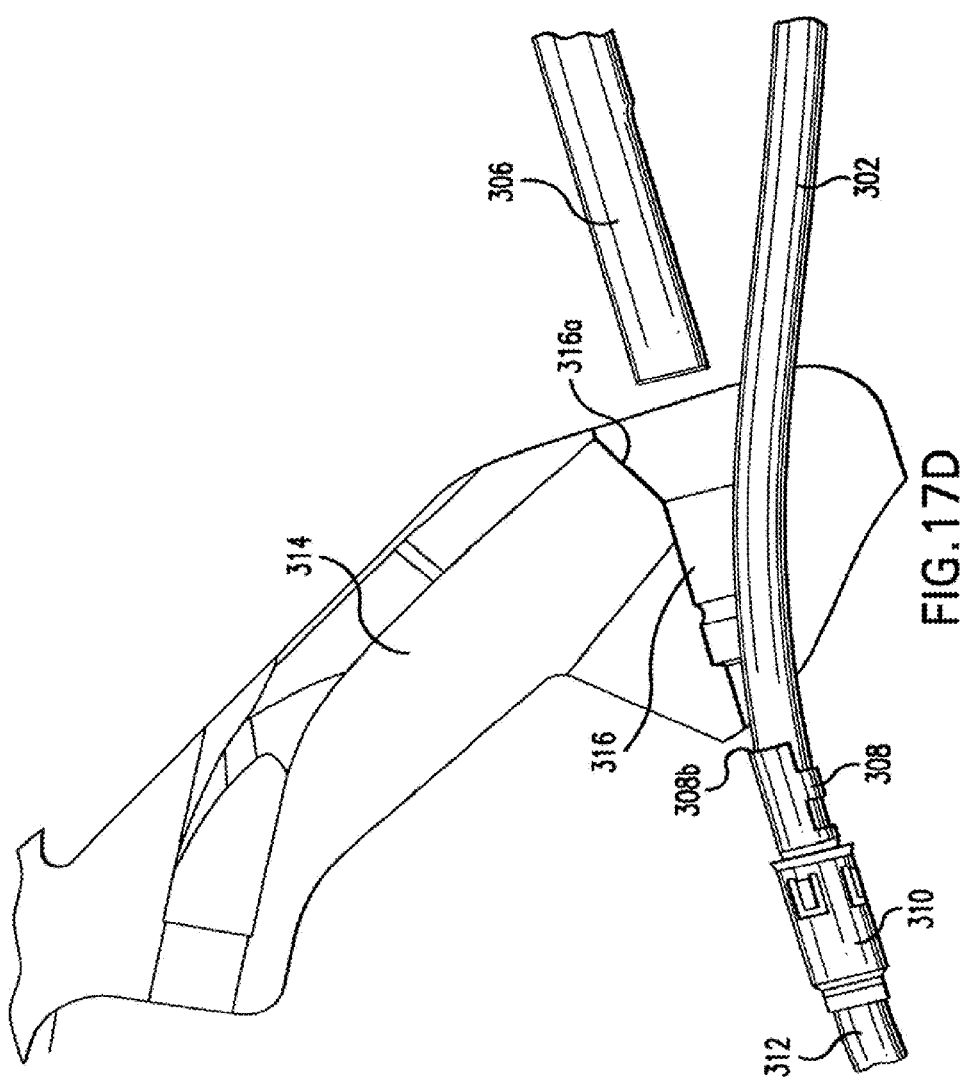

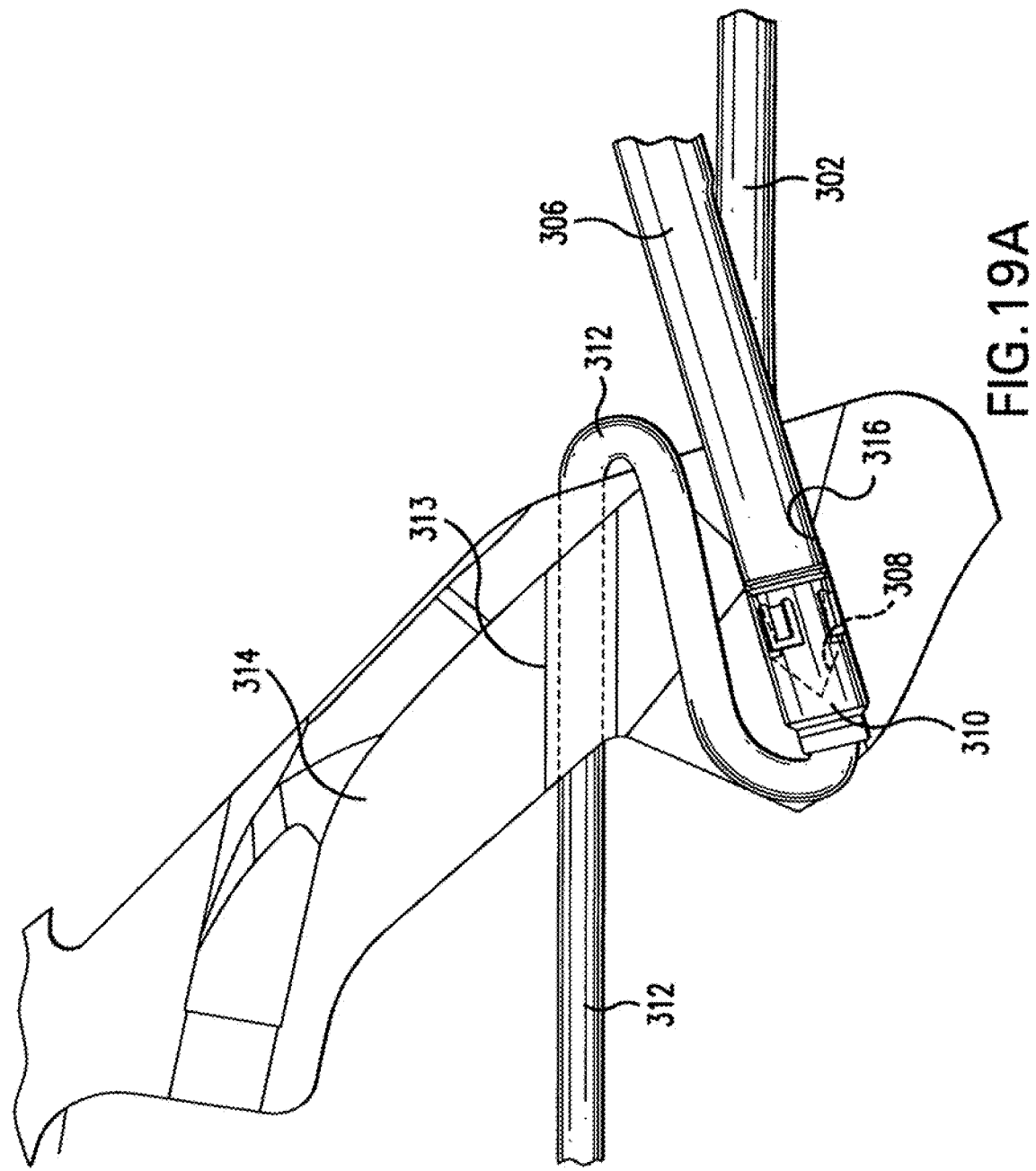

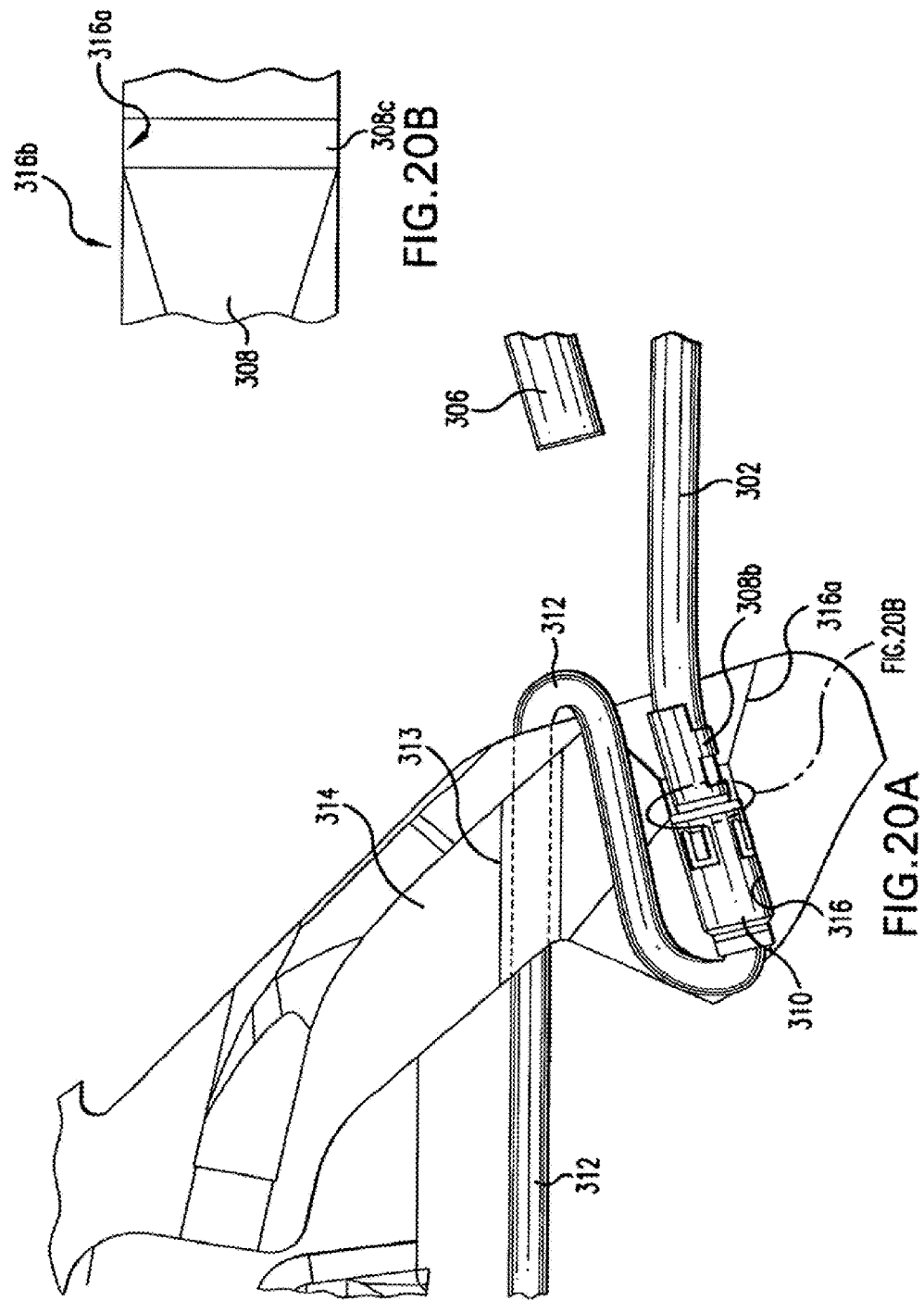

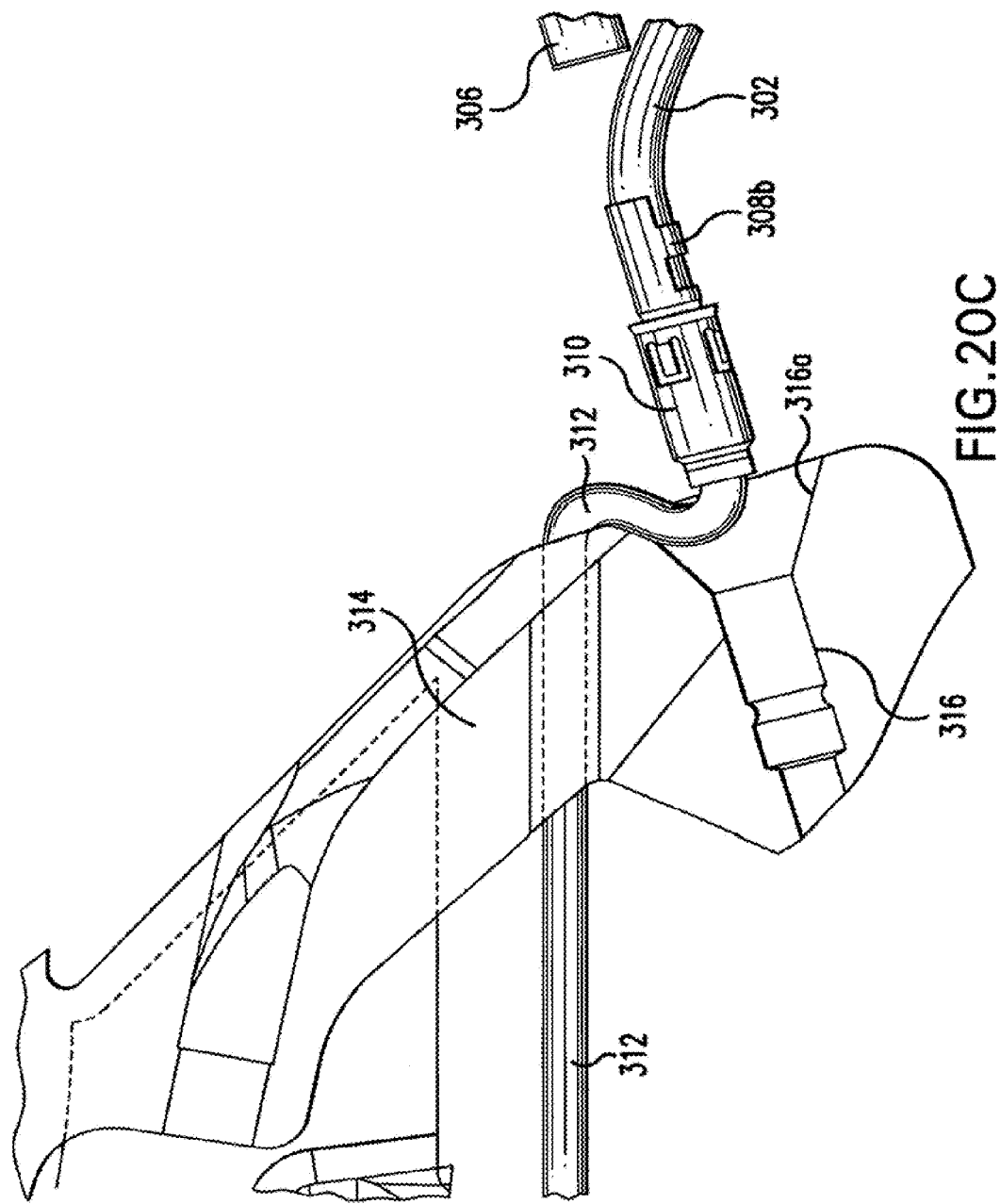

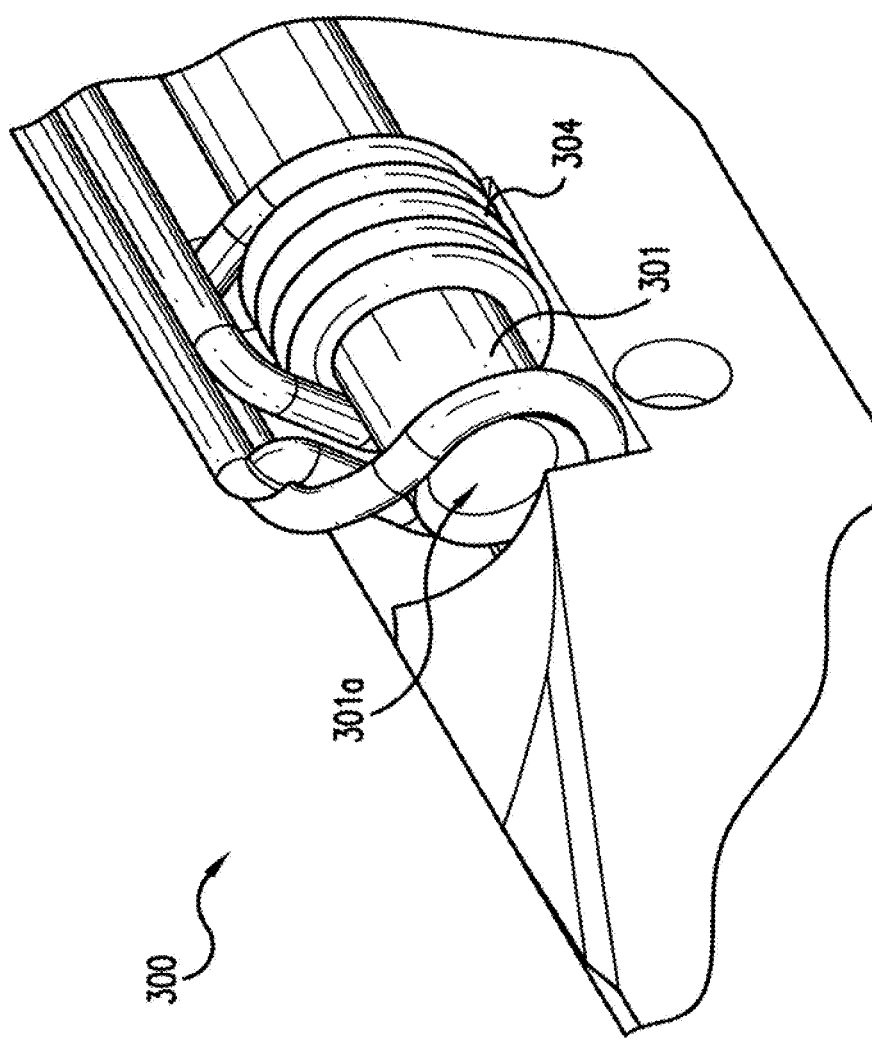

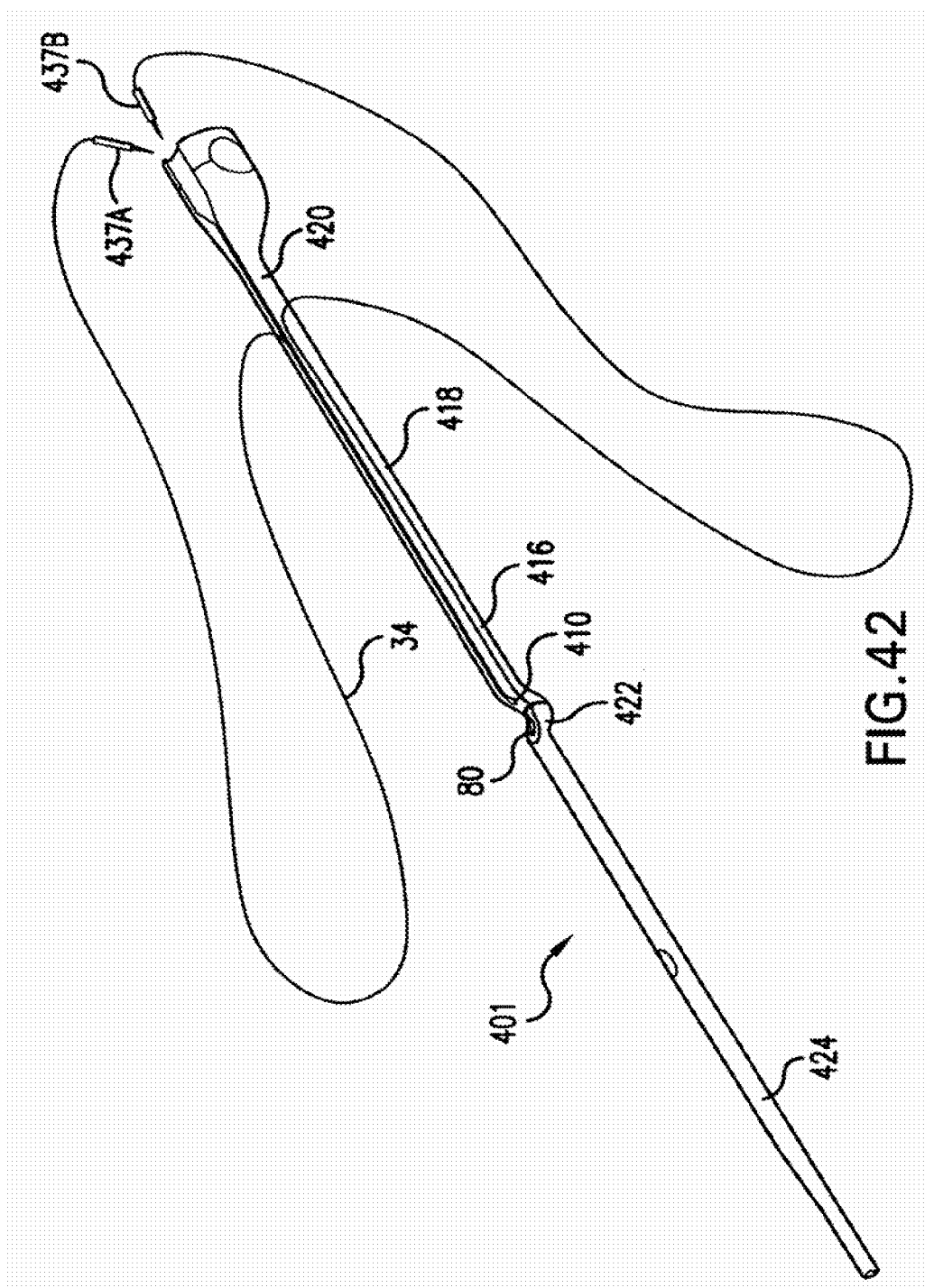

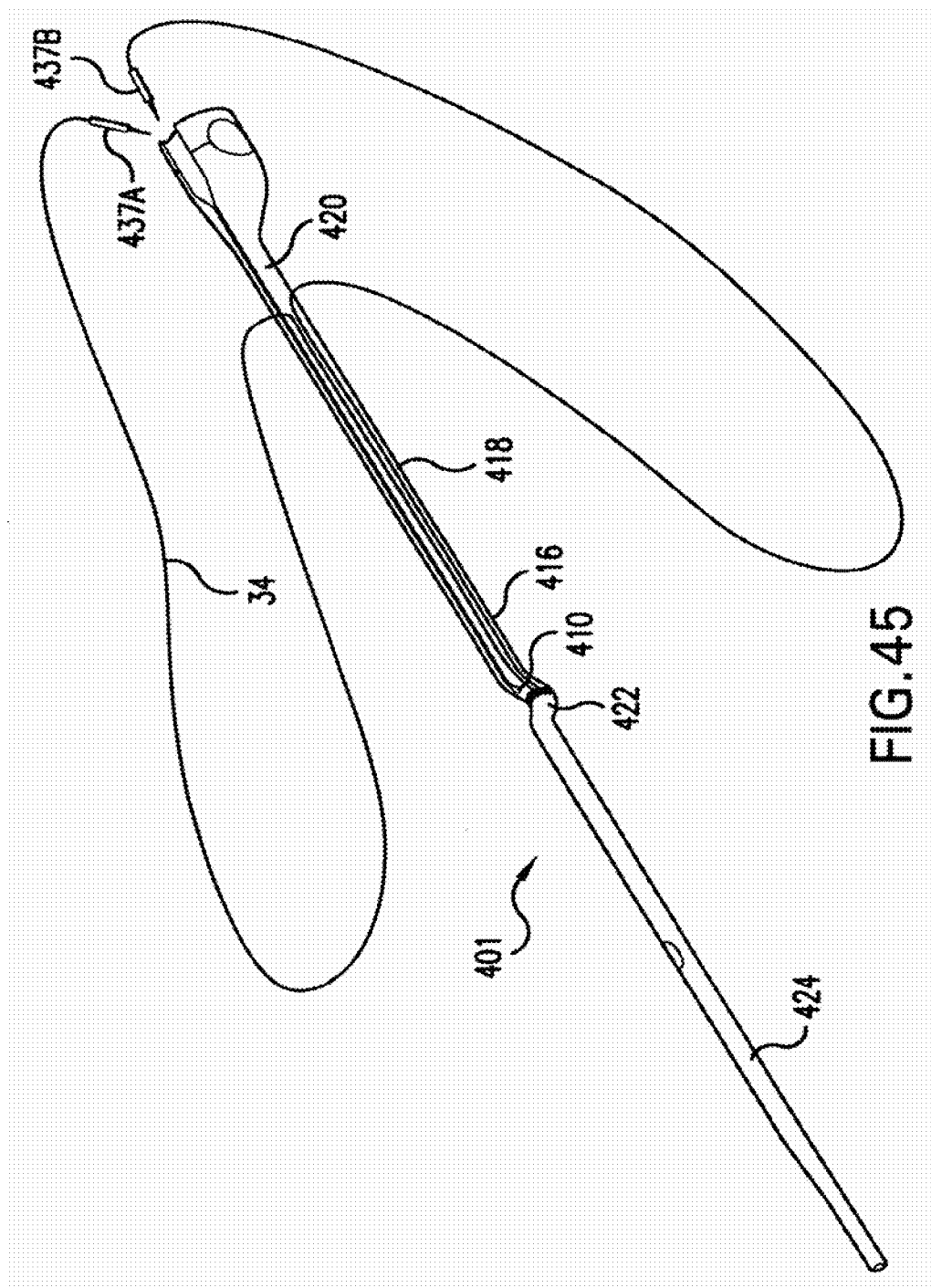

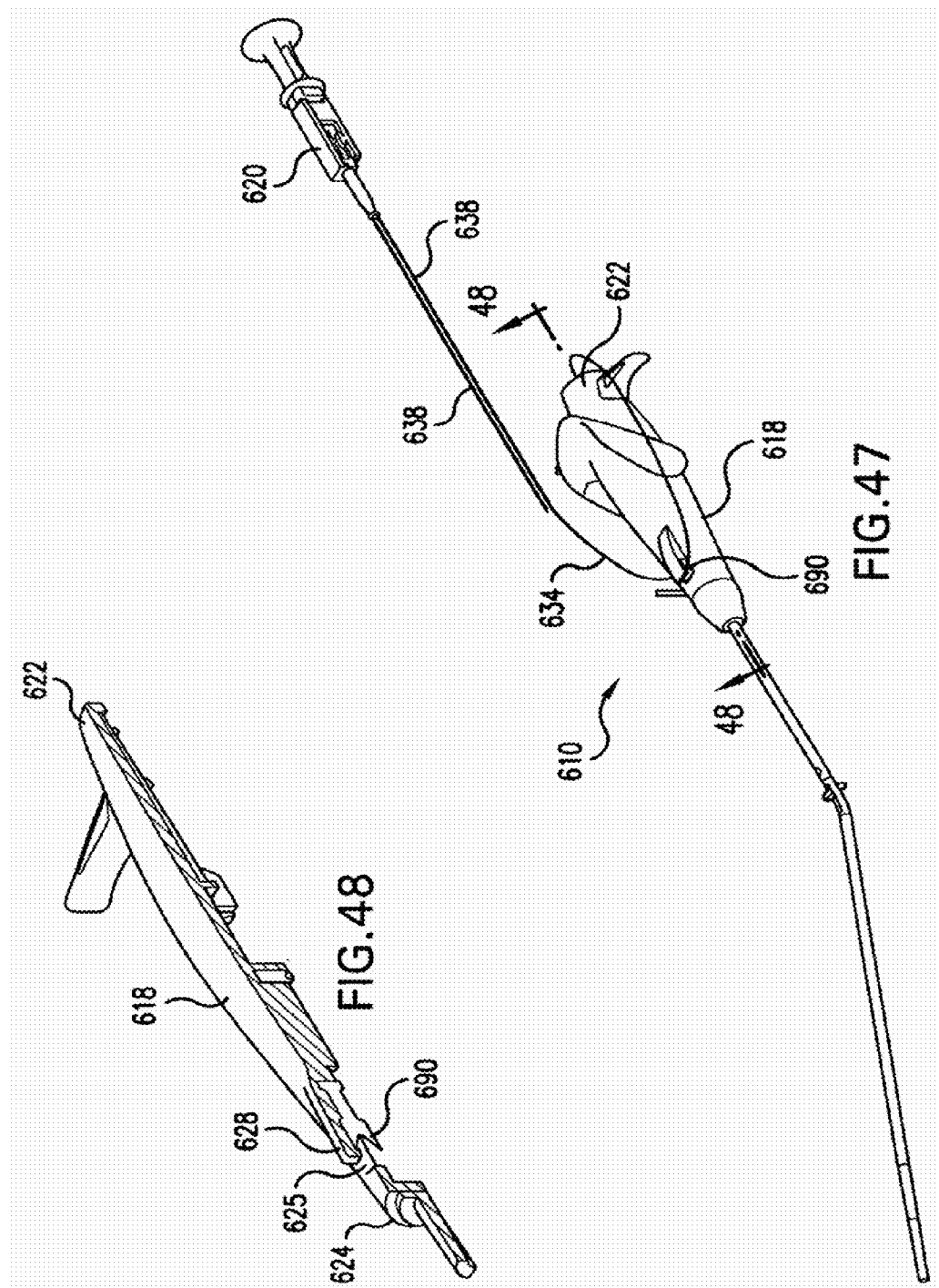

ARTICULATING SUTURING DEVICE AND METHOD

CROSS REFERENCE TO RELATED APPLICATIONS

This application is a continuation of and claims the benefit of priority from U.S. patent application Ser. No. 10/660,288, filed Sep. 11, 2003, and entitled "Articulating suturing device and method," now U.S. Pat. No. 8,137,364 which is a continuation-in-part of U.S. patent application Ser. No. 10/652,182, filed Aug. 29, 2003, and entitled "Articulating suturing device and method," now U.S. Pat. No. 7,235,087 which is a continuation-in-part of U.S. patent application Ser. No. 10/357,984, filed Feb. 4, 2003 now abandoned, and entitled "Articulating suturing device and method," which is a continuation-in-part of U.S. patent application Ser. No. 10/152,272, filed May 20, 2002, and entitled "Articulating suturing device and method," now U.S. Pat. No. 6,964,668, which is a continuation-in-part of U.S. patent application Ser. No. 09/651,344, filed Aug. 29, 2000, and entitled "Articulating suturing device and method," now U.S. Pat. No. 7,001,400, which is a division of U.S. patent application Ser. No. 09/262,402, filed on Mar. 4, 1999, and entitled "Articulating suturing device and method," now U.S. Pat. No. 6,136,010, each of which is hereby incorporated by reference in its entirety.

BACKGROUND OF THE INVENTION

The present invention relates generally to apparatus and methods for the suturing of body lumens. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," 3.sup.rd Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. Such devices would have the capability of delivering a pre-tied knot to an incision site. It would be particularly beneficial if these improved devices provided some or all of the benefits while overcoming one or more of the disadvantages discussed above.

DESCRIPTION OF THE BACKGROUND ART

U.S. Pat. Nos. 5,700,273, 5,836,956, and 5,846,253 describe a wound closure apparatus and method in which needles are threaded with suture inside a blood vessel. U.S. Pat. No. 5,496,332 describes a wound closure apparatus and method for its use, while U.S. Pat. No. 5,364,408 describes an endoscopic suture system.

U.S. Pat. No. 5,374,275 describes a surgical suturing device and method of use, while U.S. Pat. No. 5,417,699 describes a device and method for the percutaneous suturing of a vascular puncture site. An instrument for closing trocar puncture wounds is described in U.S. Pat. No. 5,470,338, and a related device is described in U.S. Pat. No. 5,527,321, U.S. Pat. No. 5,507,757 also describes a method of closing puncture wounds.

SUMMARY OF THE INVENTION

The present invention provides improved devices, systems, and methods for suturing of body lumens. The device often allows the suturing of vascular puncture sites located at the distal end of a percutaneous tissue tract with greater ease, in less time, and with less patient trauma than known systems. These improvements are generally provided through the use of shafts having smaller cross-sections than prior suturing systems. In the exemplary embodiment, an elongate articulated foot near a distal end of a shaft is inserted through the penetration and actuated so that the foot extends along the lumenal axis. The foot carries suture attachment cuffs, and can be drawn proximally up against the endothelial surface of the blood vessel. Needles are advanced from the shaft, through the vessel wall beyond the penetration, and into engagement with the needle cuffs. The cross-section of the shaft within the tissue tract can be minimized by laterally deflecting the needles before they leave the shaft, while tapered depressions within the foot can help guide the advancing needles into engagement with the cuffs. The cuffs lockingly engage the needles so that the cuffs can be withdrawn proximally along the needle paths through the tissue tract so as to form a loop of suture across the puncture without having to thread the needles directly with the suture inside the blood vessel. The suture loop may be drawn distally from the shaft, proximally from within the blood vessel, or laterally down one of the needle paths, across the puncture, and out the opposing path. Regardless, the articulating foot may be realigned with the shaft and withdrawn proximally through the tissue tract in a small profile configuration. The use of an articulatable foot in combination with lateral deflection of the needles can avoid dilation of the tissue tract, as was often necessary using known puncture closure systems.

In a first aspect, the invention provides a method for suturing a puncture through a vessel wall of a blood vessel. The puncture is disposed within a tissue tract of a patient body, and the method comprises attaching a flexible filament to a first fitting. The first fitting is inserted through the tissue tract and positioned adjacent the vessel wall, and a needle path is formed by advancing a first needle through the vessel wall. The needle is coupled with the first fitting, and the first needle, the first fitting, and at least a portion of the filament are withdrawn through the vessel wall along the needle path.

First and second fittings will often be coupled to the flexible filament, and will generally be positioned so that the puncture is disposed therebetween. The flexible filament will often comprise a suture extending between the first and second fittings, with each fitting being drawn proximally by an associated needle so as to form the suture loop. Alternatively, at least one of the needles may include a detachable tip and may advance a suture distally along the needle path as the needle penetrates through the vessel wall. The flexible filament can again couple the first and second fittings, here allowing both fittings to be withdrawn along a single needle path so that the suture advances down along the first needle path, laterally across the puncture, and then out the other needle path.

Positioning of the fittings is generally effected by articulating an elongate foot within the blood vessel so that the foot extends along the vessel axis. A confirmation lumen may extend along a shaft supporting the foot to ensure that the foot is positioned within the vessel prior to articulation. Once the foot is properly articulated, it can be drawn proximally to firmly engage the endothelial layer of the vessel. The foot will preferably include tapering depressions which direct the advancing needle toward the fitting, and the suture or other flexible filament adjacent the fittings will often be releasably restrained within a narrow slot extending from the depression. The suture or other flexible filament and its associated slot will preferably be arranged to avoid entanglement of the advancing needle in the suture, and to ensure that the fitting and suture can be withdrawn proximally as the needle is retracted. An atraumatic, flexible monorail guidebody may extend from the shaft and/or the articulatable foot to facilitate alignment of the foot with the vessel, and also to help provide hemostasis while the knot is tied. A wide variety of foot articulation mechanisms may be provided, with deployment preferably being effected when the foot is disposed entirely within the vessel and using an actuator and foot motion that avoid dilation of the puncture.

In another aspect, the invention provides a method for suturing an opening in a tissue. The method comprises inserting a distal end of a probe through the opening, the probe defining a probe axis. An elongated foot of the probe is articulated so that first and second ends of the foot extend laterally with the opening aligned therebetween. A first needle path is formed from the probe, through the tissue, and to the first end of the foot. A second needle path is formed from the probe, through the tissue, and to the second end of the foot. Suture is advanced along the first and second needle paths to position a suture loop across the opening.

In another aspect, the invention provides a method for suturing a blood vessel. The vessel has a vessel wall, and the method comprises advancing a shaft toward the vessel wall. The shaft has an axis and a plurality of needle guides. A foot is deployed adjacent the vessel wall so that the foot extends laterally from the shaft. A plurality of needles are advanced from the needle guides of the shaft to the foot to form needle paths through the vessel wall. The needle guides deflect the needles laterally so that a needle path width between the needles is greater than a cross-sectional dimension of the shaft. Suture is advanced along the needle paths to position at least one suture loop across the puncture.

In yet another method of the present invention, a blood vessel is sutured through a tissue tract of a patient body. The vessel has a vessel wall, and the method comprises inserting a distal end of a probe through the puncture and into the blood vessel. A first end of the suture is advanced from the probe within the tissue tract, through the vessel wall, and into the vessel. The first end of the suture is withdrawn from the vessel through the vessel wall, and through a bight of the suture to form a loop of suture across the puncture. The first end of the suture and a second end of the suture adjacent the bight are tensioned to detach the bight from the probe and form a knot affixing the loop of suture across the puncture. Advantageously, the bight of suture may be pre-tied before the probe is inserted into the tissue tract, the bight optionally being releasably attached to the probe.

In a device aspect, the invention provides a system for suturing a blood vessel. The vessel has a vessel wall, and the system comprises a needle having a proximal end and a distal end suitable for forming a needle path through the vessel wall. The needle has a recessed engagement surface adjacent the distal end. The system further comprises a flexible filament and a fitting attached to the filament. The fitting has an opening and a tab extending into the opening, the tab securingly engaging the engagement surface when the needle advances through the vessel wall and into the opening, so that the fitting and at least a portion of the filament can be withdrawn proximally along the needle path by the needle.

In a further device aspect, the invention provides a system for suturing a puncture of a blood vessel within a tissue tract. The vessel has a vessel wall and defines an axis, and the system comprises a shaft having a proximal handle and a distal end suitable for insertion along the tissue tract and into the vessel through the puncture. A foot is mounted near the distal end of the shaft. The foot has plurality of needle receptacles extendable laterally from the shaft. A flexible filament extends between the receptacles of the foot. A plurality of needles are advanceable distally and laterally from the shaft, through the vessel wall outside the puncture, and to the receptacles of the foot.

In yet another device aspect, the invention provides a system for suturing a puncture of a blood vessel within a tissue tract. The vessel has a vessel wall, and the system comprises a shaft having a proximal handle and a distal end suitable for insertion along the tissue tract and into the vessel through the puncture. A foot is mounted near the distal end of the shaft. The foot has a first needle receptacle and is articulatable from a small profile configuration to a large profile configuration by actuation of the handle. A first fitting is removably mounted adjacent the first needle receptacle. A filament is coupled to the first fitting. A first needle is advanceable from the shaft to the first needle receptacle on the articulated foot. The first fitting securely engages the first needle so that the secured first fitting and at least a portion of the filament can be drawn through the vessel wall by the first needle.

In a still further device aspect, the invention provides a probe for suturing an opening in a tissue. The probe comprises a shaft having a proximal end and a distal end and defining an axis therebetween. The shaft has a size and configuration suitable for insertion through the opening in the tissue. An elongate foot is movably mounted to the shaft. An actuator extends along the shaft distally to the foot. Movement of the actuator slides the foot axially and pivots the foot from a low profile configuration to a deployed configuration extending laterally from the shaft. A suture is supported by the foot, and a needle is advanceable from the shaft, through the tissue, and to the deployed foot.

In another aspect, the invention provides a suturing device having a first penetrator and a second penetrator for suturing an incision. The first penetrator is configured to form a first penetration about a periphery of the incision. The first penetrator also carries a pre-tied knot disposed about a periphery of the first penetrator for delivery to the incision. The second penetrator is configured to form a second penetration about the periphery of the incision. The second penetrator also includes suture disposed thereon that is drawn by the first penetrator through the first penetration and through the pre-tied knot during retraction of the first and second penetrators from around the periphery of the incision. The first penetrator draws the suture through the first penetration via a connection between the first penetrator and the suture. Moreover, as the first penetrator draws the suture, the suture delivers the pre-tied knot to the incision for closure of the incision.

In another aspect, the invention provides a suturing device for suturing an incision formed in an artery. The suturing device includes a first penetrator, a second penetrator and a receiver. The first penetrator, which forms a first penetration about a periphery of the incision, includes a pre-tied knot disposed about the first penetrator. The second penetrator, which forms a second penetration about the periphery of the incision, has suture disposed thereon, which retracts through the first penetration. The suture retracts through the first penetration into the pre-tied knot during retraction of both the first penetrator and the second penetrator from around the periphery of the incision. In addition, during retraction, the suture delivers the pre-tied knot to the incision for suturing of the incision. The suturing device also includes a receiver for receiving both the first penetrator and the second penetrator upon penetration formation. The receiver connects the suture to both the first penetrator and the second penetrator and allows retraction of the suture through the first penetration as the first penetrator and the second penetrator retract.

In another aspect, the invention provides a suturing device for suturing an opening of an artery of a patient during a surgical procedure. The suturing device includes a first penetrator, a second penetrator and a foot. The first penetrator is disposed about a periphery of the suturing device and the second penetrator is located opposite the first penetrator on the suturing device. The first penetrator includes a pre-tied knot configured to receive suture releasably engaged with the second penetrator during suturing of the opening of the artery. The foot, which is movably coupled to the suturing device distal to the first penetrator and the second penetrator, includes a first cuff and a second cuff. The first cuff and the second cuff, which couple to one another via a link, receive the first penetrator and a detachable end of the second penetrator respectively. The first and second penetrators penetrate the artery at a proximal end of the suturing device and couple with the first cuff and the second cuff upon penetration of the artery. The first and second penetrators couple with the first cuff and second cuff such that during retraction of the first penetrator and the second penetrator from the artery, the suture delivers the pre-tied knot to the incision for closure of the incision.

In various aspects and embodiments of the invention described herein, a pre-tied knot of suture is also included. The pre-tied knot may initially be positioned wrapped around an exterior surface of the device. Specifically, a length of suture having opposite ends and a bight of suture therebetween is provided with the bight being disposed around an exterior surface of the device.

In other aspects and embodiments described herein, a suture cutting blade is positioned on the device. The suture cutting blade provides a convenient cutting edge across which the suture can be drawn to sever the suture from the needle.

BRIEF DESCRIPTION OF THE DRAWINGS

FIGS. 11A-E illustrate an alternative closure system and method for its use in which a first needle advances the suture to the foot, while a second needle engages and withdraws both the first and second suture cuffs, a flexible filament connecting the suture cuffs, and at least a portion of the suture from within the blood vessel so as to complete a pre-tied knot.

FIGS. 15A through 15F are enlarged cross-sectional views of the embodiment of the suturing device of FIGS. 14A and 14B.

FIGS. 16A and 16B are schematic views of a suture bight having a pre-tied knot in accordance with one embodiment of the present invention.

FIGS. 17A through 17D show enlarged partial cross-sectional views of an embodiment of the suturing device in accordance with the invention, in which one embodiment of a penetrator tip and cuff engagement, penetrator tip disengagement, and cuff ejection sequence is illustrated.

FIGS. 19A and 19B are enlarged partial cross-sectional views of an embodiment of a foot in accordance with the present invention, showing an alternate penetrator tip and cuff engagement, penetrator tip disengagement, and cuff ejection sequence.

FIGS. 20A through 20C are enlarged partial cross-sectional views of an embodiment of a foot in accordance with the present invention, showing an alternate penetrator tip and cuff engagement, penetrator tip disengagement, and cuff ejection sequence.

FIG. 21 is an enlarged perspective view of an embodiment of the pre-tied knot in accordance with the present invention.

FIG. 42 is a perspective view illustrating a vessel closure device incorporating an embodiment of a pre-tied knot according to the principles of the present invention.

FIG. 45 is a perspective view illustrating a vessel closure device incorporating an embodiment of a pre-tied knot according to the principles of the present invention.

FIG. 47 is a perspective view of a suturing device including a suture cutting blade positioned on the device.

FIG. 48 is a cross-sectional perspective view of the housing of the suturing device of FIG. 47 showing one embodiment of a suture cutting blade.

DETAILED DESCRIPTION

Several embodiments of suturing device that delivers a pre-tied knot to a puncture or incision in a wall of tissue is disclosed. Various aspects of such a device include a length of suture having a bight between first and second ends of the suture. The bight includes one or more loops of suture that form a pre-tied knot when one or more ends of the suture are advanced through the bight. The bight of suture may be pre-arranged in any of several configurations on the device.

Figure 1:
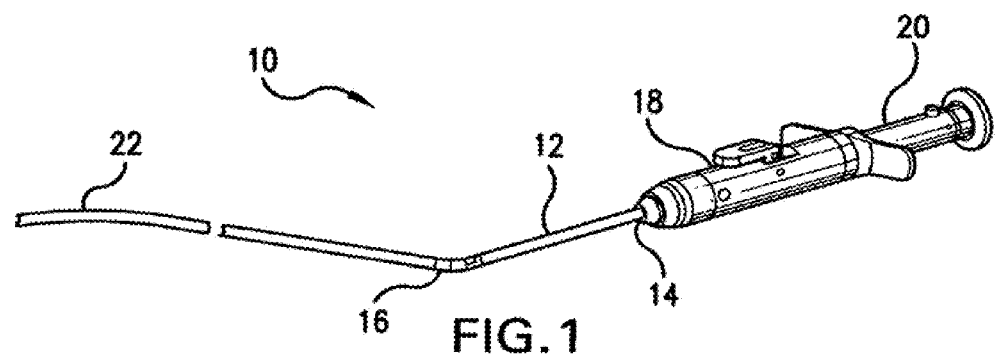
FIG. 1 is a perspective of a percutaneous blood vessel closure device according to the principles of the present invention.

Referring now to FIG. 1, a vessel closure device 10 generally has a shaft 12 having a proximal end 14 and a distal end 16. A proximal housing 18 supports a needle actuation handle 20. A flexible, atraumatic monorail guidebody 22 extends distally of distal end 16 of shaft 12.

Figure 2:
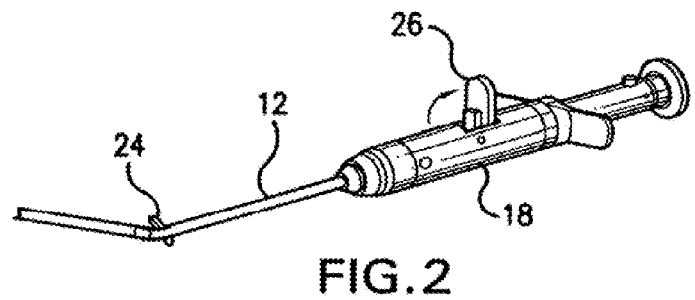
FIG. 2 illustrates the vessel closure device of FIG. 1 in which an elongate foot is shown in a deployed position.

As can be seen with reference to FIG. 2, a foot 24 is articulatably mounted near the distal end of shaft 12. Foot 24 moves between a low profile configuration, in which the foot is substantially aligned along an axis of shaft 12 (as illustrated in FIG. 1), to a deployed position, in which the foot extends laterally from the shaft, upon actuation of a foot actuation handle 26 disposed on proximal housing 18.

Figure 2A:
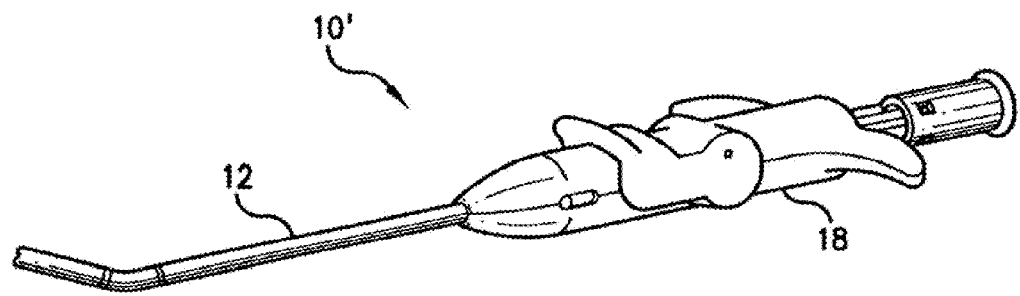
FIGS. 2A-C illustrate actuation of a foot and advancement of needles from a shaft to the articulated foot in a probe similar to the probe of FIG. 1.
Figure 2B:
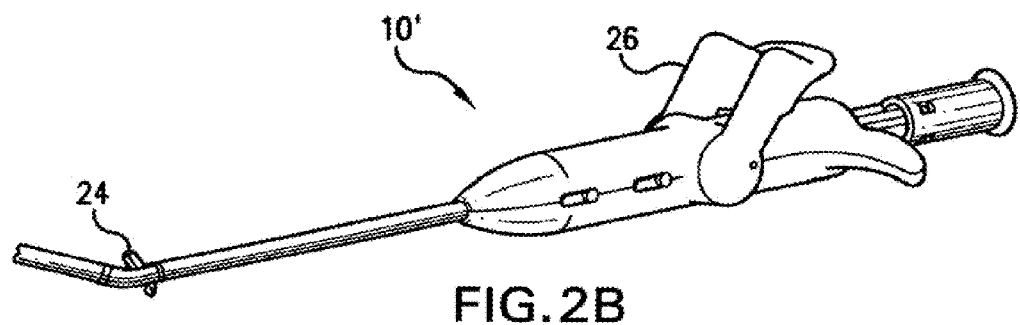
Figure 2C:
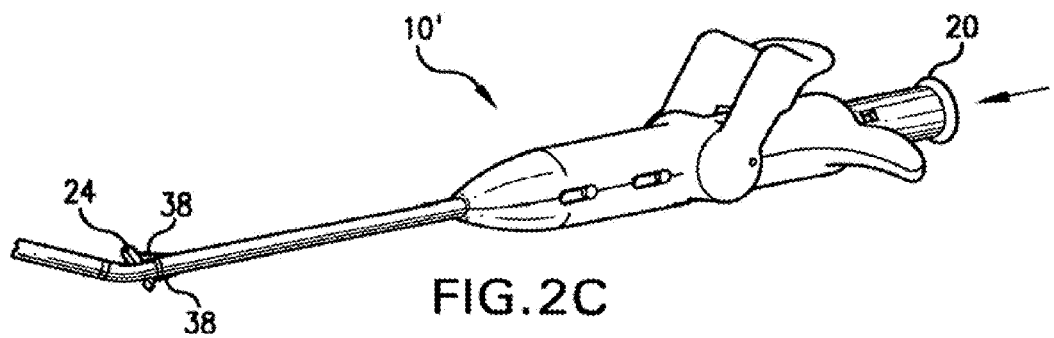

FIGS. 2A through C illustrate the structure and actuation of foot 24 of a preferred probe 10' having a modified proximal housing, and also show how needles 38 can be advanced distally from shaft 12 to the foot by depressing needle actuation handle 20.

Figure 3A:
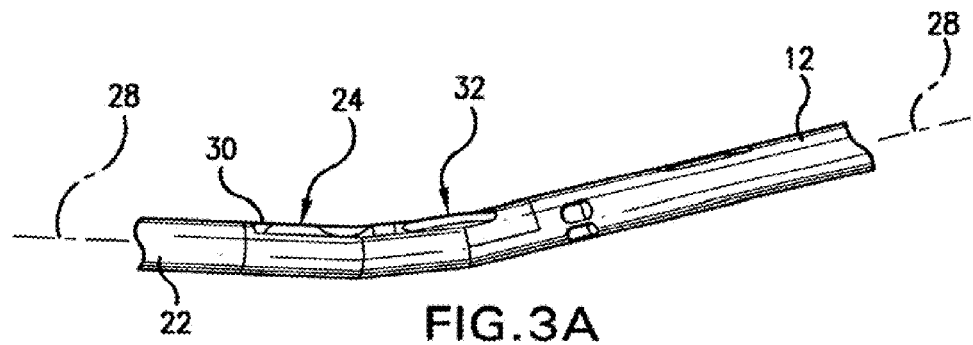
FIG. 3A is a detailed view showing the foot of the vessel closure device of FIG. 1 in a parked position prior to deployment.

Actuation of foot 24 is illustrated more clearly in FIGS. 3A and B. In the parked position illustrated in FIG. 3A, foot 24 extends substantially along axis 28 of shaft 12. Note that the axis of the shaft need not be straight, as the shaft may curve somewhat, particularly adjacent the foot. In the exemplary embodiment, foot 24 is substantially disposed within a foot receptacle 30 of shaft 12 so as to minimize the cross-section of the device adjacent the foot prior to deployment. Advantageously, prior to deployment of the foot, device 10 can have a cross-section adjacent foot 24 of about 7 Fr or less, ideally having a cross-section of about 6 Fr or less for the entire device distally of the proximal end 14 of shaft 12.

Figure 3B:
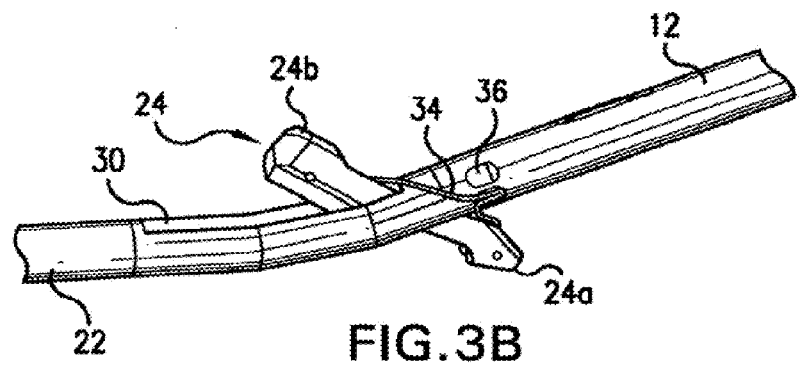
FIG. 3B is a detailed view showing the foot of the vessel closure device of FIG. 1 in a deployed position.

Actuation of foot handle 26 slides a foot actuation wire 32 proximally, pulling foot 24 from a parked position to the deployed position illustrated in FIG. 3B. Once deployed, a first end 24a and a second end 24b of foot 24 extend laterally from the shaft. Suture 34 here comprises a continuous filament with ends disposed in needle receptacles adjacent each end of the foot. An intermediate portion of suture 34 may extend proximally along a suture lumen of shaft 12 to and/or beyond proximal housing 18. Alternatively, in preferred probe 10', the length of suture between the ends may extend distally within flexible guidebody 22, preferably in a dedicated lumen (separate from the monorail guidewire lumen). In still further alternatives described below, a short length of suture or some other flexible filament may extend substantially directly between the needle receptacles.

Shaft 12 also includes a foot position verification lumen that extends distally from a position verification port 36 to a position indicator at housing 18. When the foot is properly positioned within the blood vessel, blood pressure will cause blood to flow proximally through the indicator lumen to the indicator. The indicator may optionally comprise a blood exit port, a clear receptacle in which blood is visible, or the like. In the exemplary embodiment, the indicator of handle 18 comprises a length of clear tubing extending from housing 18 (not shown) in which the blood is clearly visible. It should be understood that a wide variety of alternative position verifications sensors might be used, including electrical pressure sensors, electrolytic fluid detectors, or the like.

Figure 4:
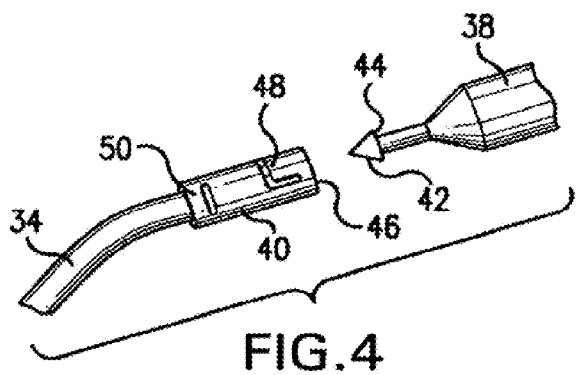
FIGS. 4 and 4A are perspective views illustrating a suture attachment cuff and an associated barbed needle for use in the vessel closure device of FIG. 1.
Figure 4A:
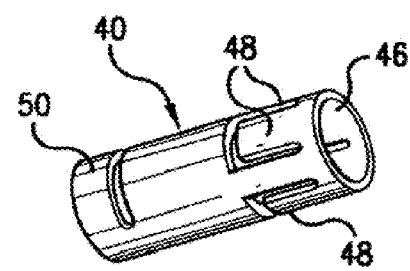
Figure 5:
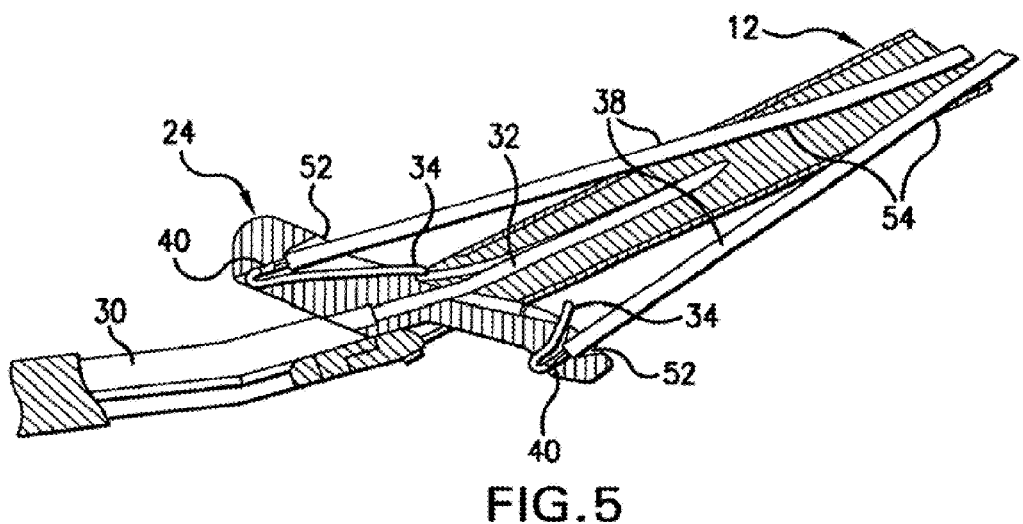
FIG. 5 is a cross-sectional view showing the barbed needles securingly engaging the suture cuffs of the deployed foot.

The structures used in positioning a loop of suture across the puncture can be understood with reference to FIGS. 4, 4A, and 5. In general terms, needles 38 extend from shaft 12 into secured engagement with fittings 40 attached to sutures 34. More specifically, needles 38 include a barbed end 42 defining a recessed engagement surface 44. Fittings 40 are roughly cylindrical structures having an axial channel 46 which receives barbed end 44 of needle 38 therein. A first slot is cut in fitting 44 so as to define at least one tab 48. Tabs 48 can be resiliently biased inward into channel 46. As needle 38 advances into fitting 40, barbed end 42 resiliently displaces tab 48 clear of channel 46 so as to allow the barbed end to pass axially into the fitting. Once barbed end 42 is disposed axially beyond tab 48, the tab resiliently flexes back into the channel, capturing needle 38 by engagement between the tab and recessed surface 44. As each tab can hold the fitting in place on the needle, the use of more than one tab increases the reliability of the system. Ideally, three tabs are provided, as illustrated in FIG. 4A.

To facilitate attachment of fitting 40 to suture 34, a second slot cut in the tubular fitting structure defines a suture attachment collar 50. Optionally, collar 50 may be crimped about suture 34 to mechanically affix the suture to fitting 40. In addition and/or instead of mechanical crimping, suture 34 may be bonded to fitting 40 using an adhesive, heat, fasteners, knots, or the like.

Fitting 40 is quite small in size, and is generally configured to facilitate withdrawing the fitting (and the attached suture) along with needle 38 axially through the vessel wall along the needle path. Needle 38 will generally have a cross-sectional width of between about 0.010 inches and 0.020 inches. Barb 42 will extend laterally so as to define an engagement surface 44 having a protruding length of between about 0.002 inches and 0.005 inches. Fitting 40 will preferably have a cross-sectional size roughly corresponding to or only slightly larger than needle 38. Fitting 40 will typically have an outer lateral width of between about 0.014 inches and 0.025 inches, and an axial length of between about 0.035 inches and 0.050 inches. Channel 46 will be sized to receive at least a portion of needle 38, and will generally have a width of between about 0.010 inches and 0.020 inches. Suture 34 will preferably extend axially opposite the open end of channel 46 so as to minimize drag when the suture is drawn proximally along the needle path. In the exemplary embodiment, needle 38 has a diameter of about 0.020 inches, while the fitting comprises a tube having an outer diameter of about 0.020 inches, an inner diameter of about 0.016 inches, and an overall length of about 0.047 inches. The fitting will typically comprise a resilient material, preferably comprising a metal, and in the exemplary embodiment, comprising stainless steel.

Needles 38 typically have a length of between about 5.0 inches and 6.0 inches, and will preferably be sufficiently stiff to be advanced in compression through the vessel wall (and adjacent tissues) for up to 0.5 inches when supported in cantilever. Nonetheless, the needles will ideally be flexible enough to be laterally deflected within shaft 12, as can be understood with reference to FIG. 5. Needles 38 generally comprise a high strength metal, ideally comprising stainless steel. Fittings 40 will also preferably comprise a flexible material to allow tab 48 to flex out of the way of barbed end 42, and to resiliently rebound and engage recessed surface 44. In the exemplary embodiment, barbed end 42 has a diameter of about 0.015 inches, with the diameter of the needle decreasing to about 0.008 inches proximally of the barb so as to define the recessed engagement surface.

As was generally described above, foot 24 includes needle receptacles 52 adjacent the ends of the foot. A fitting 40 (with an associated end of suture 34) is disposed within each needle receptacle, and a surface of the receptacle tapers proximally and outwardly so as to guide the advancing needles 38 into engagement with fittings 40 when foot 24 is in the deployed position. As fittings 40 (and associated portions of suture 34) are releasably supported in the foot, needles 38 can be withdrawn proximally so as to draw the fittings and suture ends from the foot proximally into (and optionally through) shaft 12. The needle receptacles of the exemplary embodiment taper outward at an angle between 20 and 35 degrees from the centerline of fitting 40, and the fitting is held in a recess having a diameter of about 0.0230 inches and a length of about 0.042 inches. A lateral opening or window through the side of foot to the fitting recess may be provided to facilitate needle and/or cuff positioning during assembly of the probe, and a protruding collar near the proximal end of the fitting recess may help keep the fitting in position.

FIG. 5 also illustrates the lateral deflection of needles 38 by needle guides 54 of shaft 12. This lateral deflection of the needles allows the use of a small diameter shaft, while still encompassing sufficient tissue within the suture loop on opposite sides of the puncture so as to effect hemostasis when the suture looped is tightened and secured. In the exemplary embodiment, shaft 12 comprises an outer casing of a biocompatible material such as stainless steel, carbon fiber, nylon, another suitable polymer, or the like. Needle guides 54 may be defined at least in part as lumens formed within the casing of a polymeric material such as nylon or the like. In some embodiments, shaft 12 may comprise a carbon fiber filled nylon, or carbon fiber filled with an alternative material.

Figure 6A:
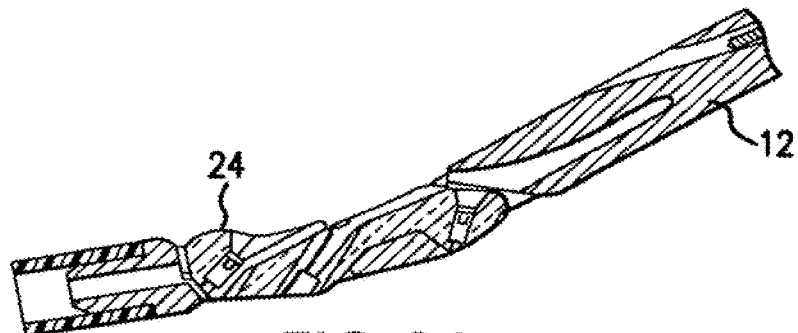
FIGS. 6A-C illustrate one embodiment of a deployable foot, in which the foot slides and pivots when drawn proximally by a tension member.
Figure 6B:
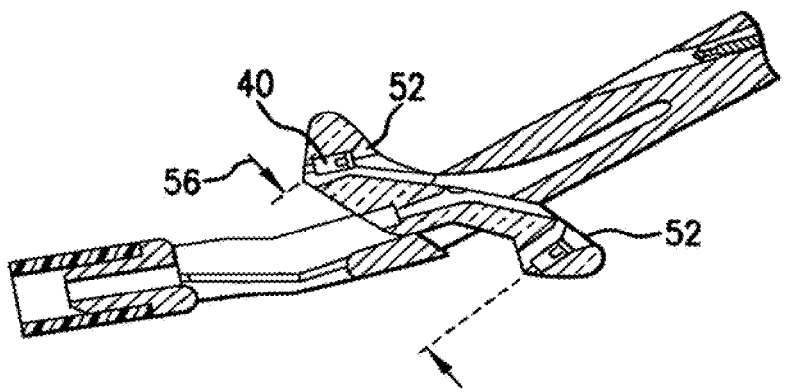
Figure 6C:
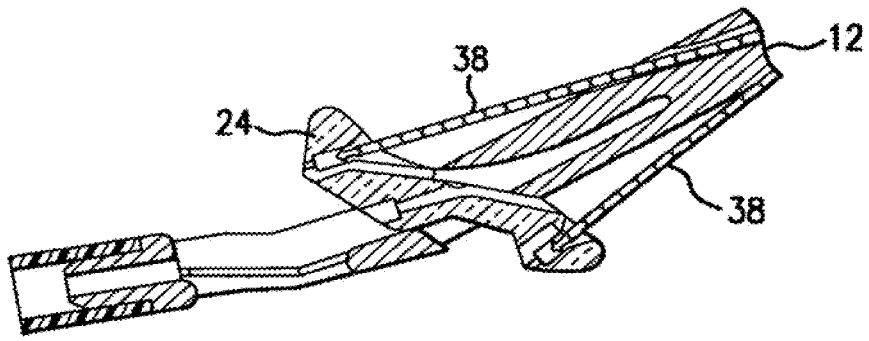

One example of a suitable structure and articulation motion for foot 24 is illustrated in FIGS. 6A and B. Foot actuation wire 32 (see FIG. 3A) rides in a lumen of shaft 12, and draws foot 24 from a parked position (shown in FIG. 6A) to a deployed position (shown in FIG. 6B) through a combination of sliding and pivoting of the foot. The foot remains supported throughout its range of motion by arms disposed laterally on either side of the foot, the arms defining (at least in part) foot receptacle 30. Once foot 24 is deployed, needle receptacles 52 and/or the fittings disposed therein will preferably define a lateral suturing width 56 in a range from about 0.260 inches to about 0.300 inches. Foot 24 may be machined or cast from a polymer or metal, but will preferably comprise a polymer such as carbon fiber filled nylon. In some cases, foot 24 may be molded as two separate halves which can subsequently be affixed together. Needles 38 advance from the fixed needle guides 54, and are laterally directed into fittings 40 by receptacles 52, as illustrated in FIG. 6C. In general, a shape memory alloy such as Nitinol® in its superelastic regime provides a particularly advantageous actuator wire for manipulating foot 24.

Figure 7:
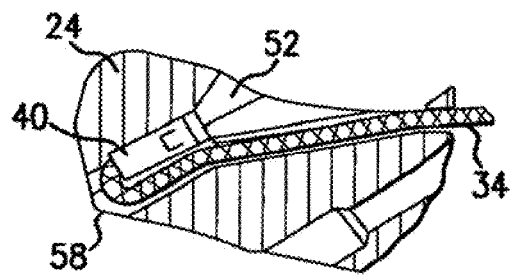
FIG. 7 illustrates the suture cuff positioned within a needle receptacle, and also shows how the suture is releasably secured within a slot extending radially from the needle receptacle.

Referring now to FIG. 7, fittings 40 and suture 34 will be withdrawn proximally by the needles from needle receptacles 52. To releasably support fittings 40 and suture 34 and avoid entanglement of the suture in the needles, suture 34 is fittingly received within a slot 58 which extends laterally from needle receptacles 52. As the needles pull the fitting axially from needle receptacles 52, suture 34 is pulled from slot 58 and free from foot 24. Bending of the suture proximally within the suture slot can also locally increase the suture width, so that the interaction between the bent suture and the slot can help hold the fitting in the recess.

Figure 8A:
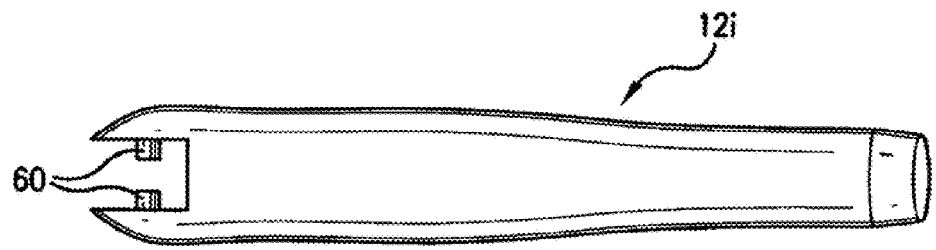
FIGS. 8A-C illustrate an alternative foot articulation mechanism in which lateral slots on the foot receive pins from the shaft to allow the foot to pivot and slide axially.
Figure 8B:
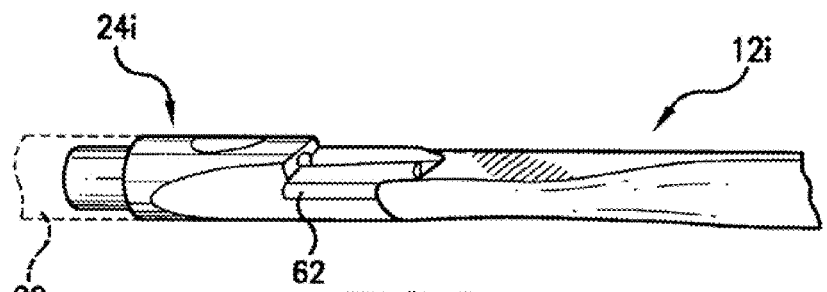
Figure 8C:
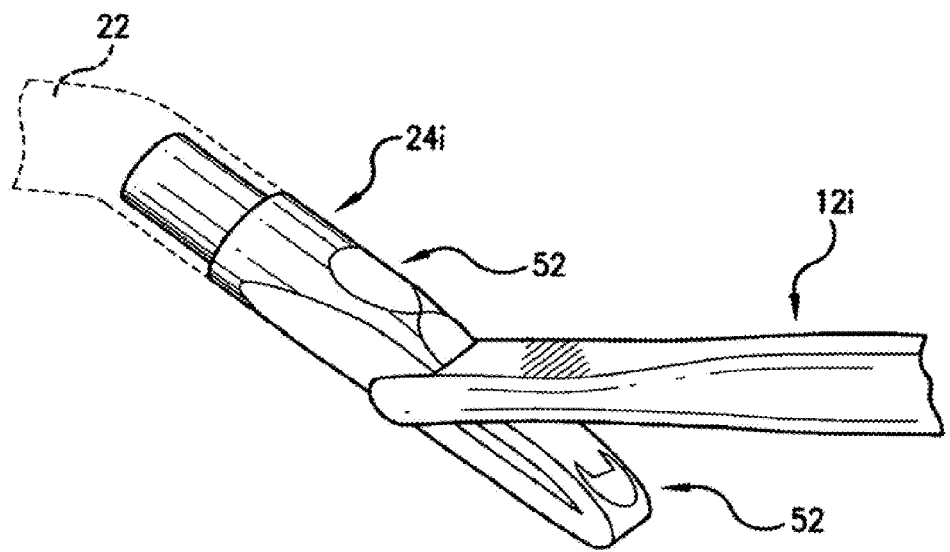

A wide variety of foot actuation mechanisms might be used within the scope of the present invention. A first alternative foot actuation arrangement is illustrated in FIGS. 8A-C. In this embodiment, a shaft 12i has pins 60 which ride in associated slots 62 of a foot 24i. Proximal motion of an actuation wire causes foot 24i to move axially and rotationally, with pins 60 sliding along slot 62, and the foot pivoting about the pins. In this embodiment, guidebody 22 extends directly from the foot, as illustrated in FIG. 8C.

Figure 9A:
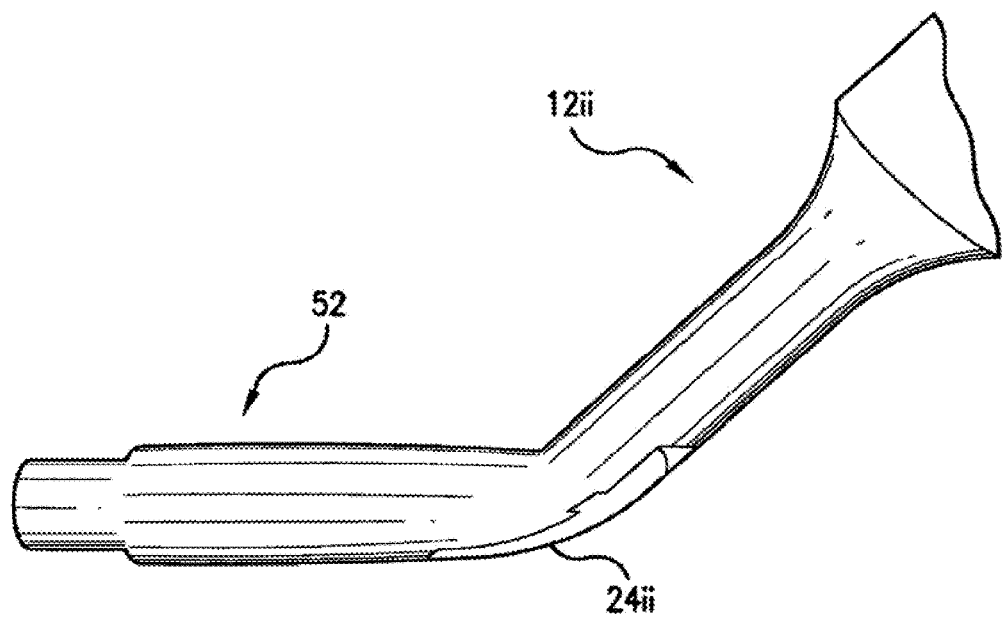
FIGS. 9A and B illustrate a still further alternative foot actuation mechanism in which the foot slides axially within a slot.
Figure 9B:
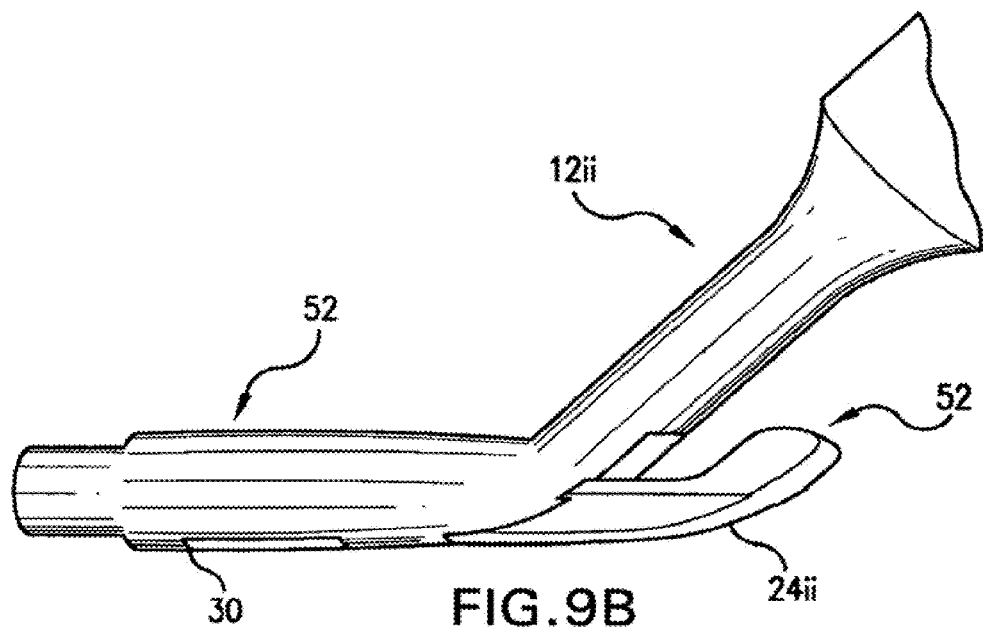
FIGS. 9C and D illustrate a further foot actuation mechanism in which relative movement between the sides of a two-part shaft actuates the foot.

A still further alternative foot actuation mechanism is illustrated in FIGS. 9A and B. In this embodiment, slidable foot 24ii is slidingly received within a receptacle 30 of shaft 12ii. Sliding of the foot 24ii from the parked position of FIG. 9A to the deployed position of FIG. 9B places the needle receptacles 52 in the paths of needles from the shaft 12ii without pivoting of the foot. Guidebody 22 (see FIG. 1) will extend here from a distal end of shaft 12ii at a fixed angle from the shaft. Optionally, insertion through the tissue tract may be facilitated by including an additional bend in the shaft axis adjacent the guidebody on many embodiments.

Figure 9C:
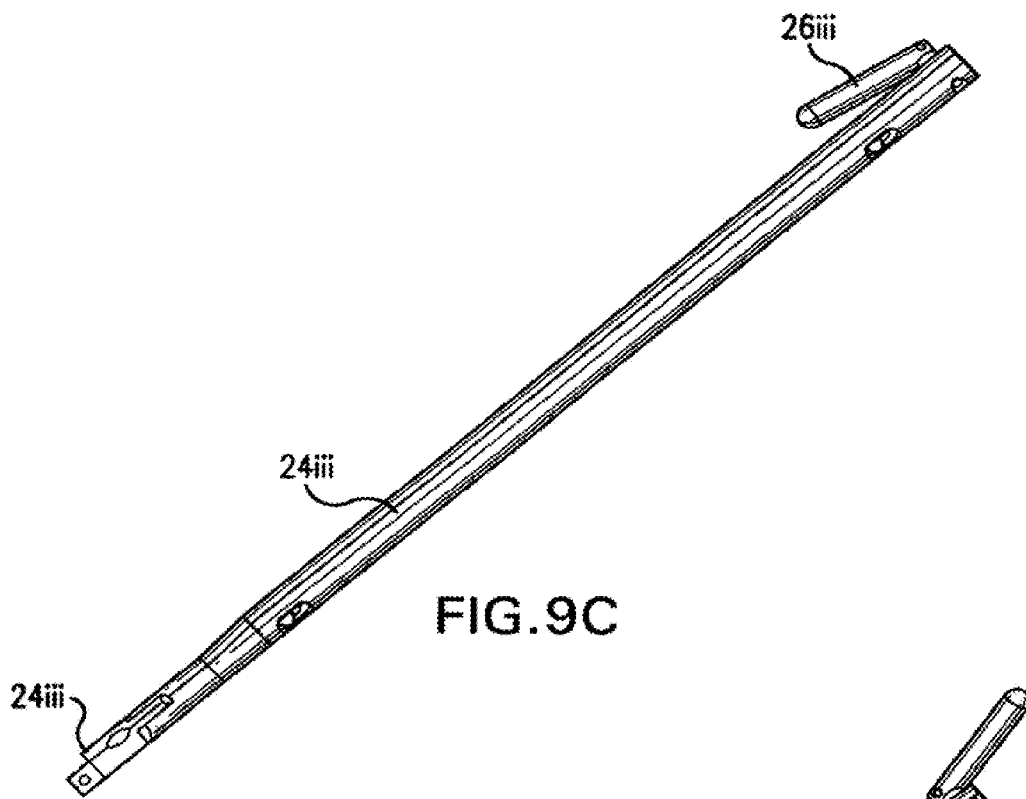
Figure 9D:
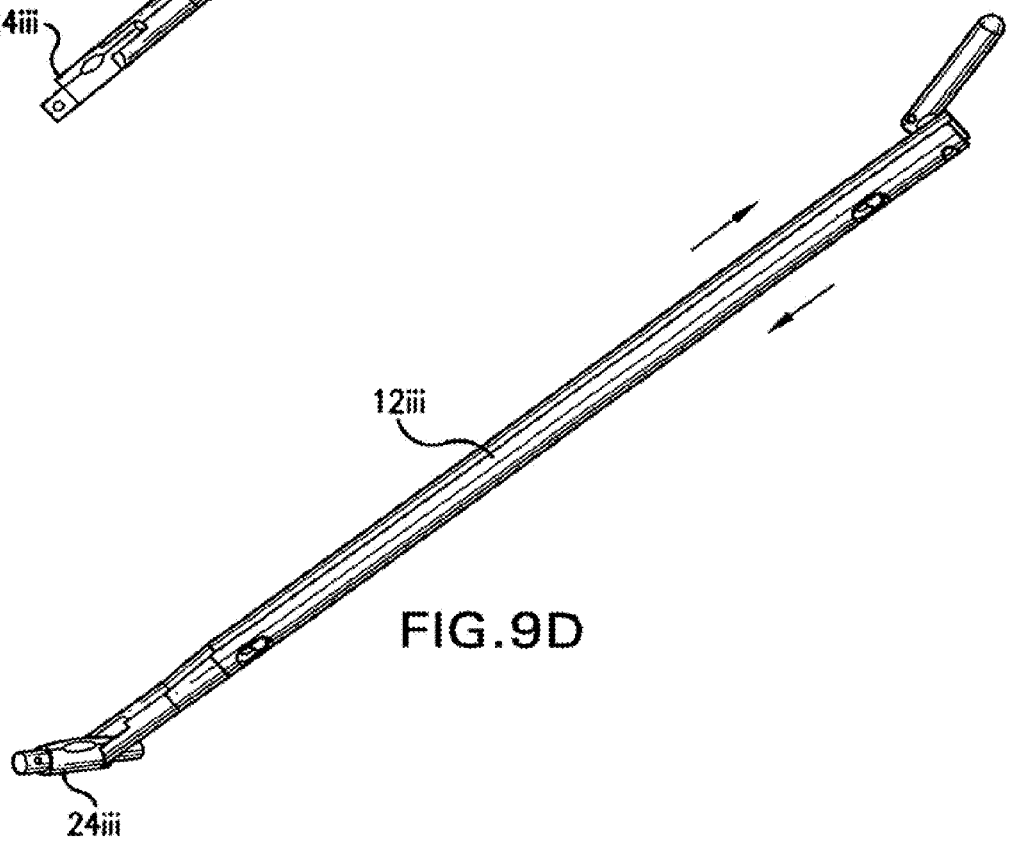

Yet another foot actuation mechanism can be understood with reference to FIGS. 9C and D. Shaft 12iii is formed in two parts, which slide axially relative to each other when foot actuation lever 26iii moves, using an offset crank arrangement. A similar offset crank supports foot 24iii, so that the sliding shaft parts cause the foot to pivot as shown.

Figure 10A:
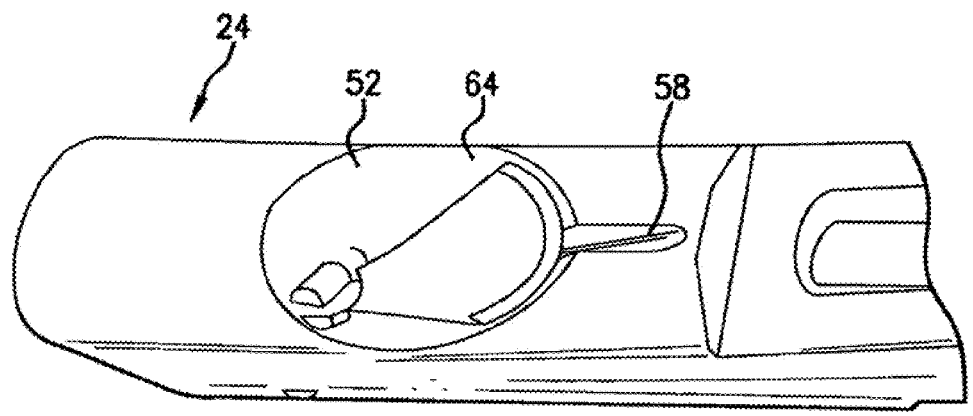
FIGS. 10A-D illustrate alternative structures and techniques for avoiding entanglement of the needle with the suture.

A variety of features may be included in the articulatable foot, the needle receptacle, and/or the needle to avoid tangling of the needle in the suture as the needle is directed to the fitting. As illustrated in FIG. 10A, a moveable flap 64 may extend over slot 58 so that the advancing needle slides along the flap toward the fitting, rather than entering the slot and engaging the suture directly. Flap 64 may be affixed along one side of the slot, with the other side of the flap flexing into the receptacle to release the suture from slot 58 when the fitting and suture are withdrawn by the needle.

Figure 10B:
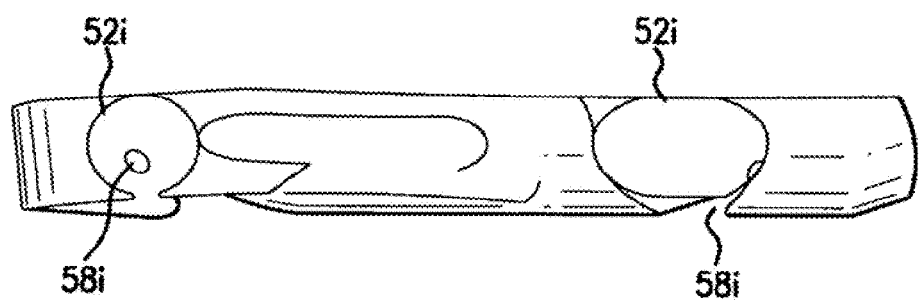

An alternative mechanism for avoiding entanglement of the needle with the suture is illustrated in FIG. 10B. In this embodiment, needle receptacles 52i have tangential slots 58i which extends substantially tangentially to the surface of the receptacle. As a result of this tangential arrangement, a needle entering the receptacle 52i will be directed toward the fitting contained therein, but will generally not be able to enter and advance within the tangential slot 58*i* so as to become entangled with the suture. As illustrated in this embodiment, the slots may optionally extend laterally through the foot so that the loop of suture can be pulled from one side of the shaft without interference.

Figure 10C:
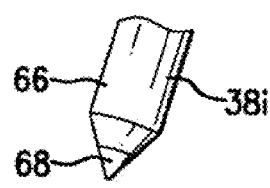
Figure 10D:
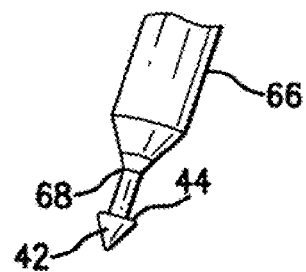

A still further alternative mechanism for avoiding entanglement between the suture and the needle is illustrated in FIGS. 10C and D. Two-part needle 38*i* includes an outer sheath 66 and an inner core 68. The parts of these needles initially advance together into the receptacles with the needle core 68 withdrawn so that the needle presents a smooth tapered tip (the combined tip preferably being larger in diameter than the slot containing the suture) as illustrated in FIG. 10C. Once two-part needle 38*i* is fully positioned within the needle receptacle, needle core 68 may extend axially to expose barbed tip 42 and recessed engagement surface 44 and to secure the needle to the fitting within the needle receptacle. In the exemplary embodiment of FIGS. 4 and 5, barbed tip 42 is formed integrally with the rest of the needle structure, but the tip has a larger cross-section than radial slot 58 containing the suture 34. As a result, the barbed tip is unable to enter the slot, thereby avoiding entanglement between the needle and suture.

An alternative vessel closure probe 70 will be explained with reference to FIGS. 11A through 11E. This embodiment includes an articulatable foot 24 having a pair of needle receptacles 52, as described above. Although each needle receptacle 52 contains a fitting 40 for coupling a flexible connecting filament 74 to a tip of an associated needle, the connecting filament 74 in this case comprises some temporary connecting filament, as shown schematically in phantom in FIG. 11A. The connecting filament spans directly between the needle receptacles. Rather than pulling the two ends of an extended loop through the needle paths and proximally out the tissue tract for tying, closure system 70 advances a single end of the suture distally along one needle path, across the puncture, and then proximally along the other needle path. To provide this interaction, at least one needle includes means for attaching suture 34 to connecting filament 74, here in the form of a detachable coupling structure carried on the at least one needle. This structure facilitates the use of a pre-tied knot.

Referring now to FIGS. 11A and B, the distal end of probe 70 advances distally through skin S and into a tissue T of the patient while the probe is in the small profile configuration with foot 24 aligned along the axis of the probe. Here, however, an end 76 of suture 34 is affixed to a detachable needle tip 78 of a hollow needle 38'. Detachable tip 78 comprises a fitting having an opening receiving an end of suture similar to fitting 40, attached to a barbed needle end (similar to that of needle 38). Suture 34 may extend proximally within hollow needle 38 where the needle has an open channel along its length, may exit the hollow needle just proximally of detachable tip 78, or may be disposed alongside a solid needle. Needle 38 (opposite hollow needle 38') has a fixed barbed tip, as described above, and a bight of suture 80 is releasably attached to the probe shaft encircling the opening of needle guide 54 of the fixed tip needle. The bight of suture may be releasably disposed within a slot of the probe, may be temporarily held in place by a weak adhesive or coating, or the like. A second end 82 of suture 34 extends proximally along the shaft of the probe, the second end of the suture optionally also being releasably held along the shaft.

Bight 80 will define a knot when first end suture passes therethrough, as can be understood with reference to FIGS. 11Ai and 11Aii. Bight 80 will often include more than one loop, and may be pre-arranged so as to define a square knot (using the layout schematically illustrated in FIG. 11Ai), a clinch knot (FIG. 11Aii), or a variety of known or new surgical knots.

Probe 70 advances along tissue tract TT to puncture P in blood vessel V. Once foot 24 is disposed within a blood vessel V, a pull wire moves the foot proximally and pivots the foot laterally so that the foot extends along an axis A of the vessel, as illustrated in FIG. 11B. The foot can then be pulled proximally against an inner surface of the vessel wall W to ensure that the needle receptacles 52 are properly positioned.

Figure 11C:
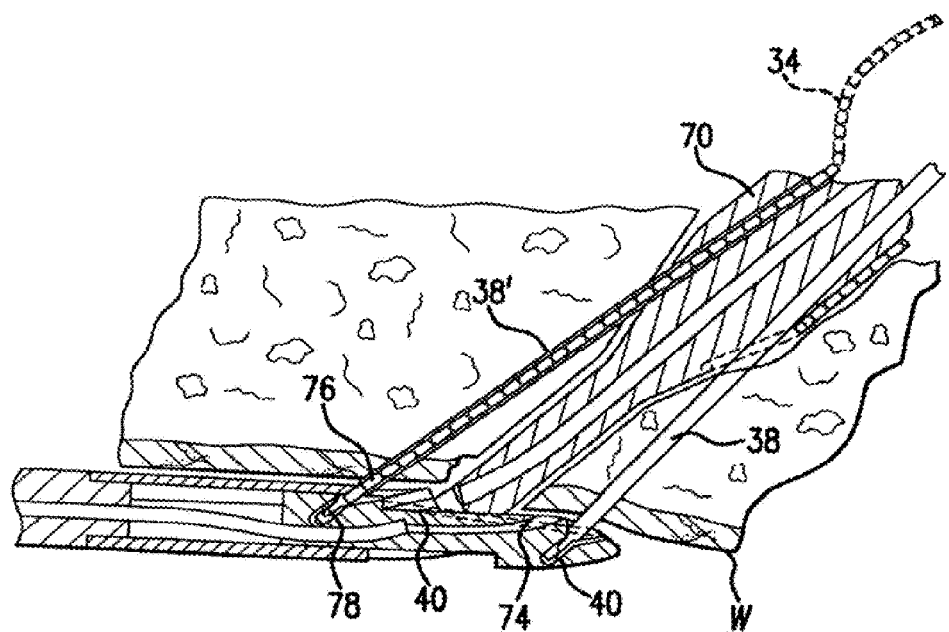

As can be understood with reference to FIGS. 11C and D, hollow needle 38' and needle 38 advance to engage fittings 40 within receptacles 52. Hollow needle 38' draws first end 76 of suture 34 distally through vessel wall W, and detachable tip 78 is secured into an associated fitting 40 using the barb and tab interaction described above. As connecting filament 74 extends between fittings 40, and as detachable tip 78 can pull free of hollow needle 38' when the needles are withdrawn, this effectively couples needle 38 to first end 76 of suture 34. The detachable tip riding partially within the hollow needle (or vice versa) so that the assembly remains together under compression. Hence, needle 38 can pull the suture distally along the needle path formed by hollow needle 38', across the puncture P, and proximally along the needle path formed by needle 38, as illustrated in FIG. 11D.

Figure 11D:
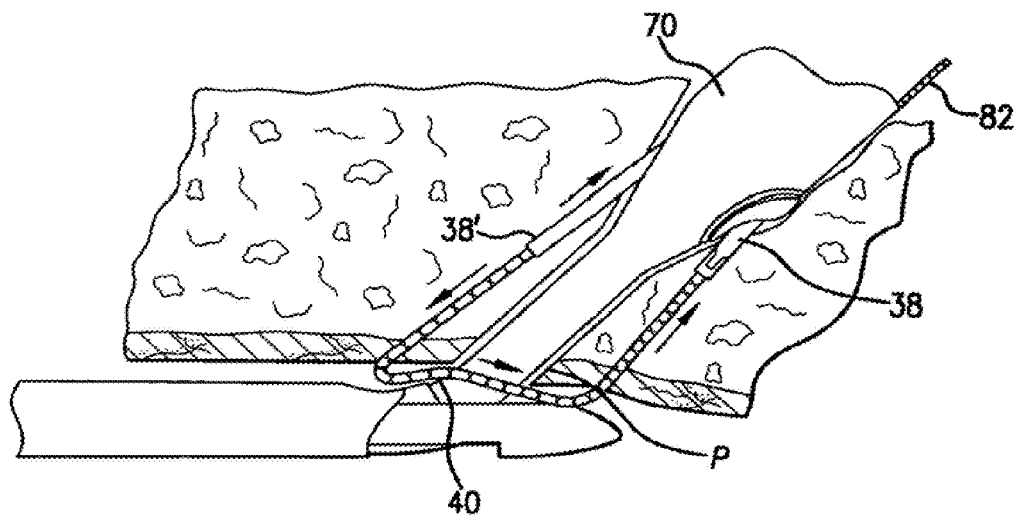
Figure 11E:
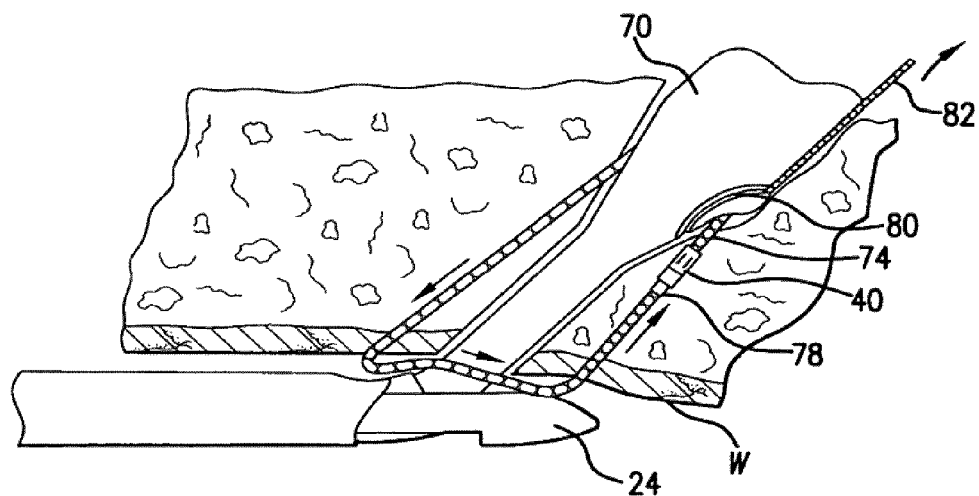

FIGS. 11D and E show that the knot can be completed by pulling needle 38, connecting filament 74, and second end 76 of suture 34 (together with the fittings 40 and detachable needle tip 78) proximally through bight 80. Second end 82 of suture 34 can be pulled to free bight 80, and the ends of the suture can be tightened and the probe removed to provide permanent hemostasis.

It will be recognized that removal of probe 70 can be facilitated by coupling first end 76 to bight 80 over an outer surface of the probe, and by arranging suture 34 and hollow needle 38' so that the suture can pull free of the needle when detachable tip 78 is released, for example, by having the suture exit the needle proximally of the tip through a channel that extends to the tip so that the needle does not encircle the suture. By including such provisions, after foot 24 is returned to the narrow configuration, the probe can be pulled proximally from the tissue tract leaving the pre-tied knot in place.

Alternative arrangements (using the detachable needle ends of probe 70) are possible to provide the benefit of a pre-tied knot and the like for closure of a vessel puncture. For example, a probe having a pair of needles in which each needle included a detachable tip might be used to pull first end 76 through a bight, so that the bight need not encircle the needle path of one of the needles.

Figure 12A:
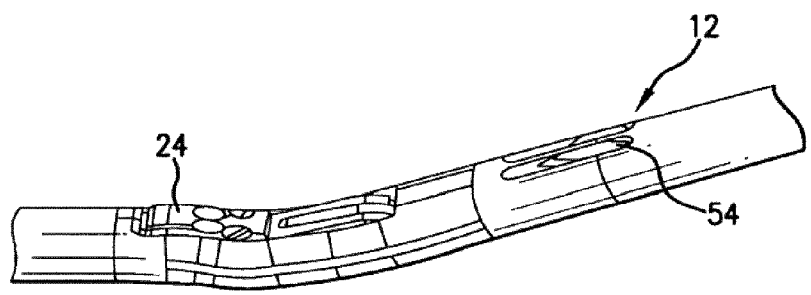
FIGS. 12A and B illustrate an alternative probe having two pairs of needles and a foot with four needle receptacles so as to form two loops of suture across a puncture of a blood vessel.
Figure 12B:
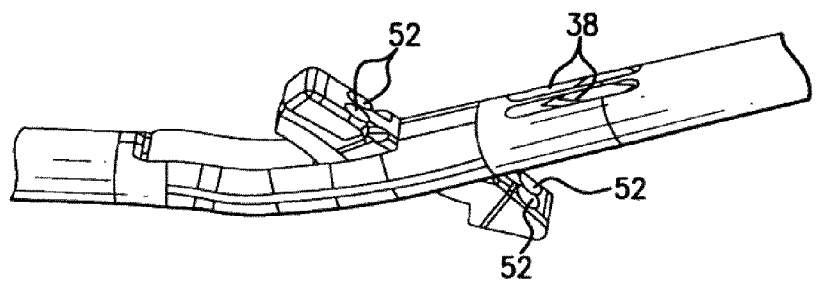

In some cases, particularly for closure of large punctures, it may be advantageous to provide multiple suture loops across the puncture, either in parallel, in an "X" pattern, or the like. As illustrated in FIGS. 12A and B, the present invention encompasses the use of more than two needles and associated receptacles, fittings, sutures, and the like. Multiple loop systems may have four, six, eight, or more needles, or may even have odd numbers of needles and fittings, particularly where one or more fittings have a plurality of suture ends extending therefrom. This allows a wide variety of stitching patterns to be provided by such multiple loop probes.

Figure 13A:
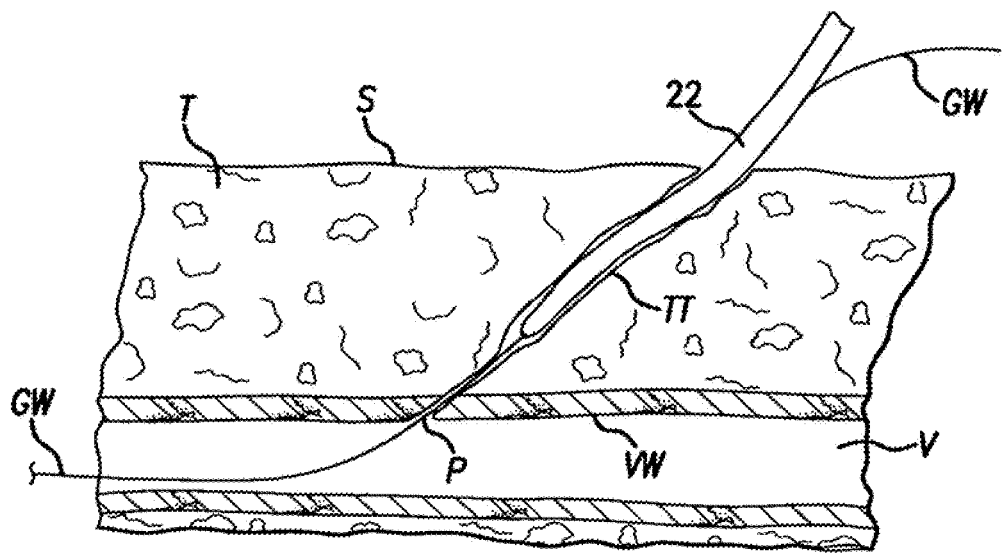
FIGS. 13A-G illustrate a method for use of a suture system so as to effect hemostasis of a blood vessel puncture through a tissue tract.
Figure 13B:
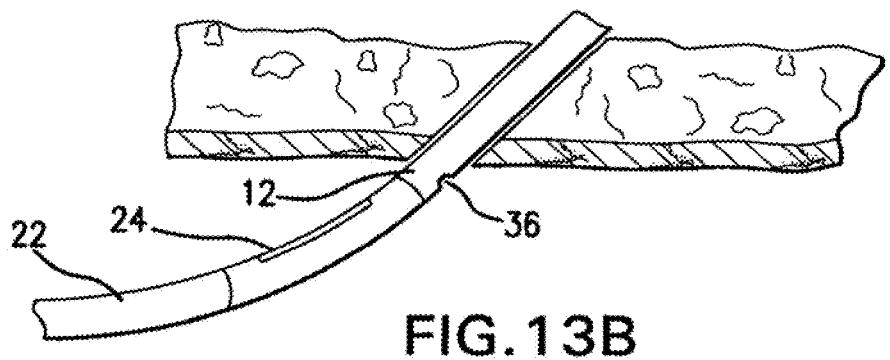

The method of use of the probes of FIGS. 1-7 can be understood with reference to FIGS. 13A-G. After accessing a blood vessel V (often using the Seldinger technique), a guidewire GW is left extending into skin S and down through tissue T along tissue tract TT. Guidewire GW enters vessel V through a puncture P in vessel wall W, and extends along the vessel throughout many endovascular procedures. As illustrated in FIG. 13A, distal guidebody 22 is advanced over the guidewire GW in a monorail fashion, so that the guidewire helps to direct the probe along the tissue tract TT and into the vessel through puncture P. FIG. 13B shows that when sensor 36 is disposed within the vessel, blood can flow from the sensor port and through a lumen in shaft 12 to the proximal handle to notify the operator that foot 24 has been advanced far enough for deployment.

Figure 13C:
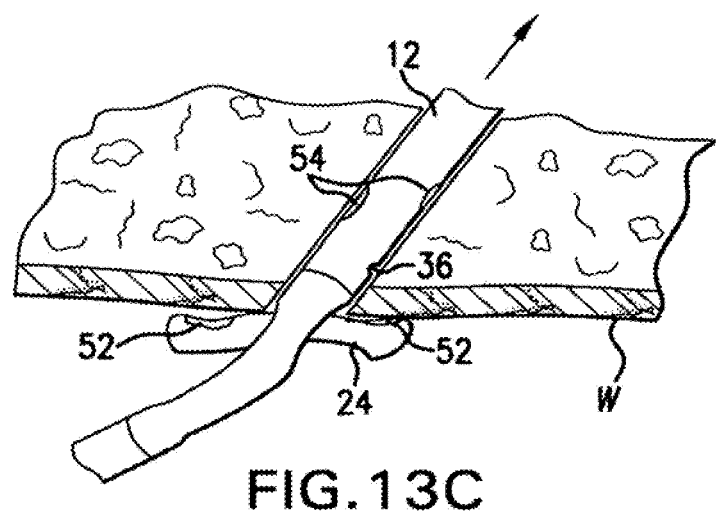

Deployment of the foot is effected by actuation of the foot deployment handle, as described and illustrated above with reference to FIGS. 2 and 2B. As described above, guidebody 22 helps to align the probe with the axis of vessel V. Guidebody 22 may be set at an angle and/or offset relative to shaft 12 as appropriate to aid in alignment with a particular vessel access technique. As shown in FIG. 13C, the deployed foot 24 extends laterally from the shaft, so that foot 24 adjacent receptacles 52 can be drawn up against vessel wall W by gently pulling shaft 12. Hence, the foot helps to accurately position the needle guides 54 at a distance from the vessel wall.

Figure 13D:
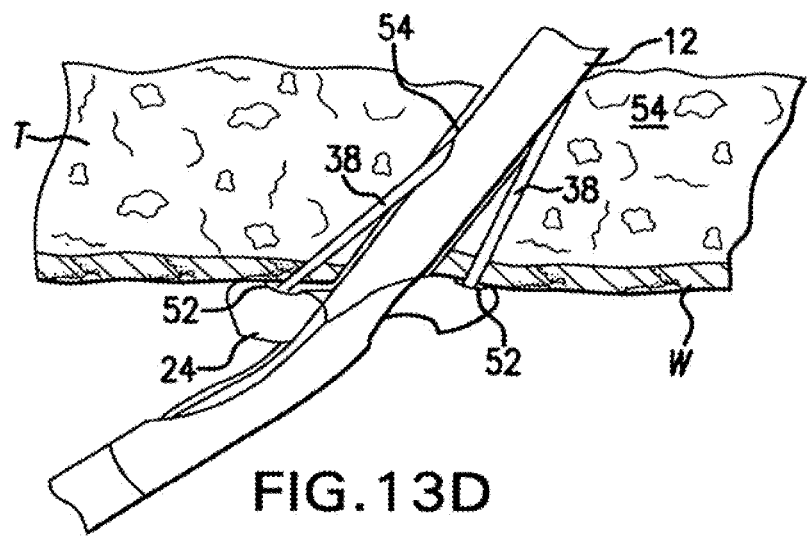

Referring now to FIG. 13D, flexible needles 38 are deflected laterally by needle guides 54 toward receptacles 52 of the deployed foot. As a result, the needles advance in cantilever both distally and laterally when needle actuation handle 20 is pressed (see FIG. 2C), and the tapering surfaces of receptacles 52 help to push the needles back into alignment with the fittings so as to overcome any unintended deflection of the needles by tissue T or vessel wall W. This ensures that needles 38 securingly engage fittings 40 within receptacles 52, thereby coupling the ends of suture 34 to the needles. While suture 34 is here illustrated running along the side of shaft 12 outside foot receptacle 30 to a lumen within guidebody 22, it should be understood that the suture loop might instead extend proximally in a lumen of shaft 12, might be routed through the foot and/or foot receptacle, and/or might be stored in a spool adjacent foot 24. Regardless, suture 34 should able to pull free of the probe between its ends to form a continuous loop across puncture P.

Figure 13E:
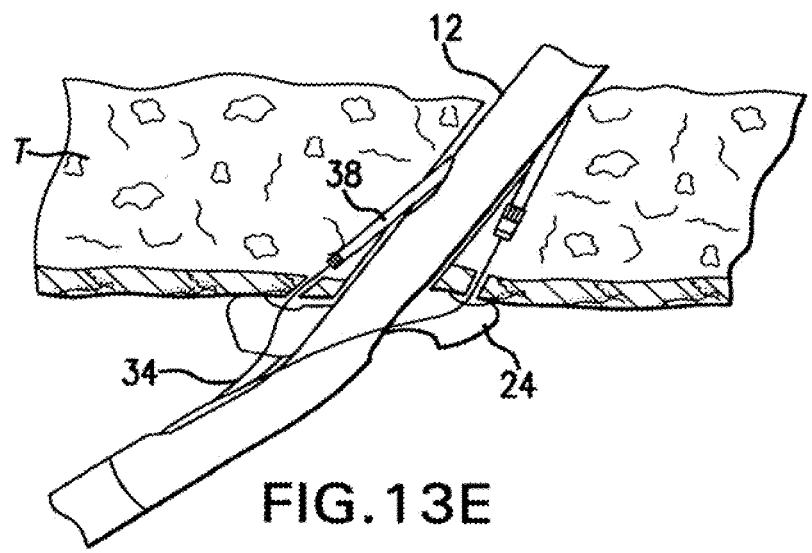
Figure 13F:
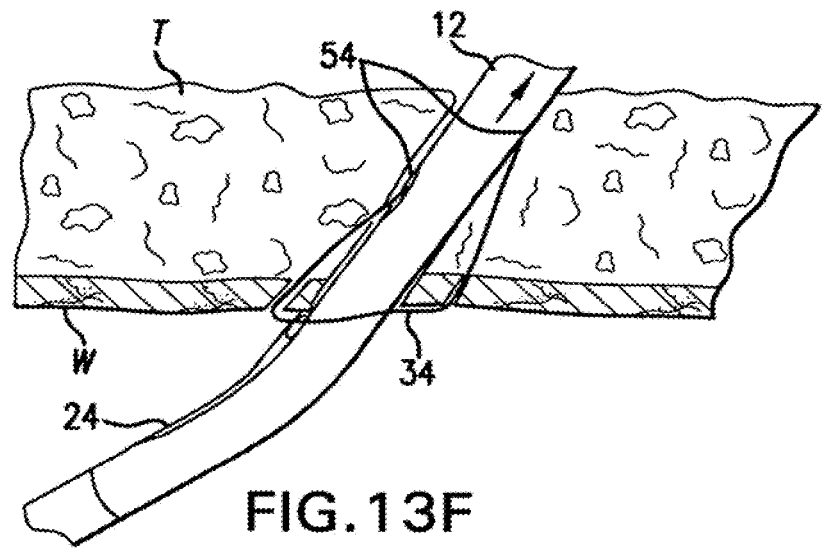

Referring now to FIGS. 13E and F, fittings 40 and the ends of suture 34 are drawn proximally through the vessel wall W along the needle paths formed by needles 38. Optionally, the needles may be withdrawn proximally out of the tissue tract and clear of shaft 12, or they may remain coupled to the shaft within needle guides 54. The foot actuator is moved to store foot 24 along shaft 12, and the shaft can then be pulled proximally from the tissue tract. Guidebody 22, which may comprise a soft, compliant polymer, may temporarily extend at least partially into tissue tract TT and through puncture P to help reduce the loss of blood until the loop is secured.

Figure 13G:
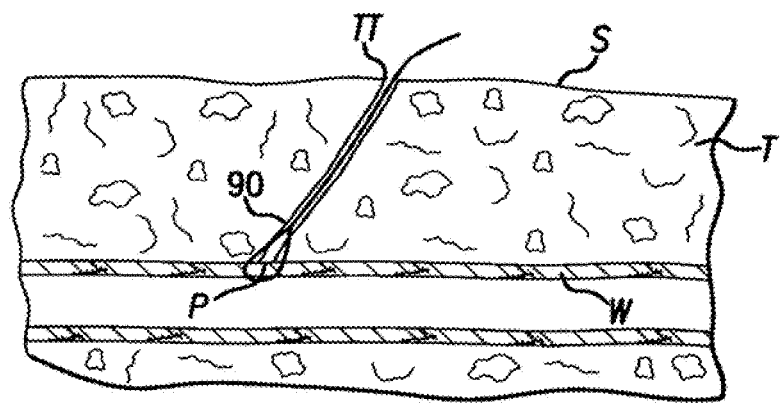

Now referring to FIG. 13G, once shaft 12 has been withdrawn sufficiently to expose needle guides 54, the ends of the suture loop can be grasped by the operator. Tying of a knot in suture 34 can then proceed in a conventional manner. The use of a clinch knot may facilitate gradual tightening of the knot while removing guidebody 22, although a wide variety of knot and knot advancing techniques might be used.

Figure 14A:
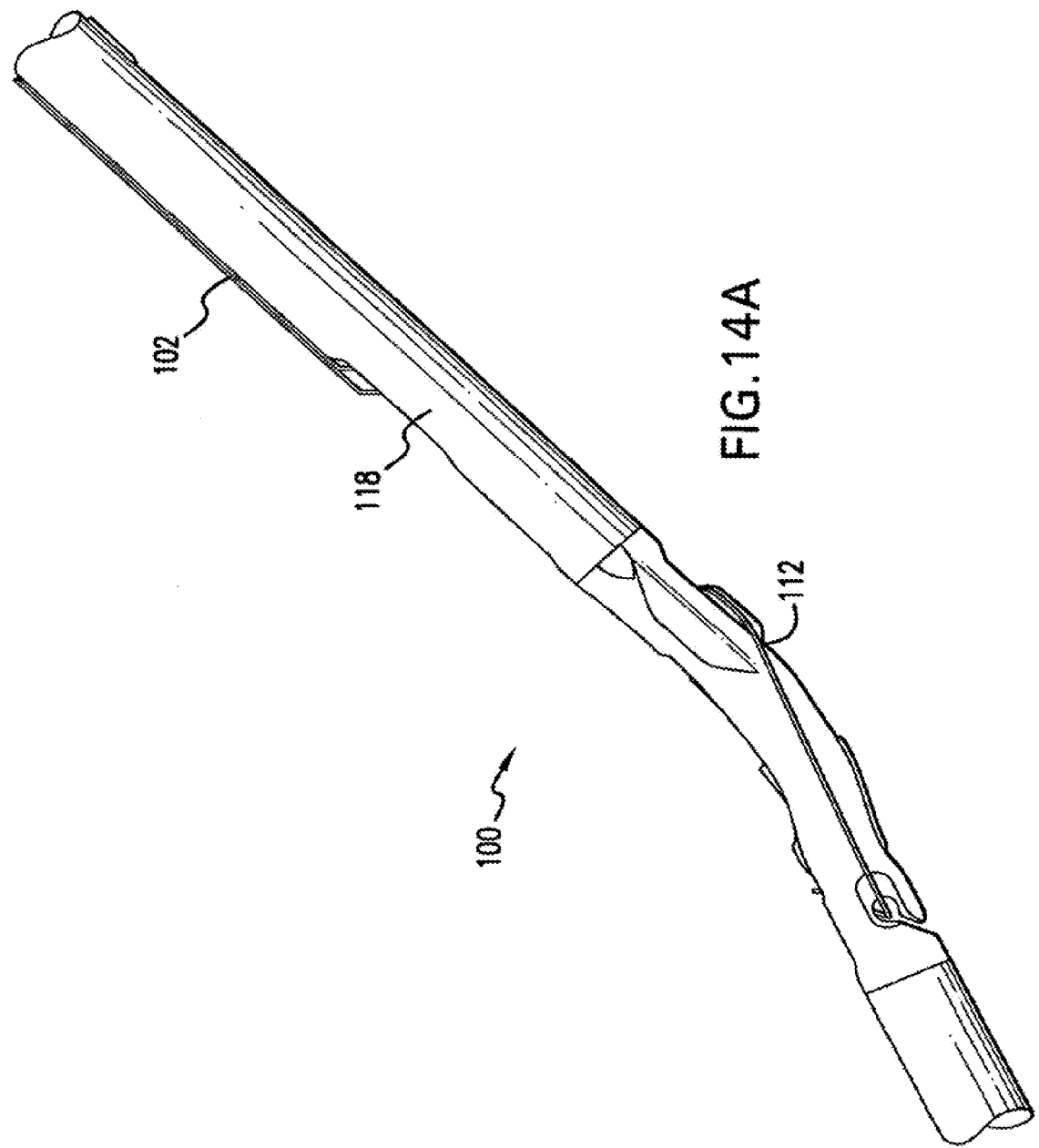
FIGS. 14A and 14B are enlarged partial side views of a suturing device in accordance with one embodiment of the present invention.
Figure 14B:
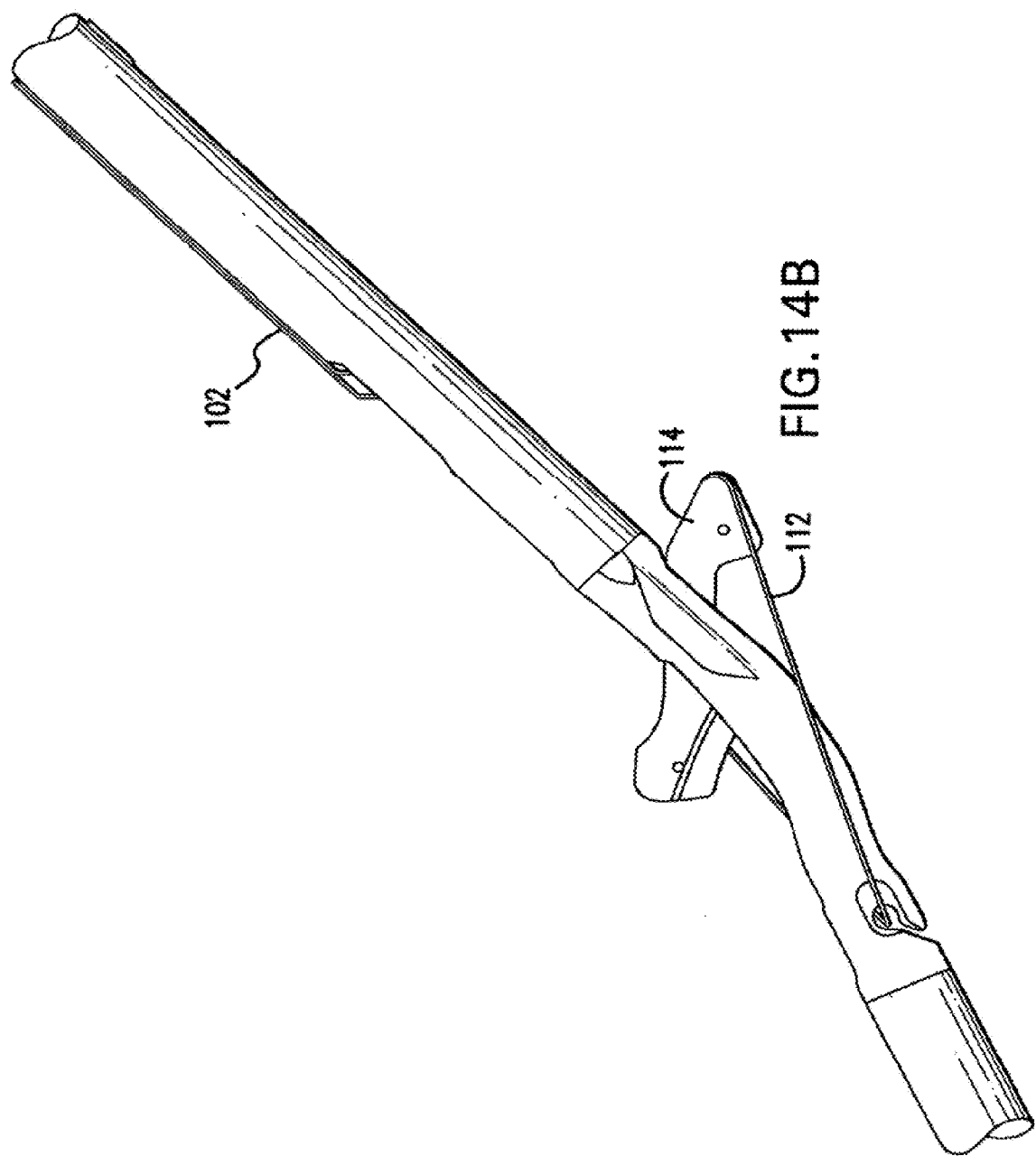

FIGS. 14A and 14B show an embodiment of a vessel closure device 100. This embodiment includes an articulatable foot 114 (FIG. 14B) having a pair of penetrator receptacles (described below). Although each penetrator receptacle contains a fitting (or cuff) for coupling a flexible filament to a tip of an associated penetrator, the filament in this case may be a short length of suture such as a link 112 spanning directly between the penetrator receptacles. Rather than pulling the two ends of an extended loop through the needle paths and proximally out the tissue tract for tying, closure system 100 advances a single end of the suture distally along one needle path, across the puncture, and then proximally along the other needle path. To provide this interaction, at least one needle includes means for attaching suture 102 to the link 112, here in the form of a detachable coupling structure carried on the at least one needle. This structure facilitates the use of a pre-tied knot.

FIG. 15A shows a side, cross-sectional view of the device 100 in a position prior to deployment of the foot 114. The device 100 has been advanced through the incision 105 in the arterial wall W. For ease of description, reference numeral 122 indicates the anterior side of the device, and reference numeral 124 denotes the posterior side of the device. Device 100 has a rigid shaft 118 that has channels defined therein to carry the elongate bodies or penetrators 106 and 106'. Penetrator 106' may also be referred to as the anterior penetrator, and penetrator 106 may be referred to as the posterior penetrator. For purposed of description and not limitation, the anterior penetrator 106' carries the pre-tied knot 104, and posterior penetrator 106 carries the detachable coupling structure or penetrator tip 108. Anterior penetrator 106' defines a penetrator tip 108' at its distal end.

The articulatable foot 114 includes anterior and posterior penetrator receptacles 116' and 116, respectively. These receptacles are also referred to as cuff pockets. Cuffs 110 are shown positioned in cuff pockets 116' and 116. A link 112 extends between the cuffs 110.

Figure 15B:
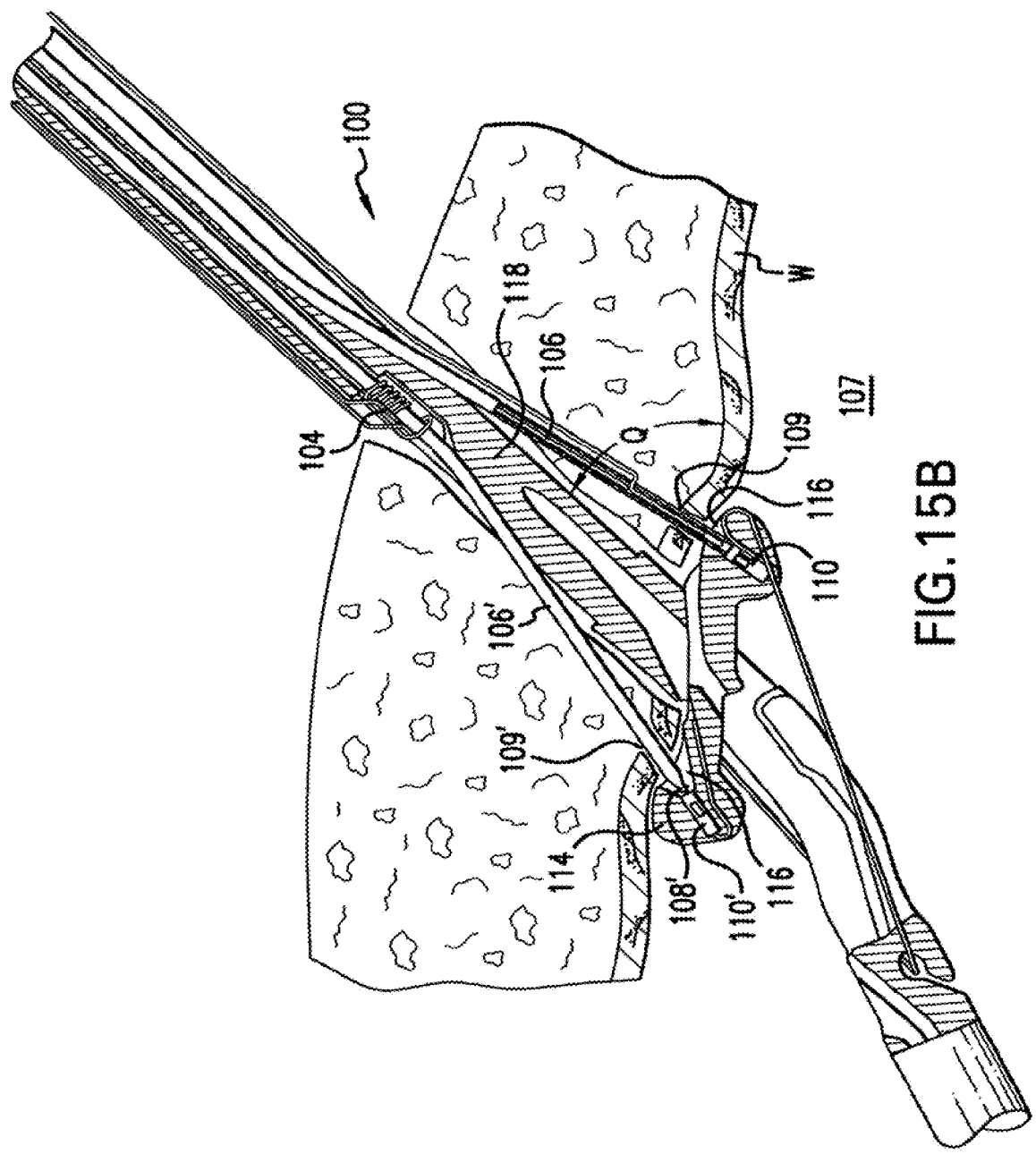

FIG. 15B shows the foot 114 deployed so as to position the cuff pockets 116 to receive the first and second penetrators 106' and 106. As shown in FIG. 15B, the anterior penetrator 106' has the pre-tied knot 104 disposed about a proximal portion of its length. Alternatively, the pre-tied knot 104 may be disposed about the periphery of a knot tube, through which the anterior penetrator 106' may pass (as described in further detail below).

FIG. 15B illustrates the suturing device 100 deployed within a lumen 107 in accordance with an embodiment of the present invention. As may be seen with reference to the Figure, the suturing device 100 includes an elongate body 106' having a penetrator tip 108'. The elongate bodies 106 and 106' deploy to form penetrations 109 and 109' within the vessel wall W. The configuration of the penetrator tip 308 allows penetration of the vessel wall W immediately surrounding the incision 105 to form the penetration 309. As such, the penetration of the penetrator tip 108 through the tissue wall W allows for passage of the elongate body 106 through the tissue and into the lumen 107. The elongate body 106 holds the suture 102 as the elongate body 106 passes through the tissue wall W immediately adjacent the incision 105 and into the foot 114.

As may be seen with reference to FIG. 15B, in this embodiment, the foot 114 has a single unit design where the cuffs 110 and 110' are disposed on opposite sides of the suturing device 100 and the foot 114. This orientation allows balance of forces during the deployment of the elongate bodies 106 and 106', thereby allowing precise suturing and minimizing the possibility of incorrectly suturing the incision 105. Also, as may be seen with reference to the Figure, the suturing device 100 delivers the suture longitudinally relative to the lumen 107, thereby minimizing arterial diameter constriction. Likewise, in this embodiment, the foot 114 is positioned at an angle "Q" relative to the shaft 118 of the suturing device 100. Preferably, the angle "Q" is in a range between about 20 degrees and about 60 degrees and more preferably is about 40 degrees. The angle "Q" approximates the puncture angle commonly used to access the femoral artery. The angle Q and the rigid character of the shaft 118 serve to provide accurate, virtually simultaneous "cuff capture" by both the anterior and posterior penetrators. Moreover, since the device 100 is preferably used without an introducer sheath, the rigid nature of the shaft 118 provides the control of the travel of penetrators as they move distally to engage the cuffs. The device 100 can therefore be used in the same femoral artery access puncture without disturbing the existing tissue tract and causing undue discomfort to the patient.

When both the elongate bodies 106 and 106' and the suture 102 pass through the lumen wall W and into the lumen 107, the elongate bodies 106 and 106' engage with the foot 114. The penetrator tip 108 and anterior penetrator tip 108' of the elongate bodies 106 and 106' engage with cuffs 110 and 110' of the foot 114. The cuffs 110 and 110' include a link 112 that connects the cuffs 110 and 110' to one another. It should be noted that the cuffs 110 and 110' facilitate connection of the penetrator tip 108 with the anterior penetrator tip 108' such that the penetrator tip 108 and the anterior penetrator tip 108' are coupled to one another via the link 112.

FIGS. 16A and 16B show the suture bight in the pre-deployed state (FIG. 16A) and the deployed state (FIG. 16B). The suture 102 is arranged to provide the pre-tied knot 104 that automatically travels down from the shaft of the device where it is stored prior to delivery to the tissue wall. The loop 104 of suture 102 serves to pull the knot 104 down the rail portion 140 of the suture during deployment. It should be noted that it would be desirable to be able to distinguish the ends 140 and 150 of the suture 102 during deployment so that the correct end is pulled by the operator to advance the knot. Should the non-rail end be pulled, the knot may be prematurely tightened before it is advance to its deployed position at the wall of the vessel.

The ends of the suture may be distinguished from each other by changing the color of one end (e.g. with dye), providing an attachment on one end (e.g. shrink wrap tubing, a bead, etc.) or with the suture itself (e.g. tying a knot in one end).

FIG. 15C shows the penetrator tips fully deployed into and engaged with the cuffs 110. FIG. 15D shows the penetrators being retracted after the tips have engaged the cuffs 110. On the anterior side 122, the penetrator 106' is pulling the anterior cuff 110 distally. On the posterior side 124, the penetrator tip 108 has been disengaged from the penetrator 106, via a mechanism described below. As shown in FIG. 15D, the link 112 is now coupled to one end of the suture via posterior cuff 110. Suture 102 is also shown exiting the posterior penetrator shank via an opening in the side of the penetrator shank.

Referring to FIG. 15E, after deployment of the foot 114, the suture 102 moves as indicated by directional arrows X1. As the suture 102 moves, a suture loop 103 also moves in a direction indicated by directional arrow X2 towards the foot 114 and the incision (not shown). The suture 102 moves through the foot 114 and through an opening distal to the foot 114 that defines a suture-bearing surface 111. The suture-bearing surface 111 is disposed at a distal end of the suturing device 100 separate from the foot 114, in this embodiment. The suture bearing surface 111 bears forces placed on the suture 102 during suturing. As such, the suture-bearing surface 111 minimizes forces placed on an incision during incision tensioning, thereby minimizing the possibility of damaging tissue immediately surrounding the incision. In this embodiment, the suture bearing 111 is a slot disposed at a distal end of the suturing device 100, which includes a passage for the suture 102 during incision suturing as shown with reference to the Figure.

As the suture loop 103 and the suture 102 move, the pre-tied suture knot 104 also moves in the same direction as the suture loop 103 towards the foot 114 and the incision. The suture loop 103 continues to move the pre-tied suture knot 104 towards the incision until the suture 102 and the pre-tied suture knot 104 suture the incision formed in the arterial wall. It should be noted that a suture trimmer might be used to assist the delivery of the knot 104 to an arteriotomy. The suture trimmer may be any device suitable for pushing the knot towards the arteriotomy and trimming suture immediately adjacent the knot 104 once the knot is tightened.

Now making reference to FIG. 15F, the suturing device 100 delivers the pre-tied suture knot 104 to the incision and the foot 114 is returned to its non-deployed position. The penetrators (not shown) have been retracted, the link has been fully retracted through the knot, and the knot has been advanced to the vicinity of the arterial wall. When the body of the device is removed, a stitch will remain in place across the incision in the artery. It should be noted that embodiments of the device described herein place a stitch of suture in a longitudinal orientation with respect to the vessel so as to minimize transverse vessel constriction and also to take advantage of the transverse orientation of the fibers of the vessel tissue.

FIGS. 16A and 16B show the suture bight in the pre-deployed state (FIG. 16A) and the deployed state (FIG. 16B). The suture 102 is arranged to provide the pre-tied knot 104 that automatically travels down from the shaft of the device where it is stored prior to delivery to the tissue wall. The loop 104 of suture 102 serves to pull the knot 104 down the rail portion 140 of the suture during deployment. It should be noted that it would be desirable to distinguish the ends 140 and 150 of the suture 102 during deployment so that the correct end is pulled by the operator to advance the knot. Should the non-rail end be pulled, the knot may be prematurely tightened before it is advanced to its deployed position at the wall of the vessel.

The ends may be distinguished from each other by changing the color of one end (e.g. with dye), providing an attachment on one end (e.g. shrink wrap tubing, a bead, etc.) or with the suture itself (e.g. tying a knot in on end).

FIG. 17A shows an enlarged detail of the posterior portion of the foot of one embodiment of suturing device 300. In an accordance with an embodiment of the present invention, the elongate body 306 may be any type of structure capable of penetrating the wall of a lumen, such as an artery, a blood vessel, or the like. In addition to the penetration capability, the elongate body 306 may be a hollow tube capable of holding suture. Examples of such structures may include a hypodermic needle or the like. The suturing device 300 stores the elongate body 306 within its shaft (not shown). As previously described with reference to FIGS. 2A through 2C, a user deploys a handle (not shown) of the suturing device 300 thereby deploying the elongate body 306 and the penetrator tip 308. During deployment, the elongate body 306 and the penetrator tip 308 penetrate the lumen wall W immediately surrounding the incision 305 and enter the lumen 307 of a patient, as shown with reference the following FIG. 17B.

Once the penetrator tip 308 engages with the cuff 310, the elongate body 306 and the penetrator tip 308, along with the cuff 310, proceed through the foot 314 and into the lumen 307. As may be seen with reference to FIG. 17B, the cuff 310 is pushed through the foot 314, such that the cuff 310 is pushed out of a pocket 316 and through the foot 314 into the lumen 307. Once the cuff 310 and the elongate body 306 enter the lumen 307, the penetrator tip 308 detaches from the elongate body 306 via a push mandrel 315 as shown with reference to FIG. 17C.

Figure 17C:
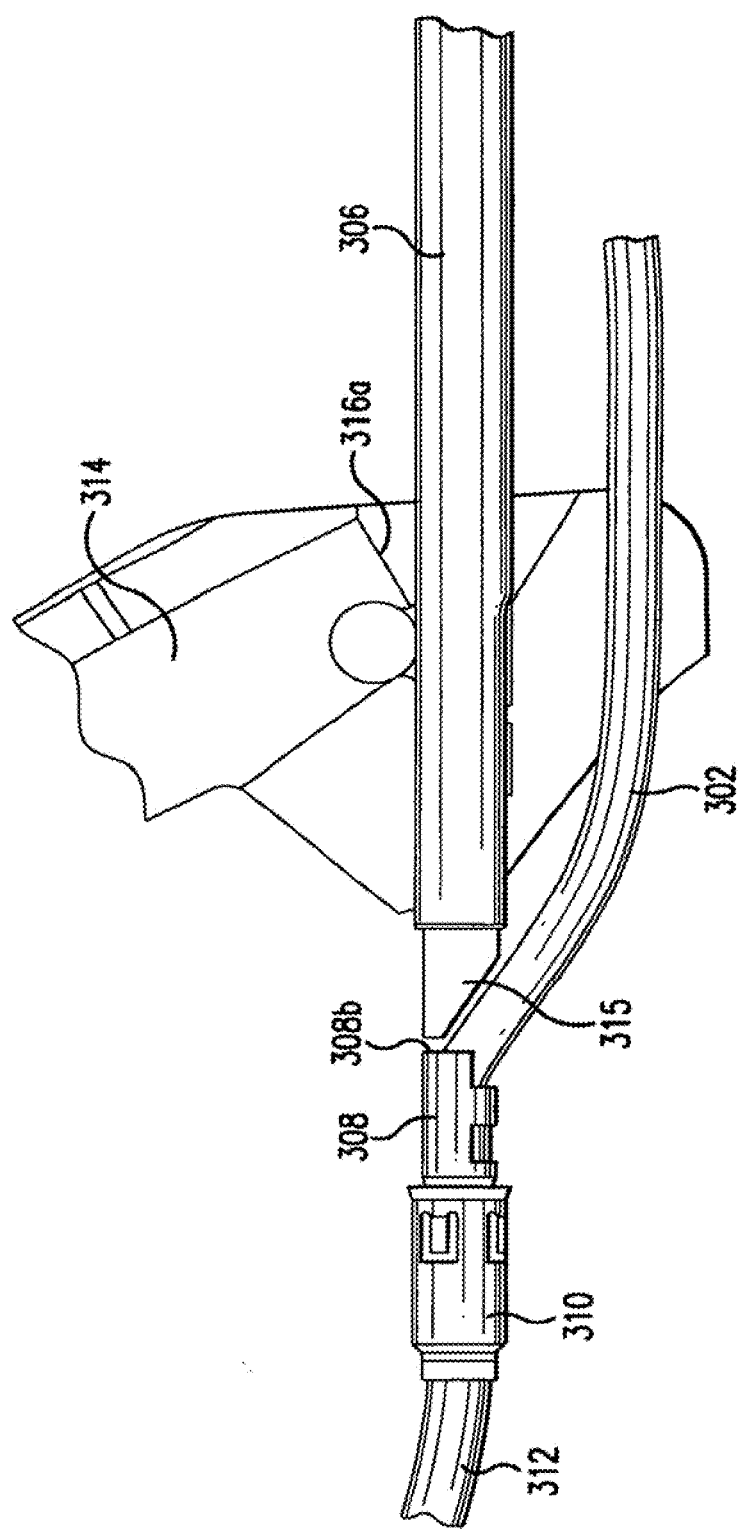

FIG. 17C illustrates the detachment of the pentrator tip 308 from the elongate body 306 in accordance with one embodiment of the present invention. Upon engagement of the penetrator tip 308 with the cuff 310, the push mandrel 315 is further advanced such that it contacts a proximal surface 308b of the penetrator tip 308, and further still until the penetrator tip 308 detaches from the elongate body 306. Upon detachment of the penetrator tip 308 from the elongate body 306, the push mandrel 315 and the elongate body 306 retract from the foot 314, as shown with reference to FIG. 17D.

As shown in FIG. 17D, after the penetrator tip 308 detaches from the elongate body 306, the elongate body 306 retracts from the penetrator tip 308 and cuff 310. Meanwhile, on the anterior side of the device (not shown in FIG. 17D), the elongate body 306' also includes the needle tip 308' which engages with the cuff 310' as previously described with reference to FIG. 15C. The needle tip 308' does not disengage from the elongate body 306' upon engagement with the cuff 310'. Therefore, during retraction of the elongate body 306' from within the lumen 307, the needle tip 308' also retracts from the lumen 307 through the penetration 309'. As the needle tip 308' retracts through the penetration 309', the elongate body 306' also retracts the cuff 310'. As previously described, the cuff 310' couples with the cuff 310 via the link 312. During retraction of the cuff 310' through the penetration 309', the cuff 310 and the suture 302 also retract through the penetration 309', thereby drawing the suture 302 through the penetration 309'. It should be noted that the foot 314 may provide suture bearing surface for the suture 302 during operation of the suturing device 300, as shown with reference to FIG. 18A.

Figure 18A:
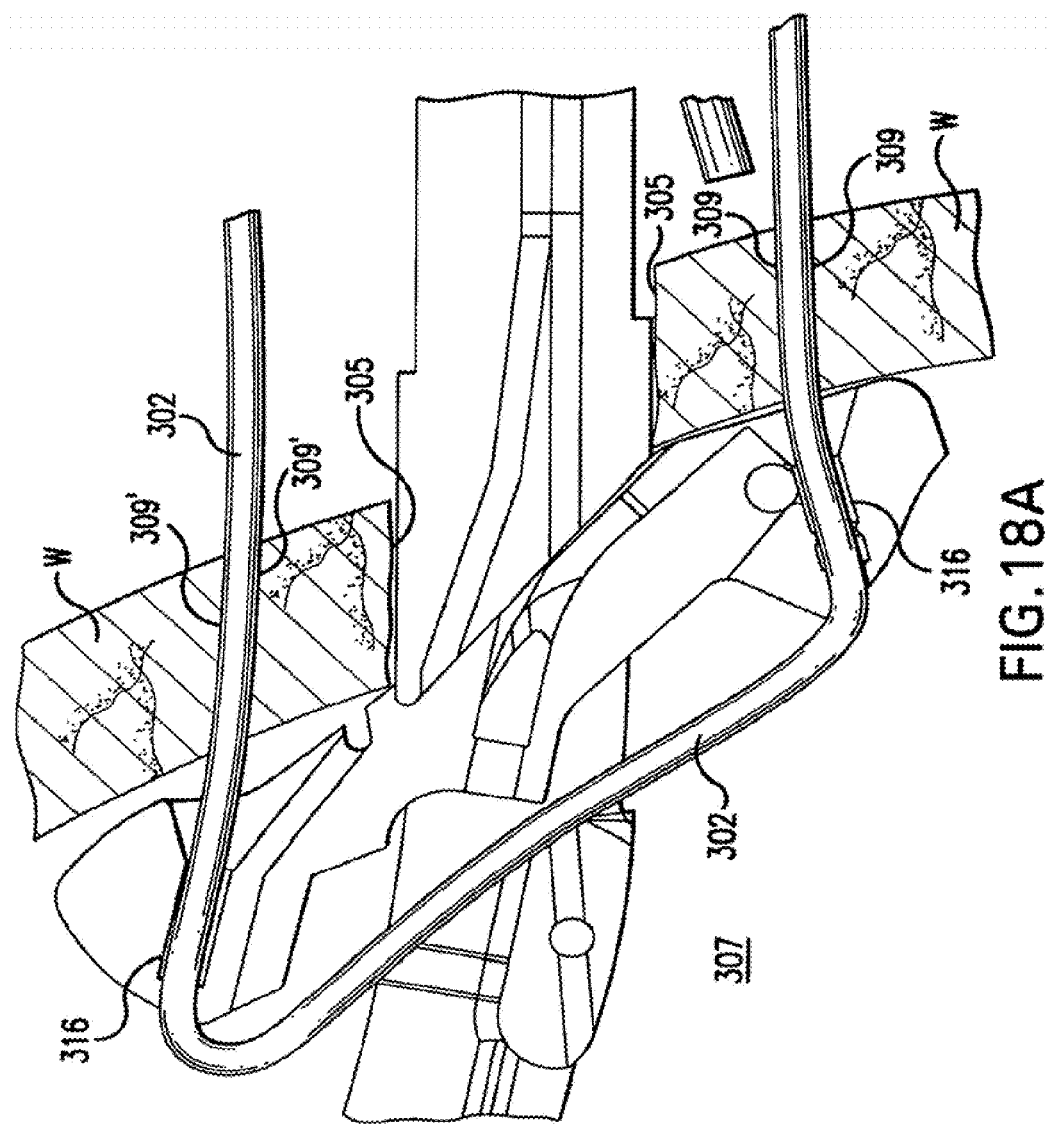
FIG. 18A is an enlarged partial cross-sectional view of an embodiment of a foot in accordance with the present invention, showing the link routing through the suture bearing surfaces of the foot.

FIG. 18A shows an embodiment of the present invention illustrating the passage of the suture 302 through the lumen 307 and the passageways 309 and 309'. As may be seen with reference to the Figure, the cuff pockets 316 of the foot 314 provide a suture-bearing surface for the suture 302 as the suture 302 is drawn through the passageways. The suture bearing surfaces of the foot 314 minimize the possibility of the suture 302 damaging tissue surrounding the incision 305.

Figure 18B:
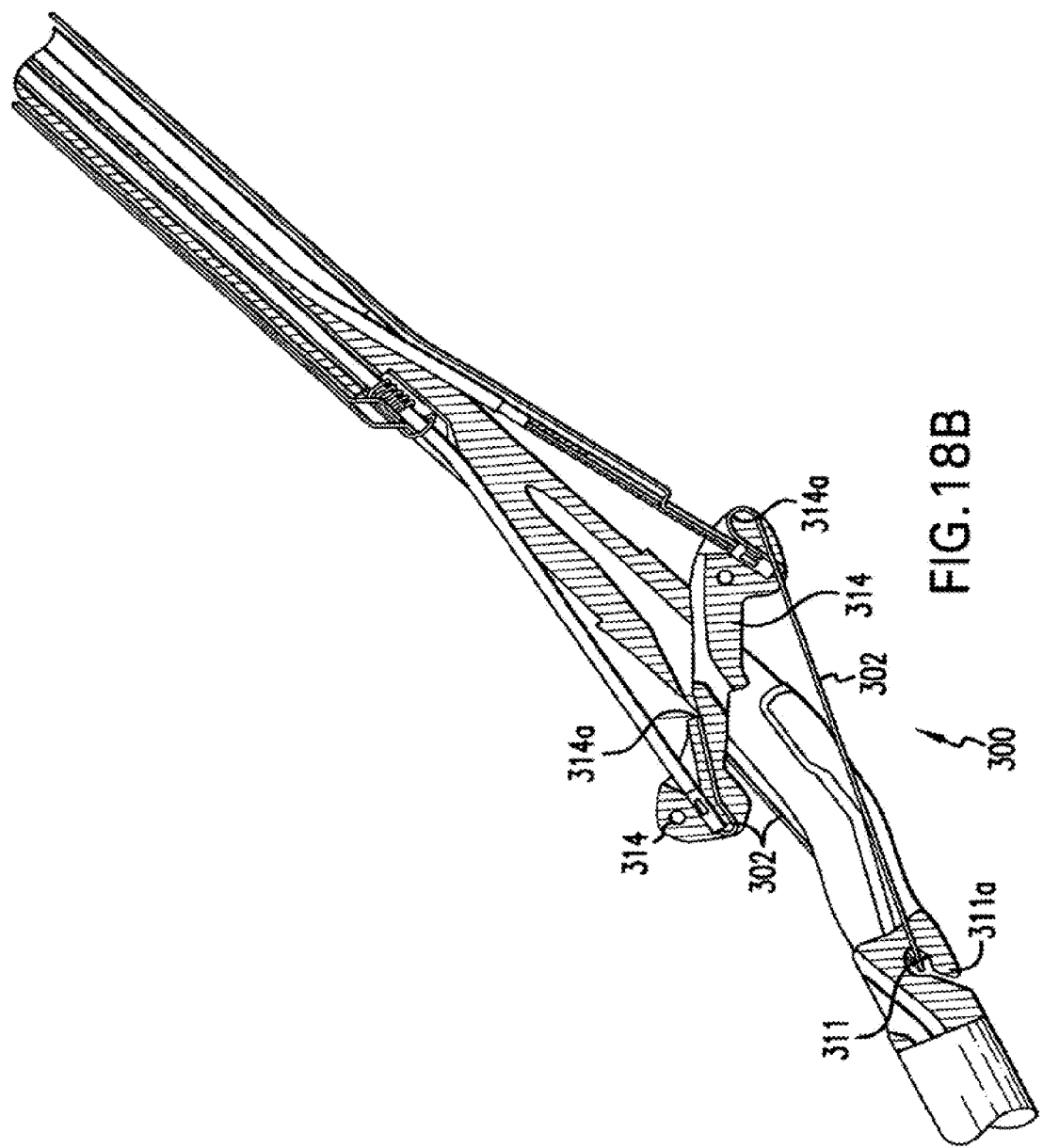
FIG. 18B is an enlarged partial cross-sectional view of an embodiment of a device in accordance with the present invention, showing the link routing through a suture-bearing surface located distal to the foot.

In another embodiment shown in FIG. 18B, the suturing device 300 also provides a suture bearing surface for the suture 302. During retraction of the elongate bodies 306 and 306' from the lumen 307, the suture 302 retracts through the foot suture bearing surfaces 314a and the suture-bearing surface 311 formed distally of the foot. The distal suture bearing surface 311 and the foot suture bearing surfaces 314a guide the suture 302 in order to minimize the possibility of the suture 302 damaging the patient during retraction of the elongate bodies 306 and 306' from the lumen 307. In this embodiment, suture-bearing surface 311 is a slot defined in the body of the device distal of the foot. The slot includes a passage for the link and suture, and an edge 311a. It is contemplated that the edge 311a may contact the edge of the incision in the artery and become caught on the adventitia of the blood vessel. Various devices may be provided, such as flaps, o-rings, etc., that provide a smoother transition over the slot and edge 311a as the device is inserted through the incision.

Figure 19B:
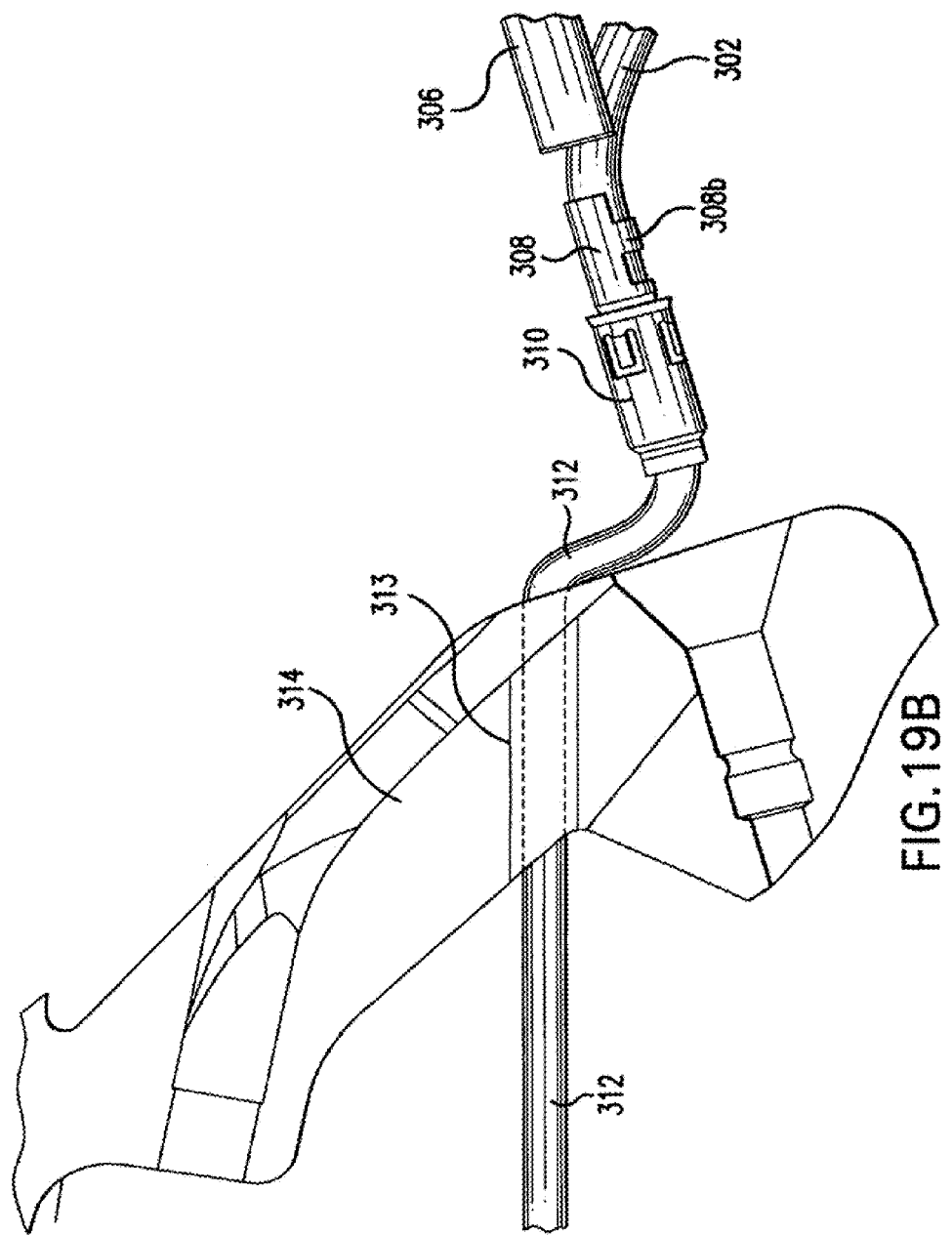

FIGS. 19A and 19B illustrate an alternative embodiment of the present invention for releasing the cuff 310 from the foot 314. In this embodiment, the foot 314 includes link passageway 313 through which the link 312 passes. After the elongate body 306 engages the penetrator tip 308 with the cuff 310, the elongate body 306, during retraction from the foot 314, removes the cuff 310 and the penetrator tip 308 from the foot 314. The force holding the penetrator tip 308 on the elongate body 306 overcomes the force holding the cuff 310 in the cuffpocket 316. Once the cuff 310 clears the foot 314 and attains the orientation shown with reference to FIG. 19B, the previously described push mandrel (not shown) detaches the penetrator tip 308 from the elongate body 306. Upon detachment of the penetrator tip 308 from the elongate body 306, the link 312, along with the cuff 310 and the penetrator tip 308, retracts through the passageway 313 via the link 312 and the elongate body 306'. In an alternate embodiment, the cuff 310 and pentrator tip 308 may be pulled off the elongated body 306 by tension in the link 312.

In yet another alternate embodiment shown in FIGS. 20A through 20C, the cuff 310 and penetrator tip 308 may be detached from the elongate body 306 before being removed from the cuff pocket 316. In this embodiment, after the elongate body 306 and the penetrator tip 308 engage with the cuff 310, the push mandrel 315 detaches the penetrator tip 308 from the elongate body 306, leaving it in the cuff pocket 316 to be removed by tension in the link 312, as shown in FIG. 20C.

It should be noted that other methods might be used to detach the penetrator tip 308 from the elongate body 306. These methods include, but are not limited to, detachment through friction or tension. Making reference to FIG. 20B, in an embodiment where friction between the cuff pocket 316 and the cuff causes detachment of the penetrator tip 308 from the elongate body 306, a surface 308c of the penetrator tip 308 frictionally engages with a cuff surface 316a of the cuff pocket 316. During retraction of the elongate body 306 from the foot 314, the frictional engagement between the cuff surface 316a and the penetrator tip surface 308c causes detachment of the penetrator tip 308 from the elongate body 306. In an embodiment where link tension causes detachment of the penetrator tip 308 from the elongate body 306, the link 312 is tensioned such that the link 312 is taut between the cuffs 310 and 310'. As such, the tension of the link 312 prevents movement of the cuff 310 out of the foot 314 along with the elongate body 306 during retraction of the elongate body 306 from the foot 314, thereby causing detachment of the penetrator tip 308 from the cuff 310.

After detachment, during retraction of the elongate body 306 and the elongate body 306' (not shown), the link 312 may draw the cuff 310 and the penetrator tip 308 from the cuff pocket 316. As discussed earlier, the cuff 310' engages with the elongate body 306' and pulls the cuff 310 via the link 312 as the elongate body 306' retracts from the lumen 307. As such, retracting the link 312 pulls on the cuff 310, thereby pulling the cuff 310 from the cuff pocket 316 and through the lumen 307 along with the suture 302, as shown with respect to FIG. 20C.

FIG. 21 shows the pre-tied suture knot 304 disposed about a periphery of a knot tube 301. In this embodiment, the knot tube 301 includes a hollow center 301a configured to allow passage of an elongate body (not shown) as the suturing device 300 sutures the incision. However, it should be noted that in an alternative embodiment of the present invention, the elongate body (not shown) might also store the suture 302. In the alternative embodiment, the suture 302 and the pre-tied suture knot 304 are disposed about a periphery of the elongate body where the pre-tied suture knot 304 may reside within a pocket (not shown) of the elongate body.

Figure 22A:
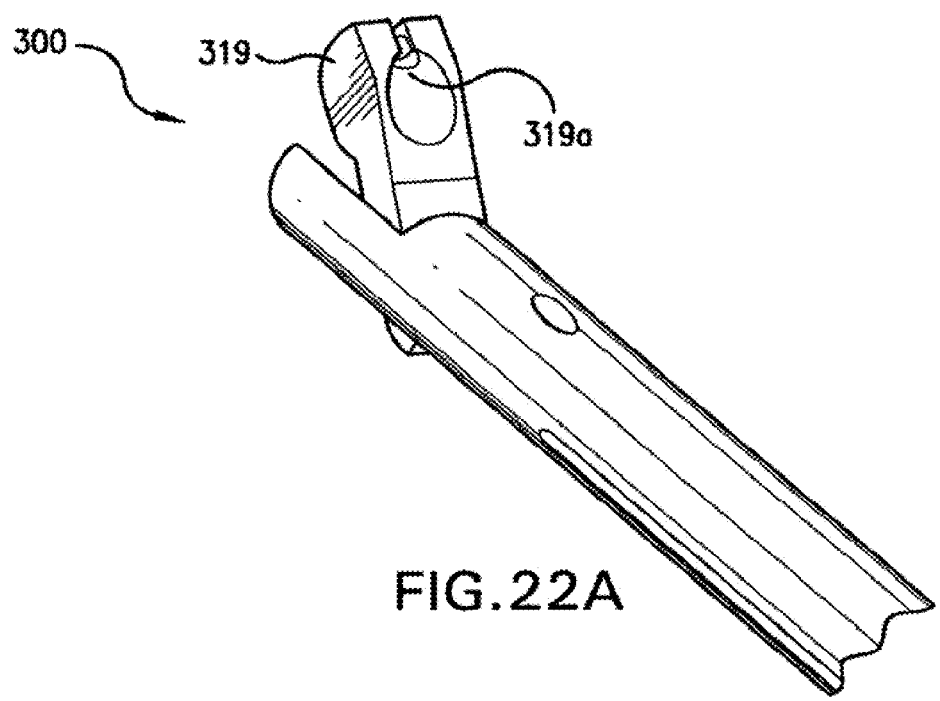
FIGS. 22A through 22C show an alternate embodiment of a foot in accordance with the invention.
Figure 22B:
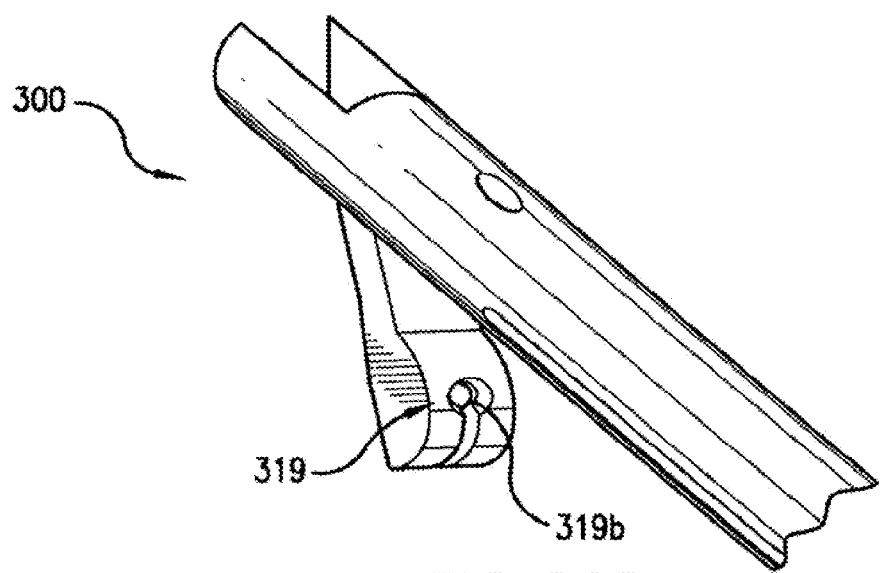
Figure 22C:
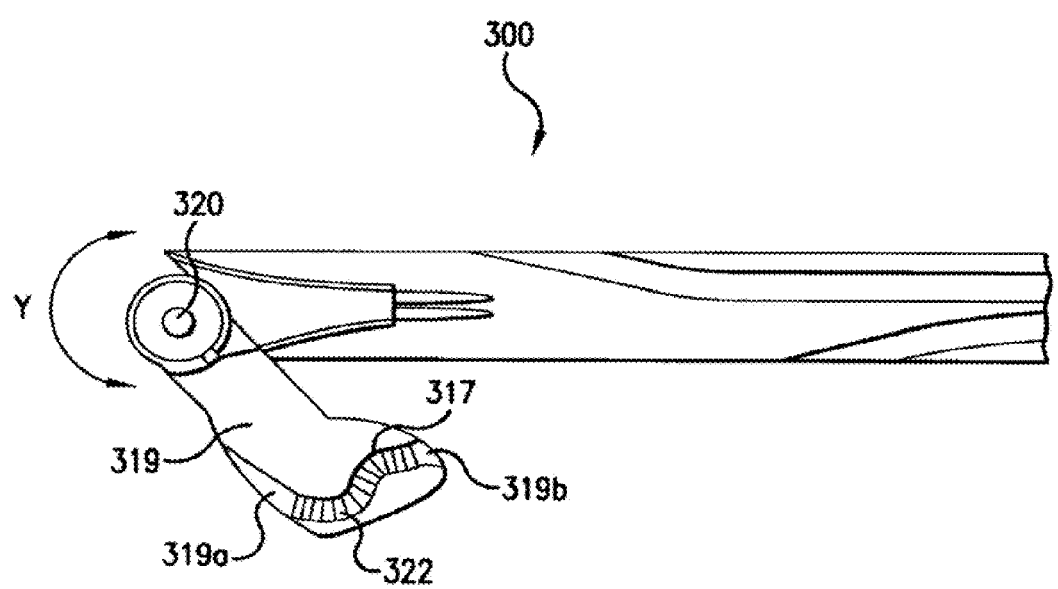

Embodiments of the suturing device of the invention may also include additional configurations for a foot, as shown with reference to FIGS. 22A through 22C. In this embodiment, the suturing device 300 includes a foot 319 having cuff pockets 319a and 319b. The configuration of the cuff pockets 319a and 319b allow the foot 319 to hold the cuffs 310 and 310' during use of the suturing device 300. The foot pivots from a first orientation shown with reference to FIG. 22A to a second orientation shown with reference to FIG. 22B via a hinge 320 as shown in FIG. 22C.

FIG. 22C shows the hinge 320, which allows rotation of the foot 319 in a direction indicated by directional arrow Y. The hinge 320 may be any device capable of rotatably coupling the foot 319 to the suturing device 300, such as pin assembly or the like. In addition to the hinge 320, the foot 319 includes a connector 322 that couples the cuffs 310 and 310' with one another. The connector 322 also includes a flexible portion 322c (shown with respect to FIG. 22C) that allows flexing of the connector 322 as the connector 322 resides within passage 317 of the foot 314. The connector also includes ends 322a and 322b that facilitate connection with the penetrator tip 308 and the needle tip 308' of the elongate bodies 306' and 306.

In an embodiment of the present invention where the suturing device 300 employs the foot 319, during use of the suturing device 300, upon insertion of the suturing device 300 within the lumen 307, a user deploys the foot 319 as shown with reference to FIG. 22A. Upon deployment of the foot 319, the user deploys the elongate body 306 (not shown) that engages with the cuff 310 (not shown) as previously described. Once the penetrator tip 308 detaches from the elongate body 306 via the push mandrel 315, or other means previously described, the user rotates the foot 319 into the orientation shown with reference to FIG. 22B. Upon orientation of the foot 319 as shown with respect to FIG. 22B, the user deploys the elongate body 306' (not shown) which engages with the cuff 310' (not shown). After the elongate body 306' engages with the cuff 310', the user retracts the elongate body 306' along with the cuffs 310 and 310' and the suture 302 to suture an incision as previously described.

Figure 23A:
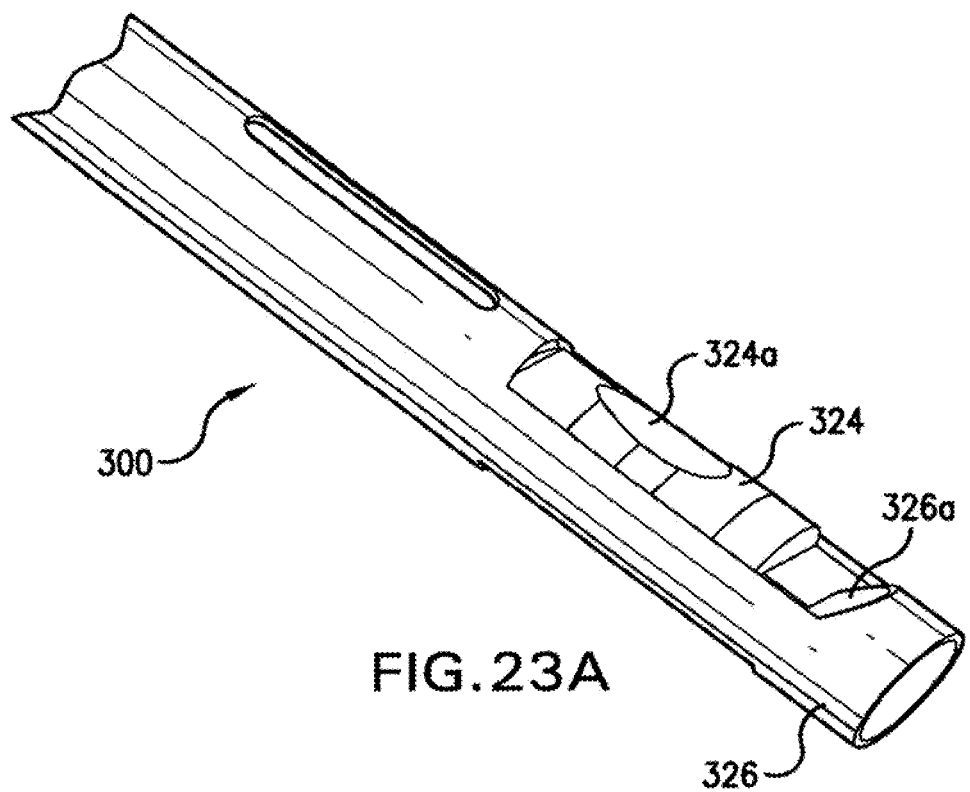
FIGS. 23A through 23C show another alternate embodiment of a foot in accordance with the invention.
Figure 23B:
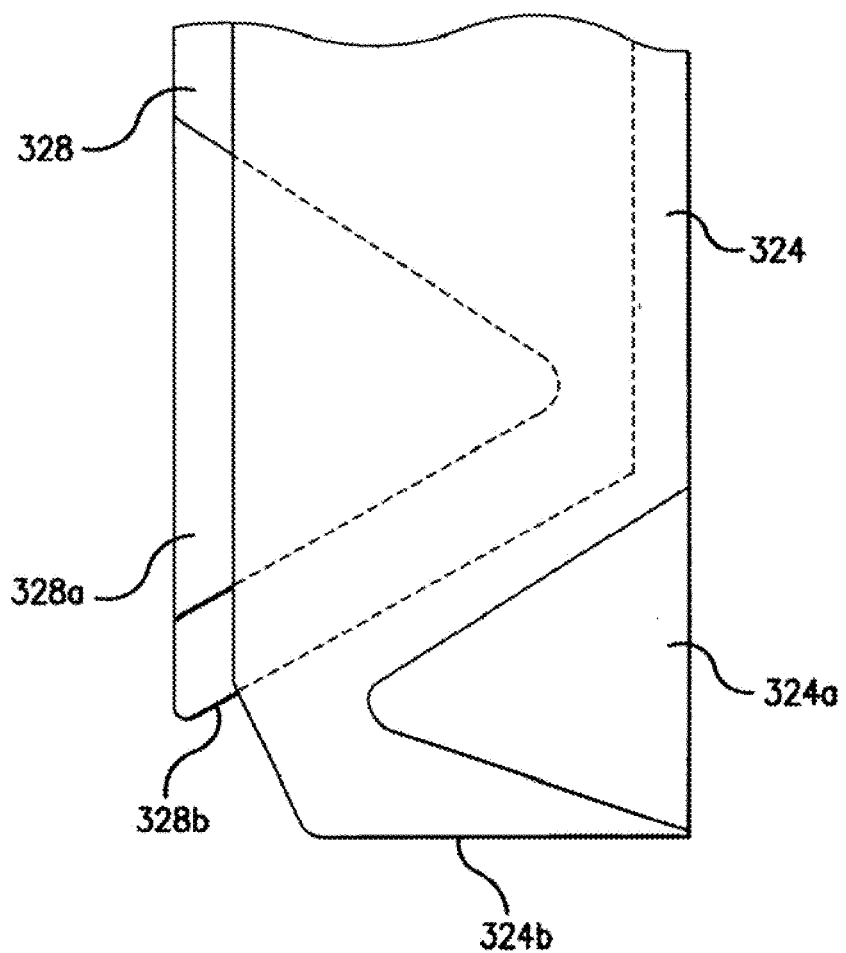
Figure 23C:
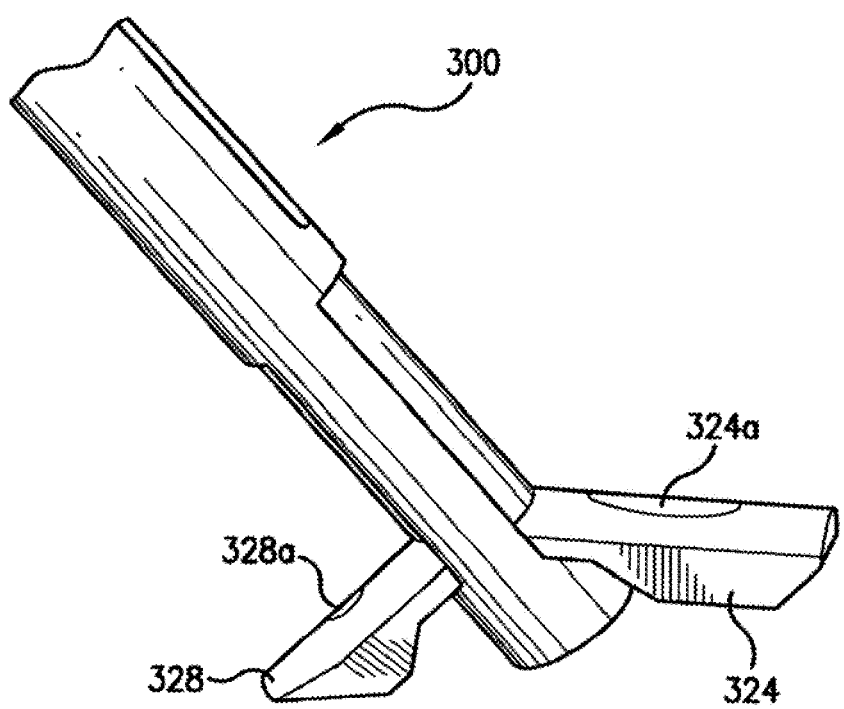

Another embodiment of the suturing device 300 includes feet 324 and 328 as shown with reference to FIG. 23A. FIG. 23A illustrates an embodiment of the present invention in which the suturing device 300 includes the feet 324 and 328. As may be seen with reference to FIG. 23B, the foot 324 is hollow such that the foot 328 fits within the foot 324 during both insertion and retraction of the suturing device 300 within the lumen 307. The feet 324 and 328 also include cuff pockets 324a and 328a and cam surfaces 324b and 328b. The configuration of the cuff pockets 324a and 328a allow placement of the cuffs 310 and 310' within the feet 324 and 328 during use of the suturing device 300; allowing engagement of the elongate bodies 306 and 306' during suturing. The cam surfaces 324a and 328a contact cam surfaces 326a in order to deploy the feet 324 and 328. Once the feet 324 and 328 deploy, the suturing device 300 attains the configuration shown with reference to FIG. 23C.

During use of a suturing device implementing the feet 324 and 328, a user inserts the suturing device into an incision as the foot 328 resides within the foot 324. Upon insertion of the suturing device within the incision, the user deploys the feet 324 and 328 by moving the feet 324 and 328 towards the cam surfaces 326a, in order to deploy the feet 324 and 328, as previously described. After deployment of the feet 324 and 328 within a lumen, the user deploys the elongate bodies 306 and 306' whereby the penetrator tip 308 and needle tip 308' engage with the cuffs 310 and 310' residing within the cuff pockets 324a and 328a. Upon engagement with the cuffs 310 and 310' the user retracts the elongate bodies 306 and 306' and sutures the incision.

Figure 24A:
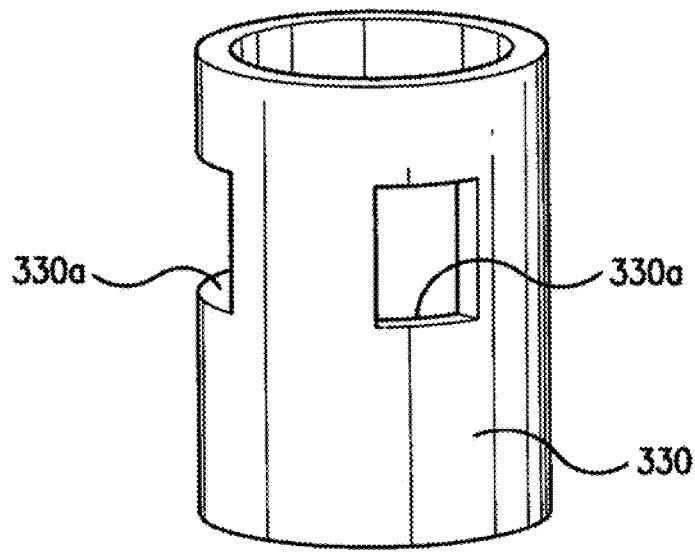
FIGS. 24A and 24B are perspective views of an alternative embodiment of a penetrator tip in accordance with the invention.
Figure 24B:
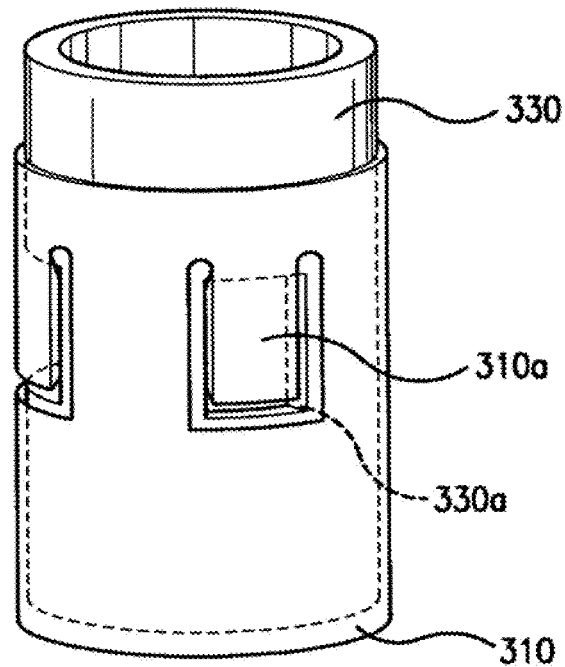

In addition to the alternative configurations for the foot of the suturing device 300, the suturing device 300 may also include alternative cuff configurations that allow engagement of the elongate bodies 306 and 306' with the link 312. An example of such an alternative configuration is shown with respect to FIG. 24A. FIG. 24A illustrates a perspective view of an alternative embodiment of the penetrator tip 330. In this embodiment, a penetrator tip 330 includes mating surfaces 330a which engage with the previously described cuff tabs 310a of the cuff 310 when the penetrator tip 330 engages with the cuff 310, as shown with reference to FIG. 24B. As such, a user detaches the elongate body 306 from the penetrator tip 330 with the push mandrel 315 after engagement of the penetrator tip windows 330a with the cuff tabs 310, as discussed with reference to the penetrator tip 308 and the cuff 310. The mating surfaces 330a may be cut-outs, such as windows, formed within the penetrator tip 330. The elongate bodies 306 and 306' may also engage with the link 312.

Figure 25A:
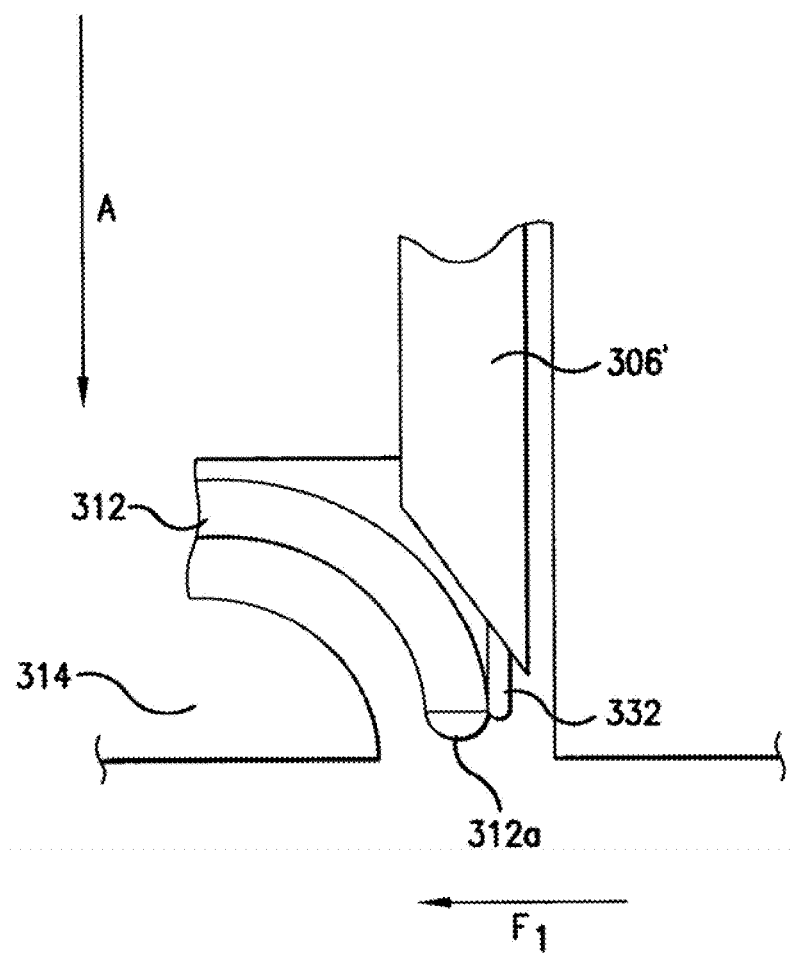
FIGS. 25A through 25C are schematic views of an alternate embodiment of a vessel closure device in accordance with the present invention.

FIG. 25A shows an alternative method of coupling the elongate bodies 306 and 306' with the link 312. In this embodiment, the elongate body 306' includes a loop 332 (shown in FIG. 25B) which engages with the link 312 as the elongate body 306' enters the foot 314. In this embodiment, the link 312 is constructed of a resilient material capable of flexing in response to the loop 332 contacting the link 312, such as polypropylene or any other material having spring-like characteristics. The elongate body 306' moves in a downward direction as indicated by directional arrow A until the loop 332 comes into contact with an end 312a of the link 312. When the loop 332 contacts the end 312a, the loop 332 moves the end 312a in a direction F1 indicated by directional arrow F1. The catch 332 continues to move the end 312a of the link 312 in the direction F1 until the loop 332 contacts the end 312a, as shown with reference to FIG. 25B.

Figure 25B:
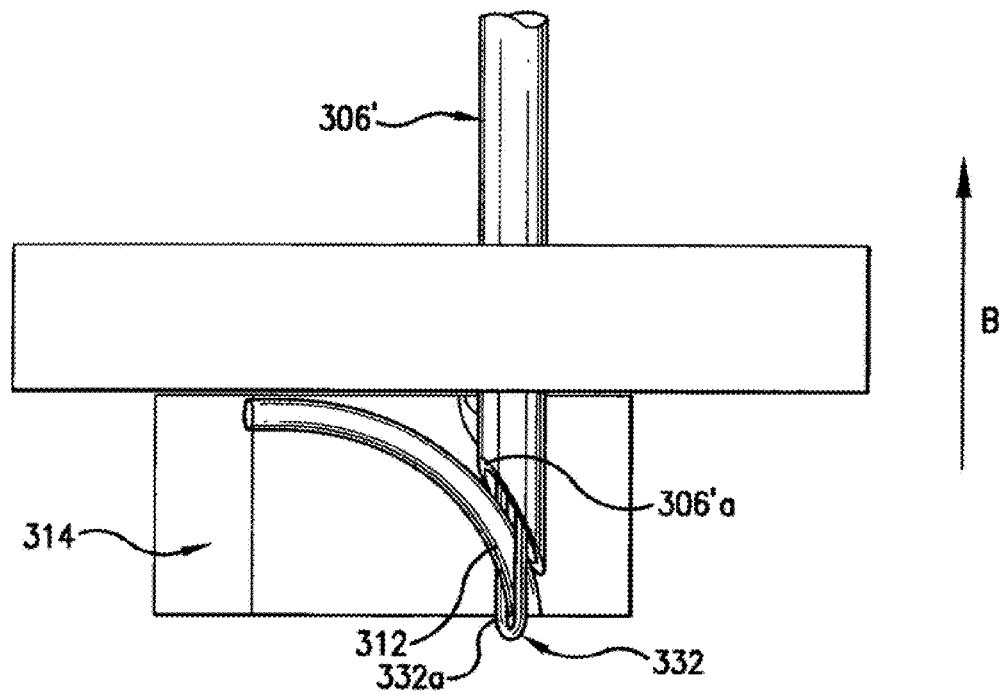
Figure 25C:
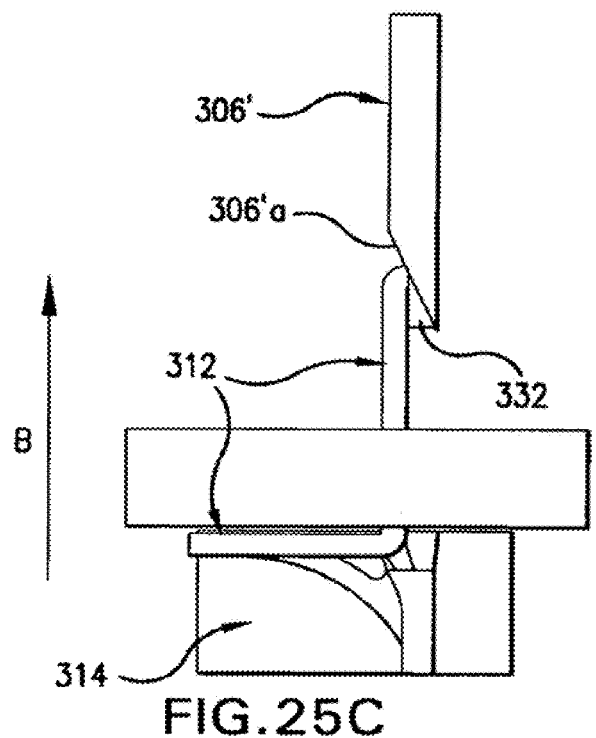

Referring to FIGS. 25A-C, the link 312 is constructed of a material having spring like properties. Therefore, when the loop 332a comes into contact with the end 312a, the resilient properties of the link 312 move the end 312a in a direction F2, as indicated by directional arrow F2 in FIG. 25A. The end 312a moves in the direction F2 such that the end 312a moves into the loop 332a, as shown with reference to FIG. 25B. Once the end 312a moves into the loop 332a, a user retracts the loop 332 along with the end 312a and the link 312 in a direction B as indicated by directional arrow B of FIG. 25C. As the loop 332a and the catch 332 move in the direction B, the loop 332a clamps the link 312 against a surface 306' a of the elongate body 306'. Thus, during retraction of the suturing device 300 from the foot 314, the link 312 remains engaged with the elongate body 306', as shown with reference to FIG. 25C. As the elongate body 306' and the catch 332 retract from the foot 314, the catch 332 pulls the link 312 through the foot 314, also as shown with reference to FIG. 25C. While the catch 332 pulls the link 312, the cuff 310 (not shown) and the suture 302 (not shown) move through the foot 314 in order to enable suturing of an incision.

Figure 26A:
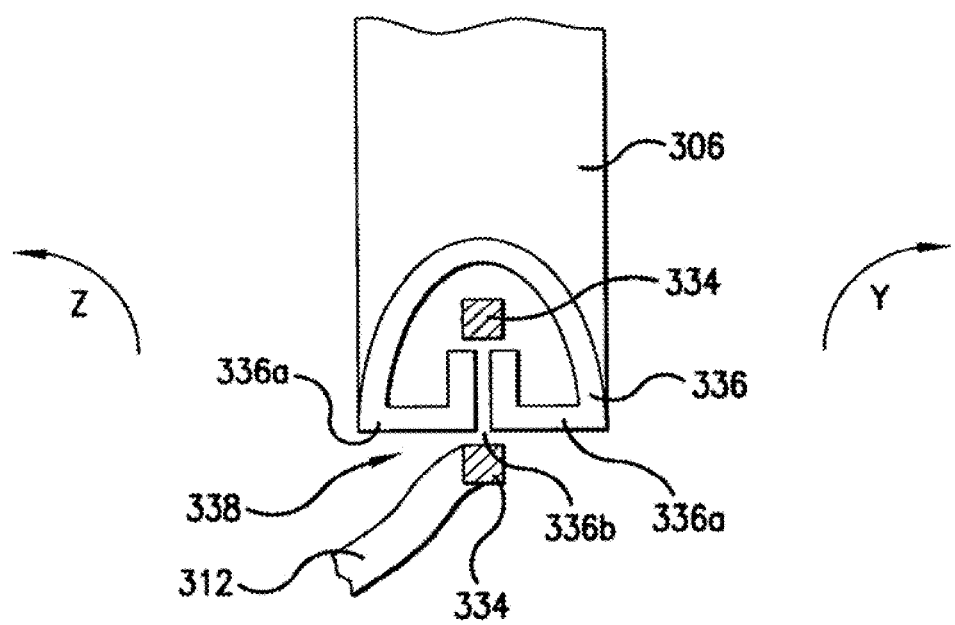
FIGS. 26A through 26D are schematic views of alternate embodiments of a vessel closure device in accordance with the invention.

In another embodiment, the suturing device 300 may also employ a clip and ring assembly 338 which couples the elongate bodies 306 and 306' with the link 312, as shown with reference to FIG. 26A. FIG. 26A illustrates a schematic view of the clip and ring assembly 338 for coupling the elongate bodies 306 and 306' with the link 312 in accordance with an embodiment of the present invention. The elongate bodies 306 and 306' include a clip 336 in place of the penetrator tip 308 and the needle tip 308' where the clip 336 has a configuration as shown with reference to the Figure. The clips 336 include flexible arms 336a and a passageway 336b.

Figure 26B:
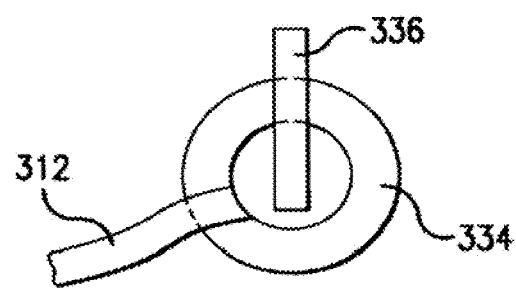
Figure 26C:
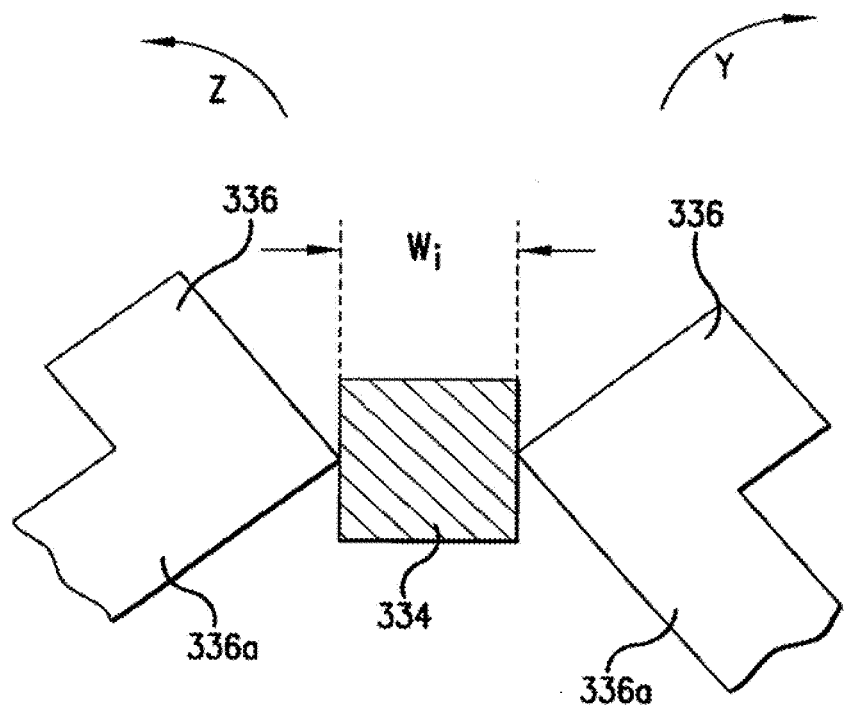

The clip and ring assembly 338 also includes a ring 334 that engages with the clip 336. The link 312 couples with the ring 334 using any suitable technique, such as tying or the like. The ring 334 has a circular configuration as shown with respect to FIG. 26B such that as the elongate bodies 306 and 306' engage with the foot 314, the clip 336 couples with the ring 334. As the clips 336 engage with the ring 334, the flexible arms 336a flex in a direction indicated by directional arrows Y and Z thereby increasing a width Wi of the passageway 336b in order to allow passage of the ring 334 through the clip 336 as shown with regards to FIG. 28C.

Figure 26D:
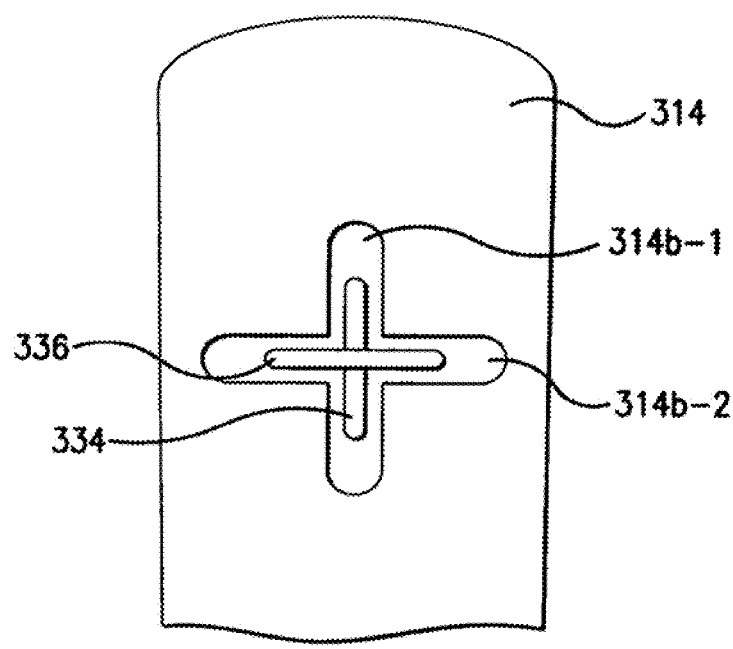

Referring to FIG. 26D, there is shown a top view of the foot 314 where the foot 314 includes cuff pockets 314b-1 and 314b-2. The cuff pocket 314b-1 holds the ring 334 prior to engagement with the clip 336. The cuff pocket 314b-2 is configured such that as the elongate bodies 306 and 306' enter the foot 314, the clips 336 enter the cuff pocket 314b-2 and engage with the ring 334 as shown with reference to the Figure. Once the clip 336 engages with the ring 334, the clip 336 coupled with the elongate body 306 detaches from the clip 336 while the elongate body 306' remains engaged with the clip 336. During retraction of the elongate bodies 306 and 306' from the foot 314, the elongate body 306' pulls the link 312 and the suture 302 through the foot 314 in order to suture an incision.

Figure 27:
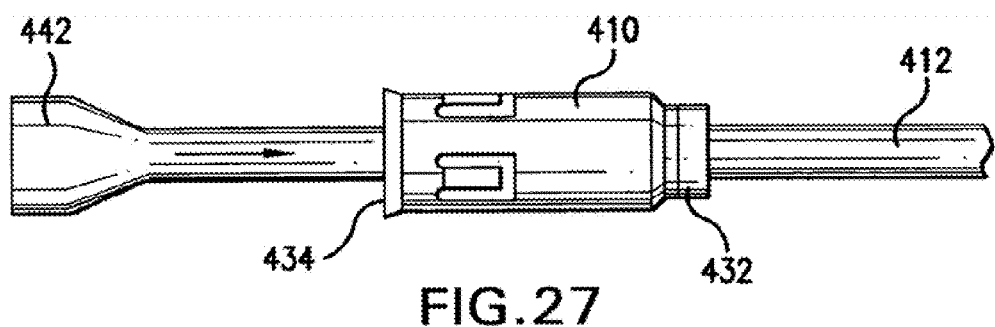
FIG. 27 shows a schematic view of one embodiment of a link and cuff assembly in accordance with the invention.

FIG. 27 shows an embodiment of a cuff 410 and link 412 assembly that may be provide with the various embodiments of the present invention. Cuff 411 has a penetrator tip receiving end 434 and a tapered end 432. Link 412 has two ends 442 (only one shown in FIG. 27). An example of a preferred link material is expanded Polytetrafluoroethylene (ePTFE). PTFE is commonly referred to as Teflon. ePTFE is particularly suited for use as the link material in the vessel closure devices described herein because of its low friction, high strength properties.

To assemble the link and cuff assembly, a length of link material is first threaded through the cuff. The end of the link material extending from the penetrator tip receiving end 434 of the cuff 410 is then heated so that it expands. The link is then pull through the cuff 410 such that the expanded end portion 442 is seated in the interior tapered end 432 of the cuff 410.

The various embodiments of the suturing device may include any of a variety of types of suture, such as braided or monofilament. The suture material may be absorbable or nonabsorbable and may be made of polyester, polypropylene, polyglycolic acid, nylon, silk or any of a variety of suture materials known in the art. Suture material coated with antibiotics or other antimicrobial agents may also be provided with the suturing devices of the present invention.

An exemplary suture material is TEVDEK II®, a braided polyester suture material that is impregnated with PTFE and manufactured by Genzyme Biosurgery of Cambridge, Mass. An exemplary monofilament suture material is DEKLENE II®, a polypropylene suture material also manufactured by Genzyme Biosurgery. Another exemplary monofilament suture material is nylon monofilament, also manufactured by Genzyme Biosurgery. While braided polyester and monofilament polypropylene or nylon are suitable suture materials that may be used with the devices of the present invention, monofilament suture materials may require post-manufacturing processing in order to form the pre-tied knot of the embodiments described with reference to FIGS. 11A through 11E and 14A through 21.

Monofilament suture material tends to be stiffer relative to braided suture material. As such, forming a bight of suture for the purpose of providing a pre-tied knot is more difficult with monofilament suture than with the more flexible braided suture. The monofilament suture material will tend to straighten itself out after being looped to form a bight 80 (shown in FIGS. 11Ai and 11Aii). Therefore, in order to provide a bight of monofilament suture that is releasably disposed on the shaft of the device without unraveling, such as shown in FIGS. 11Ai and 11Aii, FIG. 15A (pre-tied knot 104), and FIG. 21 (pre-tied knot 304), the loops forming the bight are heated to set the bight. The heating of the bight of monofilament suture to set the bight is performed after the suture has undergone any manufacturing procedures that may include drawing, annealing or any other procedure that employs heat to manufacture the suture material.

A method of forming a pre-tied knot for a suturing device of the present invention includes providing a length of monofilament suture having a first end, wrapping a portion of the length of monofilament suture around a mandrel to form a looped configuration spaced from the first end, and heating the wrapped portion to a temperature below the melting point of the monofilament suture such that upon removal of the mandrel, the wrapped portion remains in the looped configuration.

The bight of the suture includes at least one loop. The heating of the at least one loop is performed to set the bight in the looped configuration. The temperature is kept below the melting temperature of the suture material, yet is selected to cause the suture to remain in the formed looped configuration after the bight is removed from the heat. The temperature is selected so as not to adversely affect properties such as strength of the suture.

In one exemplary heating process, a length of size 3/0 polypropylene suture is looped around a mandrel to form a bight which is heated at a temperature between about 240° Fahrenheit to about 260° Fahrenheit, or nominally about 250° Fahrenheit, for about 3 to about 5 seconds. The heat is provided by a blowing heat source such as a heat gun that provides an air flow at a rate of about 10 to about 30 standard cubic feet per hour (scfh), or nominally about 20 scfh. The heating of the formed bight may be accomplished in an oven that is heated to about 200° Fahrenheit to about 280° Fahrenheit. When the bight is formed using an oven, the amount time that the bight is held in the heat of the oven is approximately 1 minute to about 15 minutes. The specific heating temperatures and times may be selected as appropriate for different suture sizes or types, or different types of bight configurations.

In another embodiment, a monofilament nylon suture material may be provided to form a pre-tied knot in a suturing device of the present invention. The temperature at which a bight formed with size 3/0 nylon suture is heated to set the bight is about 190° F. to about 210° F., and nominally about 200° F., for about 3 to about 5 minutes with a blowing heat source such as a heat gun. In an oven, the temperature used at which the bight is set is about 190 to about 210, or nominally about 200° F. for about 1 minute to about 15 minutes.

Figure 28:
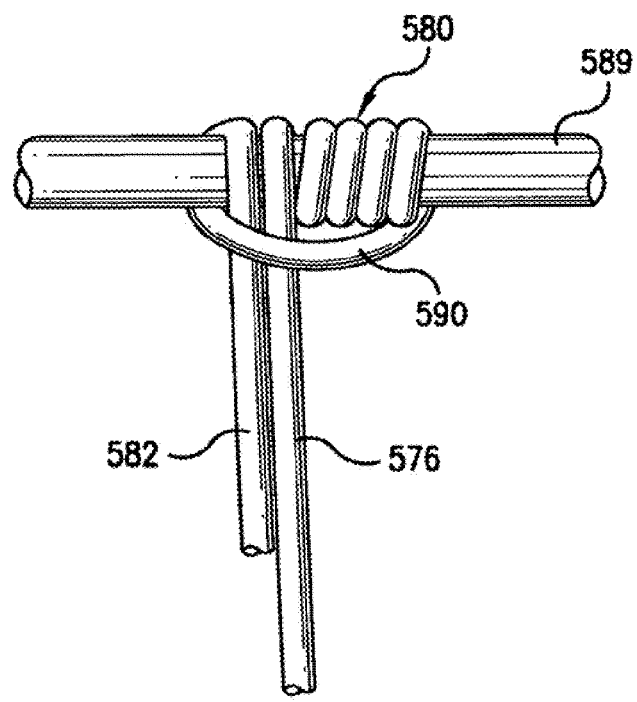
FIG. 28 shows a bight of suture wrapped on a mandrel to form a prettied knot in accordance with the invention.

FIG. 28 shows a bight 580 of monofilament suture wrapped around a mandrel 589 in preparation for heating the loops of the bight to set the bight. The mandrel may be a polyimide shaft or tube having a diameter of about 0.65 mm, for example. In the example shown in FIG. 28, the suture is size 3/0 and is wrapped to form a looped configuration which defines a clinch knot. To wrap the suture as shown in FIG. 28, a length of suture is held against the mandrel with a first end 576 oriented across the mandrel. The second end of the length of suture is wrapped five times around the mandrel. The second end is then wrapped over the first end to form loop 590 transverse to the first five loops. The second end is then looped behind the mandrel and wrapped over the mandrel in the opposite direction from the first five loops. The second end is then routed through loop 590 to form the pre-arranged or pre-tied knot.

Figure 29:
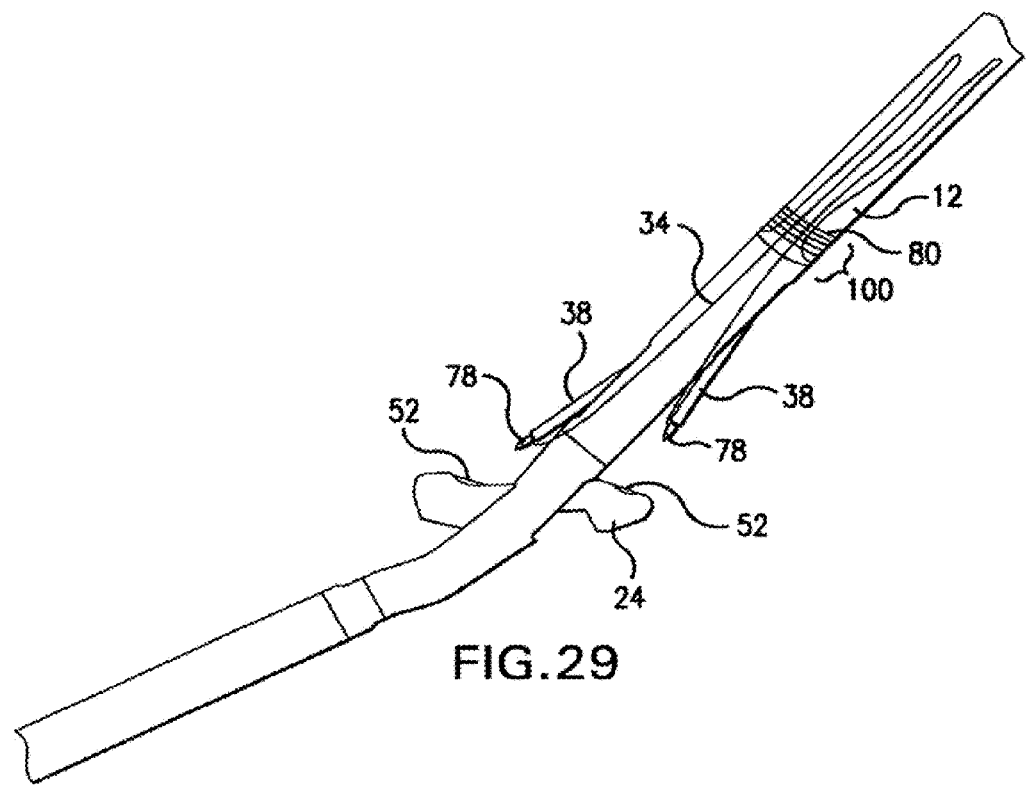
FIG. 29 illustrates one embodiment of a vessel closure device including another embodiment of a pre-tied knot.

FIG. 29 illustrates another embodiment of the present invention further including a pre-tied knot 100 of suture disposed around shaft 12. Needles 38 each have detachable needle tips 78 attached to the ends of the needles. Detachable needle tips 78 each have opposite ends of suture 34 affixed thereto. Bight 80 is prearranged to define the pre-tied knot 100 when an end of the suture 34 passes therethrough, as described above with reference to FIGS. 11A to 11E. An exemplary knot was described with reference to FIG. 11Aii, above. It should be noted that bight 80 will often include more than one loop, and may be prearranged to define a variety of known or new knots.

In operation, needles 38 each carry an opposite end of suture 34 toward foot 24 after foot 24 has been deployed (as shown). Each needle 38 includes a detachable tip 78 such that when needles 38 are advanced through tissue and into receptacles 52 in foot 24, the ends of suture 34 are deposited, together with the detachable needle tips 78, into receptacles 52. The detachable tips 78 are then detached from the needles 38 by push mandrels (not shown) from inside the hollow needles, for example. Alternatively, tips 78 may be frictionally or mechanically held within receptacles 52 such that they are pulled off the needles 38 upon retraction of the needles from the foot. Needles 38, without tips 78, are then retracted back up into shaft 12, and foot 24 carrying tips 78 with suture 34 ends is then rotated back into a non-deployed position.

Figure 30:
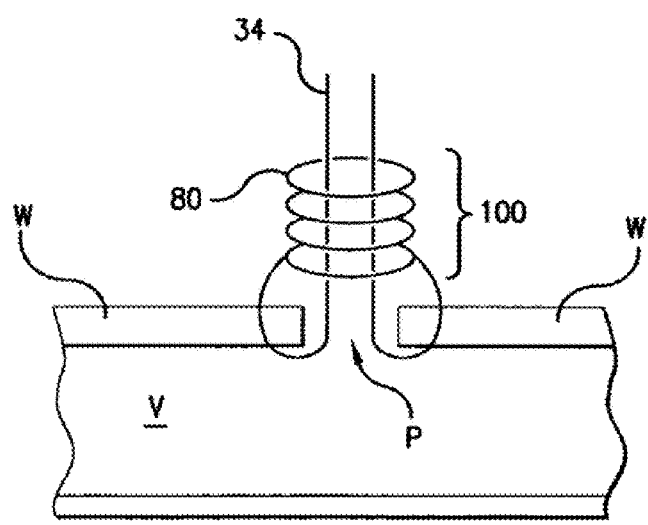
FIG. 30 illustrates the suture pattern after the device of FIG. 29 has been removed, showing the deployment of the pre-tied knot.

When shaft 12 is removed from the patient's body, foot 24 is in its undeployed position, and the ends of the suture 34 are adjacent the central axis of the shaft 12. Pre-tied knot 100 will then slide down shaft 12, over the ends of the suture 34, resulting in the suture pattern as shown in FIG. 30 in which the opposite ends of suture 34 pass upwardly through the bight 80 to form the pre-tied knot 100.

Figure 31:
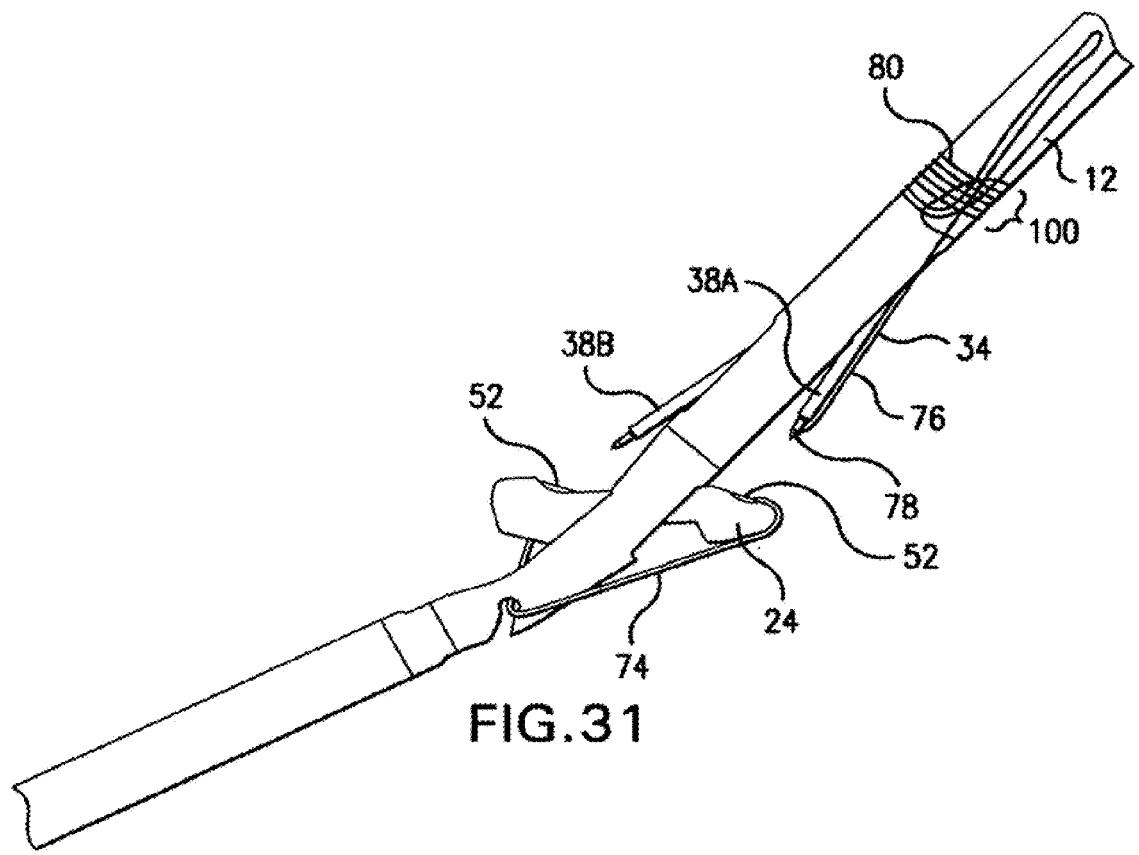
FIG. 31 illustrates another embodiment of a vessel closure device including another embodiment of a pre-tied knot.

FIG. 31 illustrates another embodiment of the present invention also including a pre-tied knot 100 of suture disposed around shaft 12, as follows. Needle 38A carries one end of suture 34. A detachable tip 78 is disposed on the end of needle 38A. The detachable tip 78 is connected to the suture end 76 (similar to end 76 of suture 34 shown in FIG. 11A). Additionally, connecting filament 74 is provided on foot 24, as described above.

In operation, needle 38A carries one end 76 of suture 34 toward foot 24 after foot 24 has been deployed (as shown). Needle 38A includes a detachable tip 78 such that when needles 38A and 38B are advanced into receptacles 52 in foot 24, the end 76 of suture 34 is connected to one end of the connecting filament 74. Needle 38B is connected to the other end of the connecting filament 74. Needles 38A and 38B are then retracted back into shaft 12, and foot 24 is then rotated back into a non-deployed position. As needle 38A is retracted, tip 78 and suture end 76 are detached from the shank of needle 38A. Needle 38B is engaged with the connecting filament 74, which in turn is engaged with detachable tip 78. Suture end 76 is affixed to tip 78. Thus, as needle 38B is withdrawn, it passes up into shaft 12, through the center of bight 80 to form pre-tied knot 100 by pulling connecting filament 74 and suture end 76 through bight 80.

Figure 32:
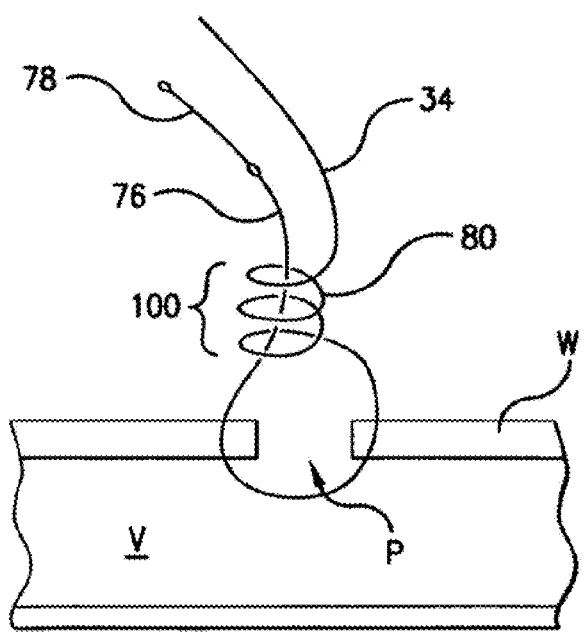
FIG. 32 illustrates the suture pattern after the device of FIG. 31 has been removed, showing the deployment of the pre-tied knot.

When shaft 12 is removed from the patient's body, pre-tied knot 100 will then slide down shaft 12, resulting in the suture pattern as shown in FIG. 32 in which the end 76 of suture 34 passes upwardly through the bight 80.

The suture pattern formed by the pre-tied knot in FIG. 32 is different from that of FIG. 30. Specifically, in FIG. 30, the opposite ends of suture 34 both pass outwardly through puncture P, whereas in the suture pattern shown in FIG. 32, the opposite ends of suture 34 do not pass through the puncture P, but rather through the vessel wall adjacent the puncture.

Figure 33:
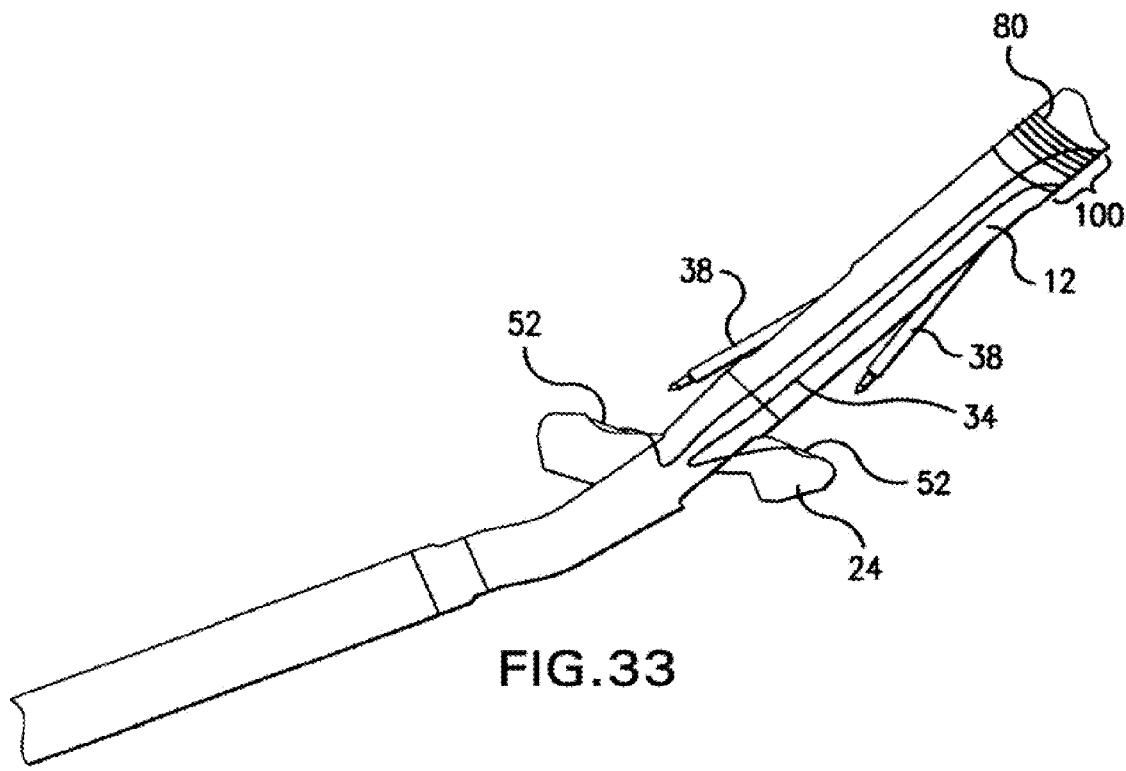
FIG. 33 illustrates another embodiment of a vessel closure device including another embodiment of a pre-tied knot.

FIG. 33 illustrates yet another embodiment of the present invention also including a pre-tied knot 100 disposed around shaft 12, as follows. Each of the opposite ends of the suture 34 are positioned in receptacles 52. Needles 38 are advanced downwardly after foot 24 has been deployed (as shown) such that each of needles 38 become connected to an opposite end of suture 34 at the locations of receptacles 52. For ease of illustration, specific details of connections are not shown in FIG. 33. However, an example of a system suitable for connecting a needle 38 to an end of suture 34 is described above in FIG. 4.

After needles 38 have been connected to opposite ends of suture 34, needles 38 are then both retracted up into lumens in shaft 12, thereby pulling the opposite ends of suture 34 up through shaft 12, and through the bight 80 of suture to define the pre-tied knot 100 (which is initially disposed around the outer surface of shaft 12, as shown).

Figure 34:
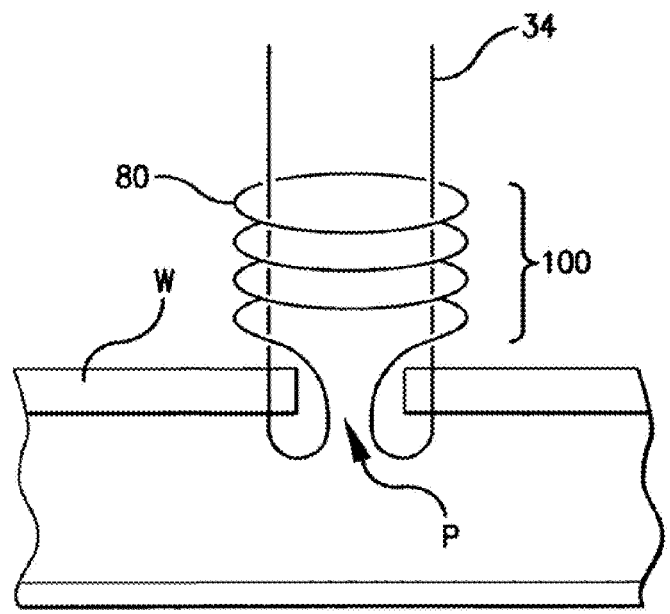
FIG. 34 illustrates the suture pattern after the device of FIG. 33 has been removed, showing the deployment of the pre-tied knot.

When shaft 12 is removed from the patient's body, pre-tied knot 100 will then slide down shaft 12, resulting in the suture pattern as shown in FIG. 34 in which the opposite ends of suture 34 pass upwardly through the center of knot 100, as shown.

The suture pattern in FIG. 34 is slightly different from that of FIG. 30, although both FIGS. 30 and 34 show the opposite ends of suture 34 passing through the center of the bight 80 to form the knot 100. Specifically, when forming the suture pattern of FIG. 30, the opposite ends of suture 34 were both passed down through the tissue wall W, and then up through puncture P; whereas, when forming the suture pattern of FIG. 34, the opposite ends of suture 34 were both passed down through puncture P, and then up through tissue wall W, and further through bight 80 to form knot 100.

Figure 35:
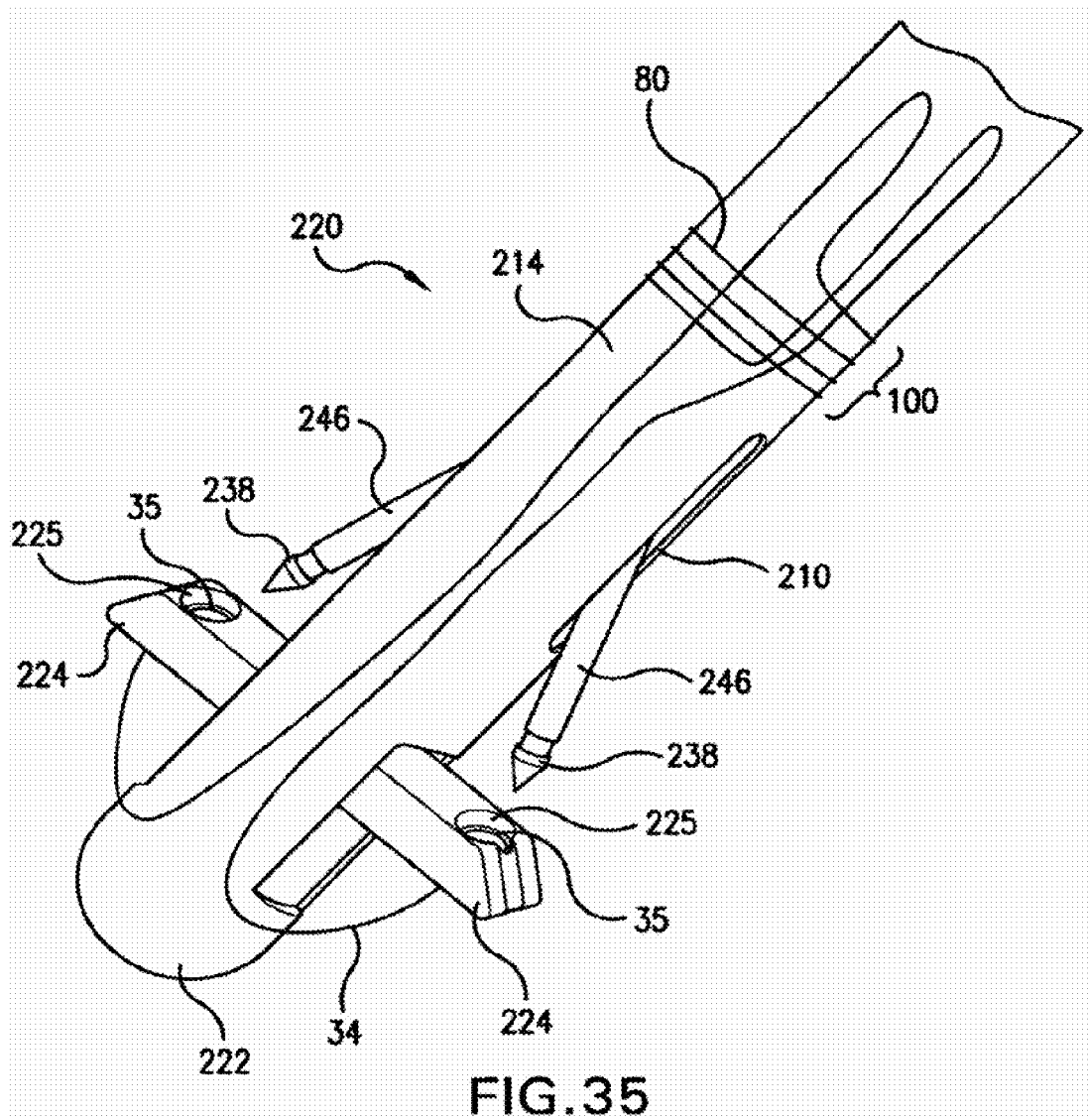
FIG. 35 is a partial perspective view illustrating a vessel closure device incorporating an embodiment of a pre-tied knot according to the principles of the present invention.

FIG. 35 is an illustration of a suturing device 220 similar to an embodiment shown in U.S. Pat. No. 6,245,079, but also incorporating the pre-tied knot of the present invention. U.S. Pat. No. 6,245,079 is incorporated herein by reference in its entirety.

As can be seen in FIG. 35, a suture introducer head 222 having a hollow body 214 with needles 246 therein is provided. Flexible needles 246 bend outward, away from the axis of the device, when in the extended position.

The hollow body 214 has two needle ports or apertures 210 formed therein (one per needle 246) proximal to the suture clasp arms 224. Each suture clasp arm 224 is moved to the retracted position by applying a force to the actuator rod (not shown) within the body 214 if the device. The suture clasp arms 224 hold the looped ends of a suture 34 in needle retaining portions 225.

The needles 246 slide out of the suture device 220 through needle apertures 210. Needles 246 bend radially outwardly to penetrate the vessel wall (not shown) on either side of the puncture.

The suture catches 238 on the needles 246 catch the suture loops 35 held by the suture clasp arms 224 and pull the ends of the suture 34 up through the punctured holes when the needles 246 are retracted proximally. When the needles 246 are retracted into the needle lumens (not shown), they resume a straight configuration.

In accordance with the present invention, suture bight 80 is disposed on the outside surface of the housing with a center portion of bight 80 comprising a pre-tied knot 100 that is wrapped around the outside of device 220, as shown. In this embodiment, suture 34 does not pass through the interior of the device shown in FIG. 35. It should be understood, however, that other embodiments of the invention may include the suture 34 and bight 80 stored inside the shaft or housing of the device rather than on the outside. Yet other configurations may include the detachable tips or link features described above with respect to previously described embodiments.

After needles 246 retrieve opposite ends of suture 34, and pull these ends of the suture back up through the center of bight 80 to define the pre-tied knot 100, and suture clasp arms 224 are rotated back to a non-deployed position, device 220 may be removed from the patient. Pre-tied knot 100 will slide down the shaft, resulting in the same suture pattern as shown in FIG. 34, in which the opposite ends of suture 34 pass upwardly through the center of bight 80.

Figure 36:
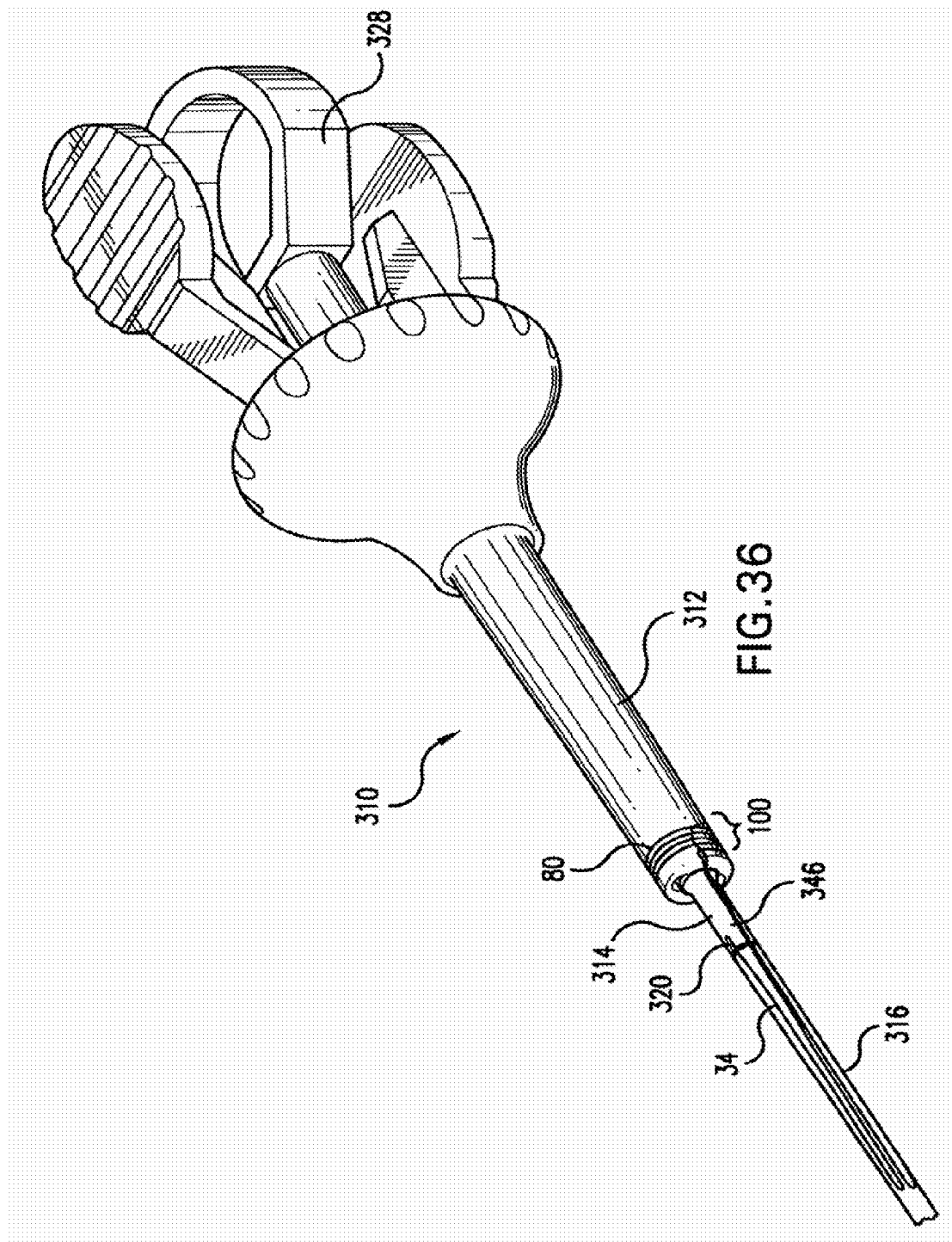
FIG. 36 is a partial perspective view illustrating a vessel closure device incorporating an embodiment of a pre-tied knot according to the principles of the present invention.
Figure 37:
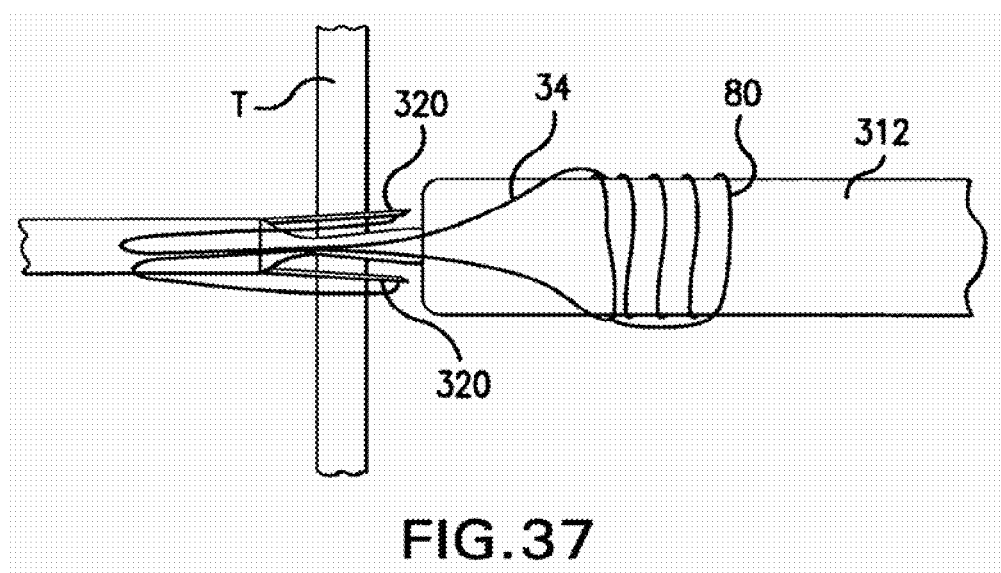
FIG. 37 is a close up view of the device of FIG. 36 showing details of the pre-tied knot.
Figure 38:
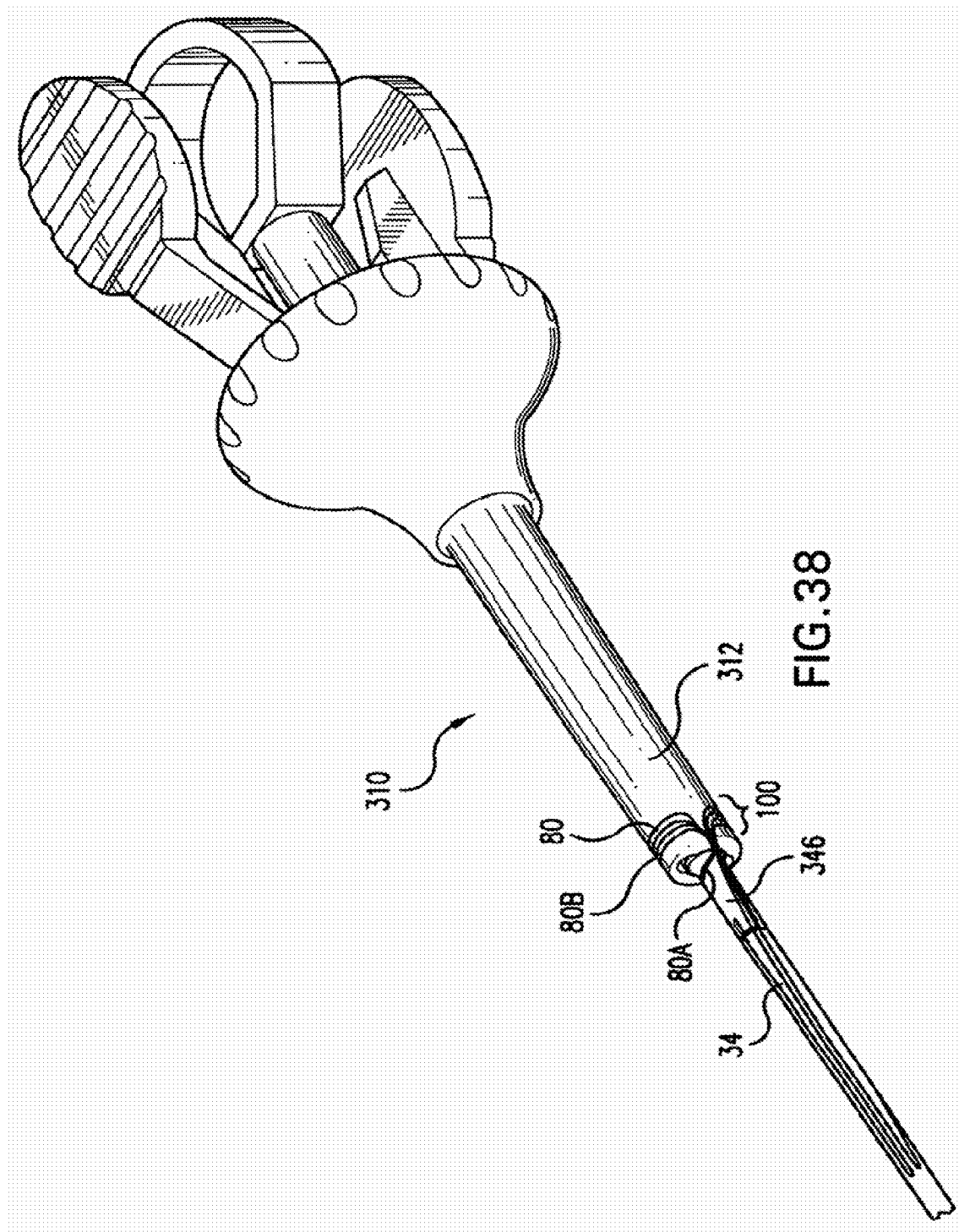
FIG. 38 is a partial perspective view illustrating a vessel closure device incorporating an embodiment of a pre-tied knot according to the principles of the present invention.

FIGS. 36 through 38 are illustrations of a device as shown in U.S. Pat. No. 5,613,974 incorporating the pre-tied knot of the present invention. U.S. Pat. No. 5,613,974 is incorporated herein by reference in its entirety.

FIG. 36 shows a suturing device 310 comprises a guide body 312, a needle guide 314 secured to a distal end of the guide body 312, and a flexible needle sheath 316 secured to the distal end of the needle guide 314. Tissue receiving region 346 is defined by needle guide 314 and the distal face of guide body 312. Needles 320 are mounted with their distal ends in a holster attached to a reciprocatable shaft (not shown). Handle 328 can be pulled proximally in order to draw the needles 320 from the sheath 316, through the needle guide 314, and into the guide body 312. Moreover, suturing device 310 is provided with the capability of delivering a pre-tied suture knot 100.

Guide body 312, needle guide 314, flexible needle sheath 316, needles 320, tissue-receiving region 346 and handle 328 correspond generally to guide body 12, needle guide 14, flexible needle sheath 16, needles 20, tissue-receiving region 346 and handle 28 in U.S. Pat. No. 5,613,974.

Referring to FIG. 36, opposite ends of suture 34 are each connected to the ends of needles 320. Bight 80 is disposed around guide body 312, and is prearranged to define a pre-tied knot 100 when ends of the suture 34 pass therethrough. Bight 80 may include one or more loops of suture 34, and may be prearranged to define a variety of known or new knots.

Further details of the positioning of suture 34 are shown in FIG. 37. After needles 320 have been deployed proximally through a layer of tissue T and received into lumens in guide body 312, bight 80 will slip down the shaft of the device and form a suture pattern similar to or the same as that illustrated in FIG. 30, wherein the ends of suture 34 are passed through the loop or loops of bight 80 to form a pre-tied knot.

FIG. 38 shows suturing device 310 including a modified arrangement of bight 80. Bight 80 includes a first portion 80A prearranged in the tissue receiving region 346 and a second portion 80B prearranged on the guide body 312. The bight 80, including first portion 80A and second portion 80B, is prearranged to define a pre-tied knot 100 when ends of the suture 34 pass therethrough. Bight 80 may include one or more loops of suture 34, and may be prearranged to define a variety of known or new knots.

Figure 39:
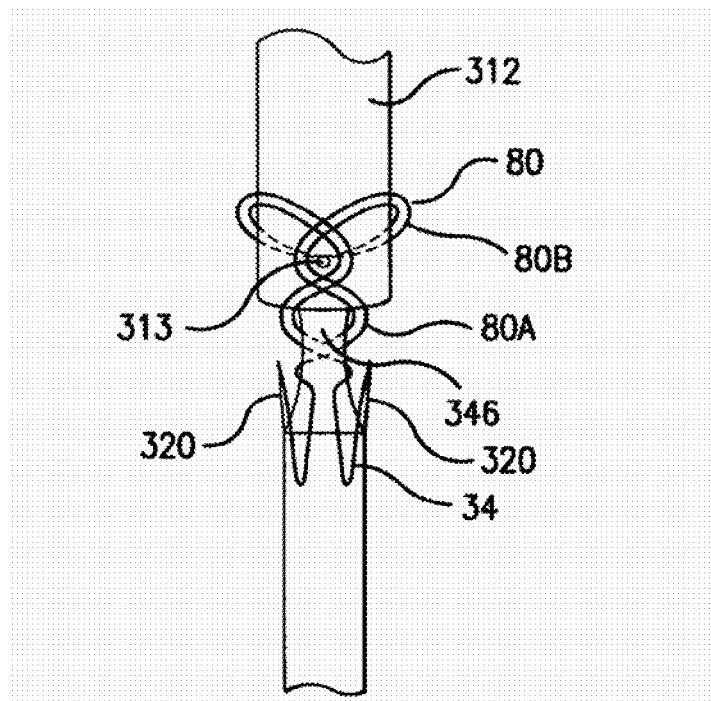
FIG. 39 is a close up view of the device of FIG. 38 showing details of the pre-tied knot.

FIG. 39 shows the arrangement of bight 80 on the device. To wrap bight 80 around the tissue receiving region 346 and the guide body 312 in a modified "figure eight" configuration, a temporary pin 313 is provided to hold the intermediate portions of the loops forming bight 80 in place while the loops forming first portion 80A and second portion 80B are wrapped. Once the bight 80 is in position on the device, the pin 313 is removed and the bight 80 is held on the body of the device with adhesive or a covering such as shrink wrap tubing (not shown). During deployment of the device, the needles 320 carry respective first and second ends of the length of suture 34 over the first portion 80A of the bight 80 and into the guide body 312.

Figure 40:
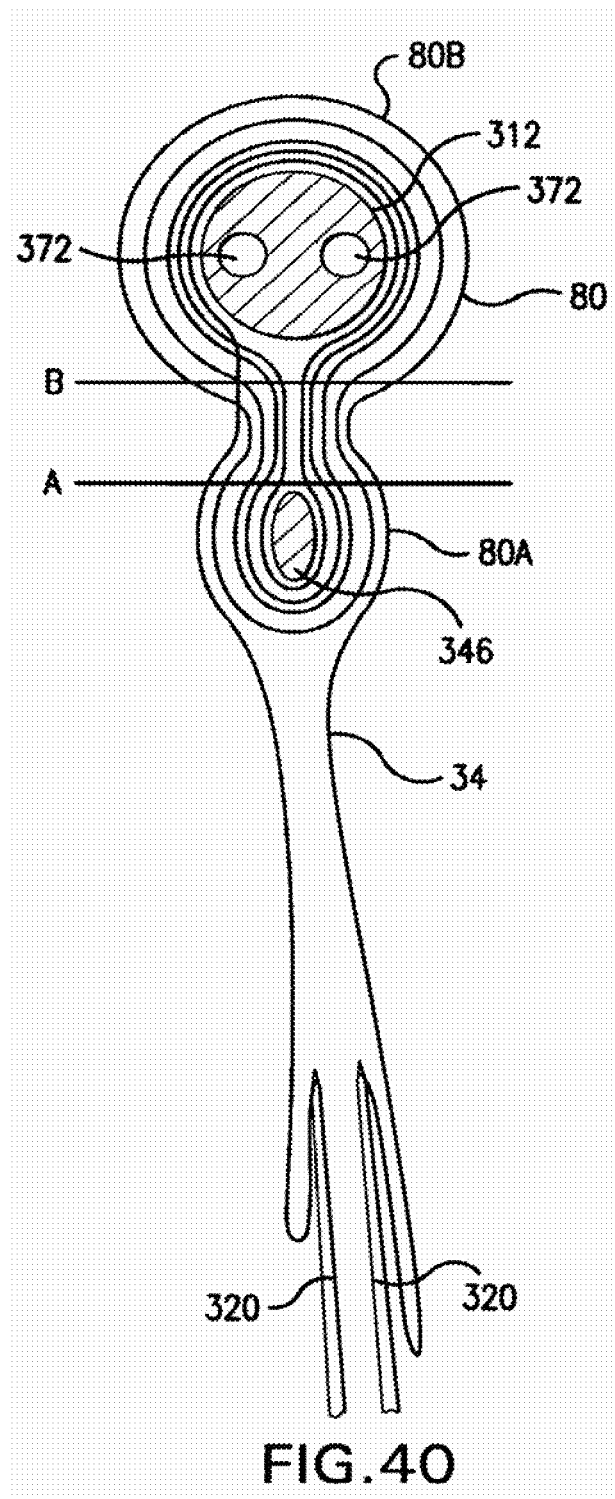
FIG. 40 is a schematic view of the suture bight pattern, developed into a flattened presentation, of the device of FIG. 28.

FIG. 40 shows a schematic view of the suture 34 and needle 320 assembly, wherein the bight 80 is laid out flat for ease of viewing the routing of the suture loops forming bight 80. First portion 80A is shown encircling a cross-sectional representation of the tissue receiving region 346. Second portion 80B is shown encircling a cross-sectional representation of the guide body 312. Needle receiving lumens 372 are defined through the guide body 312. Bight 80 can be visualized as being folded along lines A and B of FIG. 40 when bight 80 is prearranged on the body of the device.

Figure 41:
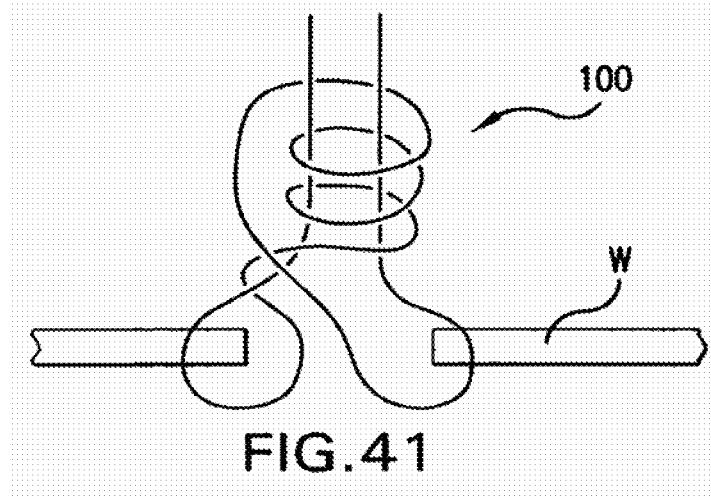
FIG. 41 illustrates the suture pattern after the device of FIG. 38 has been removed, showing the deployment of the pre-tied knot.

FIG. 41 shows a pre-tied knot 100 deployed in a wall W of tissue such as a blood vessel wall. Pre-tied knot 100 is the result of deployment of the device and suture bight 80 arrangement shown in FIGS. 23, 24A, and 24B.

Figure 43:
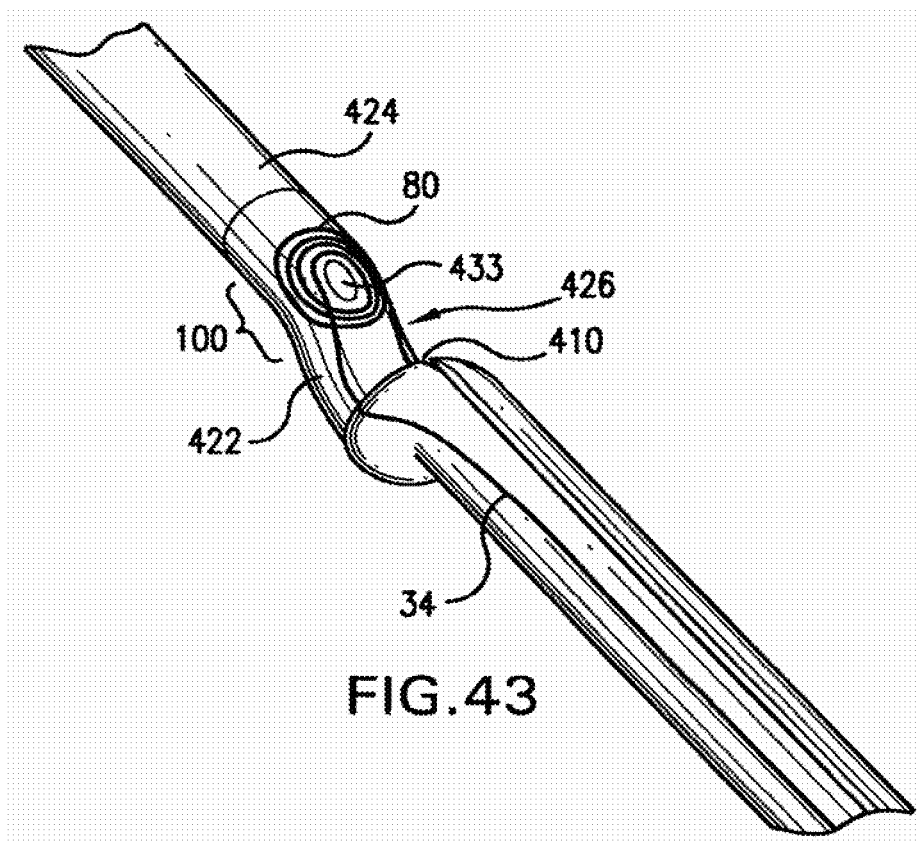
FIG. 43 is a close up view of the device of FIG. 42 showing details of the pre-tied knot.
Figure 46:
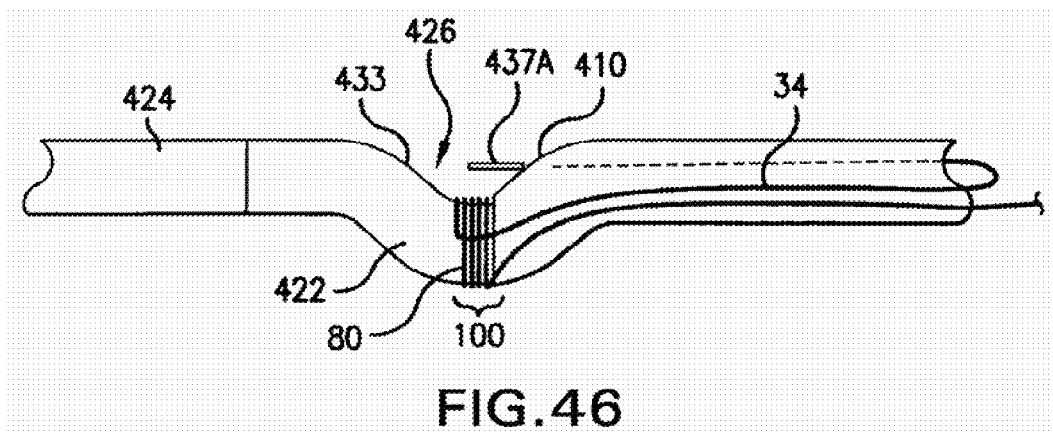
FIG. 46 is a close up view of the device of FIG. 45 showing details of the pre-tied knot.

FIGS. 42 through 46 show additional embodiments of the invention in which a suturing device as shown in U.S. Pat. No. 6,436,109 or in U.S. Pat. No. 6,451,031 incorporates a pre-tied knot. Specifically, FIGS. 42 through 44 show one embodiment of such a device, and FIGS. 45 and 46 show another embodiment of such a device. U.S. Pat. No. 6,436,109 and U.S. Pat. No. 6,451,031 are incorporated herein by reference in their entirety.

FIGS. 42 and 45 show a suturing device 401 that includes a tube 416 of circular or substantially circular cross-section. Tube 416 has a proximal portion 418 and a distal portion 424. The proximal portion 418 extends from a first end 420 to a connecting portion 422. Proximal portion 418 has a first needle lumen (not shown) extending therethrough to a first needle opening 410. Distal portion 424 extends distally from the connecting portion 422. Referring to FIG. 43, distal portion 424 includes a second needle opening 433 facing the first needle opening 410 across a tissue receiving gap 426, which is defined by the connecting portion 422. The second needle opening 433 opens into a second needle lumen (not shown).

Referring again to FIGS. 42 and 45, the connecting portion 422 has an arcuate shape and is coupled between the proximal portion 418 and the distal portion 424. The connecting portion 422 is offset from the proximal and distal portions to create the tissue receiving gap 426. When the connecting portion is received within a puncture in an anatomical structure, a portion of the anatomical structure received within the tissue receiving gap is located on one side of a plane including a central axis of the puncture.

Referring to FIGS. 42 and 43, suture 34 includes a bight 80 of suture that is disposed around the second needle opening 433 (FIG. 43). In this aspect of the invention, each of the needles is connected to opposite ends of suture 34. In operation, needles 437A and 437B (FIG. 42) are sequentially advanced out of first needle opening 410, across gap 426, and into second needle opening 433.

Bight 80 is prearranged to define a pre-tied knot 100 (FIG. 43) when at least one end of suture 34 passes therethrough. Bight 80 may include more than one loop, and may be prearranged to define a variety of known or new knots.

FIGS. 44A through 44D are schematic views showing the sequence of deployment of needles 437A and 437B and suture through bight 80 relative to the tissue wall W having the puncture P which is to be closed. This sequence illustrates the operation of the embodiment of the pre-tied knot shown in FIGS. 42 and 43.

Figure 44A:
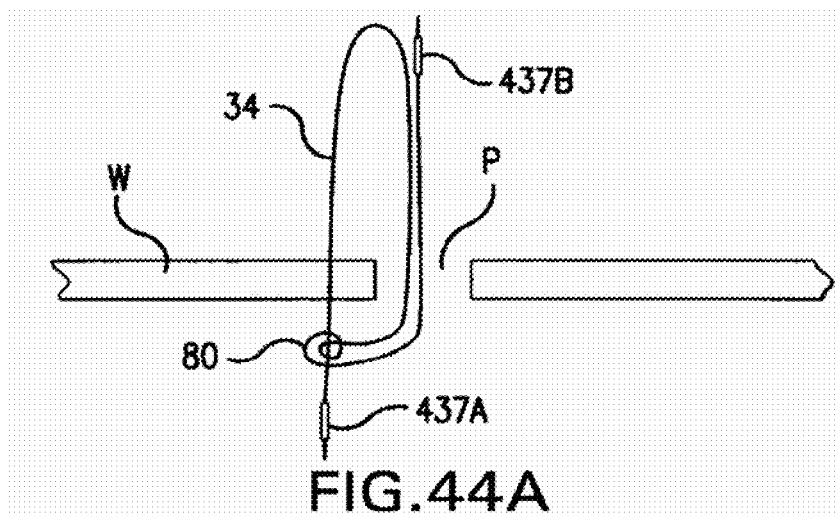
FIGS. 44A-D illustrate the stages of deployment of the needles and suture of the device of FIG. 42.

FIG. 44A shows the bight 80 positioned below the tissue wall W. Needle 437A has been advanced through tissue wall W adjacent puncture P to carry an end of suture 34 through the bight 80.

Figure 44B:
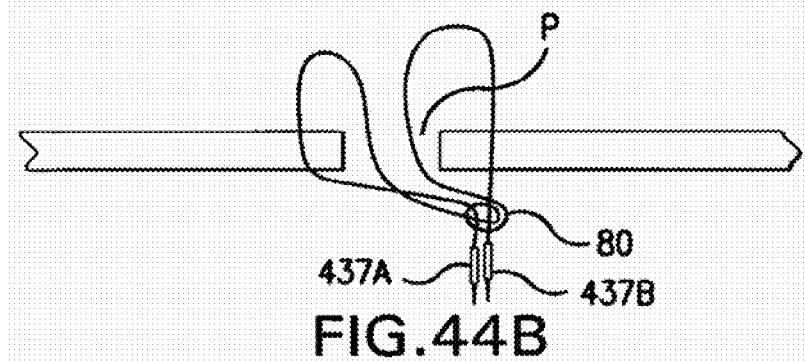

FIG. 44B shows the bight 80 positioned on the opposite side of the puncture P. Second needle 437B has been advanced through tissue wall W adjacent puncture P to carry an end of suture 34 through the bight 80. At this stage, both needles 437A and 437B are disposed in the distal portion of the device (not shown for simplicity of explanation).

Figure 44C:
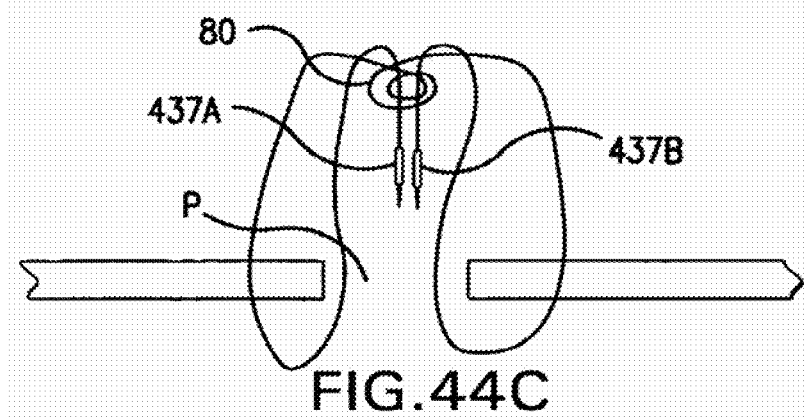
Figure 44D:
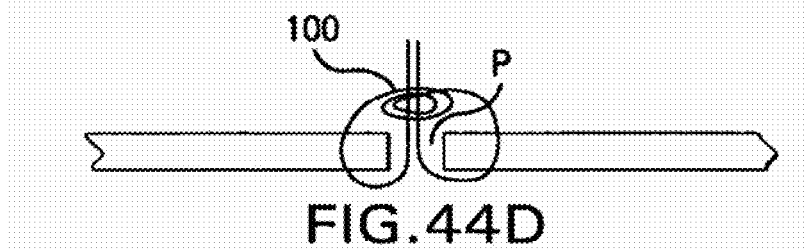

FIG. 44C shows the position of the bight 80 and needles 437A and 437B after the device (not shown) has been withdrawn proximally through the puncture P. FIG. 44D shows the final position of the pre-tied knot 100 after having been advanced and cinched to close the puncture P.

Referring to FIGS. 45 and 46, the bight 80 is disposed around connecting portion 422. In this aspect of the invention, each of needles 437A and 437B is connected to opposite ends of suture 34. In operation, needles 437A and 437B are sequentially advanced out of first needle opening 410, across connecting portion 422, and into second needle opening 433. Needles 437A and 437B pass over bight 80 (FIG. 46) as they cross the tissue receiving gap 426 while advancing distally from proximal portion 418 to distal portion 424.

After device 401 has been removed from the patient's body, bight 80 will then slide down over connecting portion 422 and distal end portion 424 such that the ends of the suture 34 are passed through bight 80 to form a pre-tied knot 100.

In many of the previously-described embodiments of a suturing device, a needle is used to position a suture loop across an opening in a tissue wall. The needle is attached to the suture and pulls the suture through a penetration in the tissue formed by the needle. The needle may be advanced through the tissue to become attached to the suture (or connecting filament), or may be attached to the suture before being advanced to penetrate the tissue. In either case, after the needle is withdrawn, the suture must be severed to detach the needle. In some embodiments describe herein in which the suture is withdrawn through a housing, the needle or needles must be detached from the suture so that the device may be removed from the patient anatomy. Often the suture is cut or severed with scissors or a scalpel. Additional embodiments of a suturing device may include a blade positioned on the device to provide a convenient cutting edge to sever the suture to detach the suture from the needle or needles.

FIG. 47 shows a suturing device 610 of the type having an articulated foot described herein. The suturing device 610 is particularly useful for suturing an opening in a femoral artery of a patient after the completion of a percutaneous transluminal catherization procedure, or the like. Suturing device 610 is an example of the type of device that may include a blade positioned on the device. For convenience of description, only this suturing device embodiment will be described with respect to the suture cutting blade feature. It is to be understood, however, that any suturing device employing a needle and suture to close an opening in a tissue wall may incorporate the suture cutting blade feature described more fully below.

The suturing device 610 shown in FIG. 47 includes a housing 618. One or more needles 638 are operatively associated with the device. The needles 638 are movable with respect to the housing 618. The needles 638 are shown in FIG. 47 withdrawn from the housing 618. In this exemplary embodiment, only one of the two needles 638 are shown attached to a length of suture 634. In other embodiments, both needles may be attached to the suture 634. Alternatively, the device may only include one needle.

A suture cutting blade 690 is positioned on the device 610 such that when the needle 638 and attached suture 634 are withdrawn from the device, the suture 634 can be drawn across the blade 690 to sever the suture. FIG. 47 shows the position of the needle and suture with respect to the housing 618 and the blade 690 just prior to the suture being cut to detach the needle 638 from the length of suture. As can be seen in FIG. 47, a portion of the suture may remain attached to the needle 638 due to the suture being cut at a short distance from the end of the needle. The length of suture that is used to close the opening in the tissue will be detached from the needle or needles. Once the needle 638 is cut away from the length of suture that has been withdrawn from the proximal end 622 of the housing 618, the device 610 can be removed from the patient's anatomy without interference from the needle actuation handle 620.

FIG. 48 shows a cross-section of the housing 618 with the blade 690 mounted on the housing. The blade 690 is shown having a generally V-shaped cutting edge. Alternate embodiments of the blade may have straight, curved, serrated, or any of a variety of cutting edge shapes or configurations. The blade may be a separate piece that is mounted to the housing. For example, a blade made of stainless steel or other metal may be affixed or mounted on a plastic housing. Other well-known techniques such as overmolding may be employed to assemble or form the blade and housing. Alternatively, the blade may be integrally formed in the plastic housing by molding or machining a sharp edge at a selected location on the housing, for example. The blade may be fixedly mounted with respect to the housing, or other component of the device, on which the blade is positioned. Alternatively, the blade may be movably mounted so as to provide a moving cutting edge.

As shown in FIG. 48, the housing 618 has a distal end 624 and a proximal end 622. The blade 690 is positioned near the distal end 624, while the suture is withdrawn through the housing 618 from the proximal end 622. The suture is then directed distally toward the blade to be drawn across the blade. The cutting edge of the blade faces distally with respect to the housing and the operator of the device. The position of the blade and the orientation of the cutting edge allows the operator to pass or loop the suture across the cutting edge of the blade and pull in a proximal direction to draw the suture across the blade to sever the suture. The position of the blade relative to where the suture exits the housing results in the suture being cut at a location along its length that provides a sufficient length of suture tail to remain after the suture has been severed. The suture tail (or pair of tails) are used to tie and advance a knot (or advance a pre-tied knot) to the tissue being sutured.

The housing 618 defines an opening 625 that provides access to the cutting edge of the blade. In the embodiment shown in FIGS. 47 and 48, the opening 625 is defined near the distal end 624 of the housing, and the blade 690 is positioned in the opening. A blade guard 628 may be provided to protect the blade from damage or to protect the user of the device from injury caused by the blade.

Figure 49:
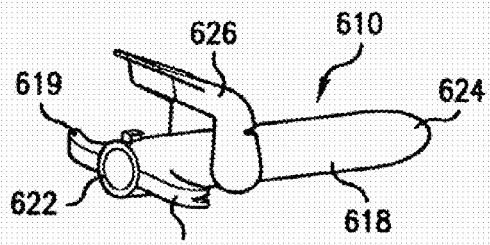
FIG. 49 is a perspective view of a housing of a suturing device showing other embodiments of the suture cutting blade positioned at various locations on the housing.

FIG. 49 shows a portion of a suturing device 610 that includes a housing 618. FIG. 49 illustrates alternate locations for a suture cutting blade. Housing 618 has a proximal end 622 and a distal end 624. Housing also includes a foot handle 626 movable mounted on the housing. Housing 618 also includes finger grips 619 extending from the housing near the proximal end 622 of the housing.

Figure 50:
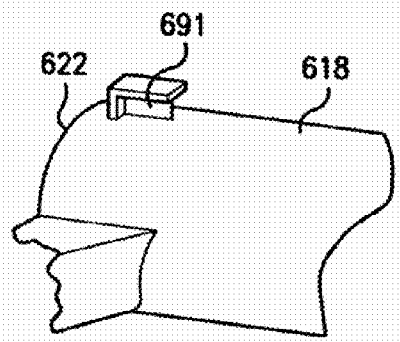
FIG. 50 is an enlarged partial view of the housing of FIG. 49 showing an embodiment of a suture cutting blade positioned near the proximal end of the housing.

FIG. 50 is an enlarged partial view of the proximal end 622 of the housing 618 of FIG. 49. In this embodiment, suture cutting blade 691 is positioned near the proximal end of the housing. The blade 691 is mounted on the outside surface of the housing.

Figure 51:
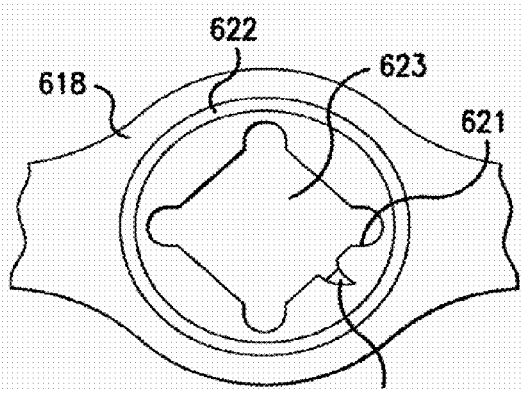
FIG. 51 is an enlarged partial proximal end view of the housing of FIG. 49 showing an embodiment of a suture cutting blade positioned near the proximal end of the housing.

FIG. 51 shows an enlarged end view of the proximal end 622 of the housing 618 of FIG. 49. As shown in FIG. 51, housing 618 is a hollow body having proximal opening 623 and an inner surface 621. In this embodiment, suture cutting blade 691 is mounted on the inner surface 621 within the proximal opening, such that when the suture is withdrawn from the housing, the suture can be moved laterally to be drawn across the suture cutting blade 691 and severed.

Figure 52:
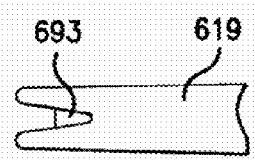
FIG. 52 is an enlarged partial proximal end view of the housing of FIG. 49 showing an embodiment of a suture cutting blade positioned on a finger grip.

FIG. 52 shows an enlarged proximal end view of a finger grip 619 of the housing 618 of FIG. 49. A suture cutting blade 693 is mounted on the finger grip 619. In this exemplary embodiment, the suture may be withdrawn from the proximal end of the housing and looped over the end of the finger grip 619 and across the blade 619 to sever the suture.

Figure 53:
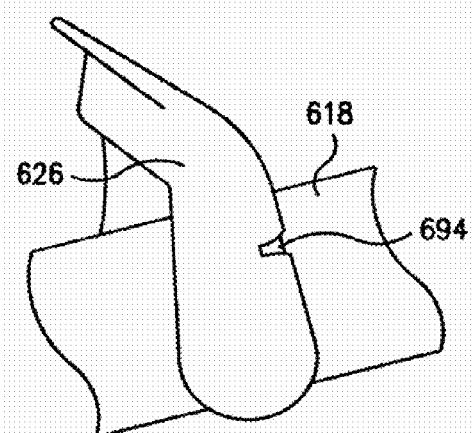
FIG. 53 is an enlarged partial view of the housing of FIG. 49 showing an embodiment of a suture cutting blade positioned on a movable handle.

FIG. 53 shows an enlarged view of the foot handle 626 that is movably mounted with respect to the housing 618. Foot handle 626 is used to deploy a foot in various embodiments of suturing devices described herein. A suture cutting blade 694 is mounted on the movable handle 626.

In operation, a tissue suturing device is used by advancing a needle distally to penetrate the tissue and position a suture through the tissue. In various embodiments described herein, attaching the suture to the needle is accomplished by moving the needles distally through a housing of a device to connect to the suture. The suture is positioned through the tissue by withdrawing the needle proximally through the proximal end of the housing. Finally, the needle can be separated from the suture by drawing the suture across the suture cutting blade to sever the needle from the suture.

The various embodiments of a suturing device described herein can be provided to position a suture across an opening in a wall of a blood vessel to close the opening. In a femoral artery closure procedure, for example, such devices are used to advance the suture and the needle percutaneously through subcutaneous tissue to a blood vessel access site.

The present invention offers surgeons an automated method for delivering a pre-tied knot to an incision formed in a tissue wall. The present invention simplifies the effort associated with a surgeon manually delivering a knot to an incision site. Thus, the present invention reduces the time required to accurately and precisely place a suture knot in close proximity to an incision formed in a lumen, thereby decreasing both the overall time a patient spends in procedure and recovery and the costs associated therewith.

While the exemplary embodiments have been described in some detail for clarity of understanding, a wide variety of modifications, adaptations, and changes will be apparent to those of skill in the art. Hence, the scope of the present invention is limited solely by the appended claims.

What is claimed is:

1. A device for closing an opening in tissue, the device comprising:
   a shaft having a proximal end and a distal end, said shaft having at least one pin;
   a pivotable foot having a proximal foot end, a distal foot end, and at least one slot, said at least one slot being formed in a side of said pivotable foot and receiving said at least one pin at said distal end of said shaft, said foot being movable with respect to said shaft and said at least one slot being axially moveable with respect to said at least one pin, said at least one slot and said at least one pin cooperating to rotate and proximally displace said foot with said at least one pin moving toward a distal end of said at least one slot; and
   a flexible guidebody extending from said distal foot end of said foot.

2. The device of claim 1, wherein said foot is rotationally movable about said at least one pin.

3. The device of claim 1, wherein said foot is moveable via motion of an actuation wire.

4. A device for closing an opening in tissue, the device comprising:
   a shaft having a proximal end and a distal end, said shaft having at least one pin;
   a pivotable foot on said distal end of said shaft, said pivotable foot having a proximal foot end, a distal foot end, and at least one slot, said at least one slot being formed in a side of said pivotable foot and receiving said at least one pin at said distal end of said shaft, said pivotable foot being movable with respect to said shaft and said at least one slot being axially moveable with respect to said shaft, said pivotable foot having at least one receptacle, said at least one receptacle having at least one slot oriented with respect to a surface of the at least one receptacle; and
   a flexible guidebody abutting and extending directly from said distal foot end of said pivotable foot.

5. The device of claim 4, wherein said at least one slot extends substantially tangentially to said surface of said at least one receptacle.

6. The device of claim 4, wherein said at least one slot extends laterally through said foot.

7. The device of claim 4, further comprising a movable flap disposed over said at least one slot.

8. The device of claim 7, wherein a portion of said movable flap is affixed along one side of said at least one slot and another portion of said movable flap flexing into said at least one receptacle to release a suture disposed within the slot.

9. A device for closing an opening in tissue, the device comprising:
   a shaft having a proximal end and a distal end;
   a foot proximate said distal end of said shaft, said foot having a proximal foot end, a distal foot end, and a slot, said slot being configured to facilitate slidablilty of the foot with respect to said shaft, said foot being axially moveable with respect to said shaft; and
   a flexible guidebody extending from said distal foot end of said foot, wherein said flexible guidebody abuts and is directly connected to said distal foot end of said foot.

10. The device of claim 9, wherein said foot is oriented about a longitudinal axis of said shaft.

11. The device of claim 9, wherein said foot further comprises at least one cuff pocket.

12. The device of claim 9, wherein said foot further comprises a cam surface.

13. A device for closing an opening in a tissue, the device comprising:
   a shaft having a proximal end and a distal end, said shaft having at least one pin;
   a pivotable first foot on said distal end of said shaft, said first foot having a proximal foot end, a distal foot end, and at least one slot, said at least one slot being formed in a side of said pivotable foot and receiving said at least one pin at said distal end of said shaft, said pivotable foot being movable with respect to said shaft and said at least one slot being axially moveable with respect to said shaft, each of said proximal foot end and said distal foot end including a receptacle configured to receive a suture cuff, with said distal foot end having a generally tapered configuration, said receptacle oriented transverse to a longitudinal axis of said foot;
   a flexible guidebody extending from said distal foot end of said foot.

14. The device of claim 13, wherein first foot is pivotally associated with said shaft.

* * * * *